United States Patent
Nukaga et al.

(10) Patent No.: US 9,399,789 B2
(45) Date of Patent: Jul. 26, 2016

(54) BASE BODY AND METHOD OF MANUFACTURING BASE BODY

(71) Applicants: FUJIKURA LTD., Koto-ku, Tokyo (JP); BIO ELECTRO-MECHANICAL AUTONOMOUS NANO SYSTEMS LABORATORY TECHNOLOGY RESEARCH ASSOCIATION, Chiyoda-ku, Tokyo (JP); THE UNIVERSITY OF TOKYO, Bunkyo-ku, Tokyo (JP)

(72) Inventors: Osamu Nukaga, Sakura (JP); Satoshi Yamamoto, Sakura (JP); Kazuhito Tabata, Bunkyo-ku (JP); Masakazu Sugiyama, Bunkyo-ku (JP); Shoji Takeuchi, Bunkyo-ku (JP)

(73) Assignees: FUJIKURA LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 479 days.

(21) Appl. No.: 13/741,825

(22) Filed: Jan. 15, 2013

(65) Prior Publication Data
US 2013/0196426 A1    Aug. 1, 2013

Related U.S. Application Data

(63) Continuation of application No. PCT/JP2011/066237, filed on Jul. 15, 2011.

(30) Foreign Application Priority Data

Jul. 16, 2010  (JP) .................................. 2010-161870
Sep. 30, 2010  (JP) .................................. 2010-221440

(51) Int. Cl.
C12M 1/36    (2006.01)
C12M 3/00    (2006.01)
(Continued)

(52) U.S. Cl.
CPC ................. *C12Q 1/24* (2013.01); *B23K 26/006* (2013.01); *G01N 33/48728* (2013.01)

(58) Field of Classification Search
CPC ...... C12Q 1/24; B23K 6/006; G01N 33/48728
USPC .............................. 435/309.1; 422/69; 216/56
See application file for complete search history.

(56) References Cited

U.S. PATENT DOCUMENTS

| 4,526,445 A | 7/1985 | Wogoman |
| 2001/0050312 A1* | 12/2001 | Koide ............................ 235/454 |

(Continued)

FOREIGN PATENT DOCUMENTS

| JP | 5271538 | 5/1977 |
| JP | 59219714 A | 12/1984 |

(Continued)

OTHER PUBLICATIONS

Adrian Y. Lau et al., "Open-access microfluidic patch-clamp array with raised lateral cell trapping sites", Lab Chip, Sep. 27, 2006, pp. 1510-1515, vol. 6.

(Continued)

*Primary Examiner* — Michael Hobbs
(74) *Attorney, Agent, or Firm* — Sughrue Mion, PLLC

(57) ABSTRACT

Disclosed is a substrate (10A) for trapping a microorganism or cell (T), characterized by comprising a base (4) and having a space (2) into which a fluid (R) containing the microorganism or cell (T) is introduced and a microfine suction hole (1) through which the space (2) communicates with the outside of the base (4). The substrate is further characterized in that the space (2) has been formed in the base (4), and at least the portion of the base (4) which forms the microfine suction hole (1) is constituted of a single member.

12 Claims, 43 Drawing Sheets

(51) Int. Cl.
    *C12Q 1/24*     (2006.01)
    *B23K 26/00*     (2014.01)
    *G01N 33/487*     (2006.01)

(56) References Cited

U.S. PATENT DOCUMENTS

| | | | |
|---|---|---|---|
| 2003/0113833 A1* | 6/2003 | Oka et al. | 435/29 |
| 2005/0064137 A1* | 3/2005 | Hunt et al. | 428/131 |
| 2010/0062214 A1 | 3/2010 | Wo et al. | |
| 2013/0230912 A1* | 9/2013 | Nukaga | B01J 19/0093 435/288.7 |

FOREIGN PATENT DOCUMENTS

| | | |
|---|---|---|
| JP | 10337173 A | 12/1998 |
| JP | 2007-222132 A | 9/2007 |
| JP | 2007222132 A | 9/2007 |
| JP | 2008-288577 A | 11/2008 |
| JP | 2008-539711 A | 11/2008 |
| JP | 2008288577 A | 11/2008 |
| JP | 2009-133687 A | 6/2009 |
| JP | 2009133687 A | 6/2009 |
| WO | 02/055653 A1 | 7/2002 |
| WO | 2005/089253 A2 | 9/2005 |
| WO | 2006/117541 A1 | 11/2006 |
| WO | 2007/117987 A2 | 10/2007 |

OTHER PUBLICATIONS

International Search Report for PCT/JP2011/066237 dated Oct. 25, 2011.
Japanese Office Action; Application No. 2012-524608; Nov. 4, 2015.
Communication dated Apr. 11, 2016 from the European Patent Office issued in corresponding Application No. 11806907.9.
Chen et al., "Hourglass-shaped aperture for cellular electrophysiological study", Applied Physics Letters, American Institute of Physics 91, (2007) 3 pages total.
Ionescu-Zanetti et al., "Mammalian electrophysiology on a microfluidic platform", PNAS, Jun. 28, 2005, vol. 102 No. 26, XP007918139, pp. 9112-9117.

* cited by examiner

BASE BODY AND METHOD OF MANUFACTURING BASE BODY

CROSS REFERENCE TO RELATED APPLICATIONS

This application is a continuation application based on a PCT Patent Application No. PCT/JP2011/066237, filed Jul. 15, 2011, whose priority is claimed on Japanese Patent Application No. 2010-161870, filed Jul. 16, 2010, and Japanese Patent Application No. 2010-221440, filed Sep. 30, 2010, the entire content of which are hereby incorporated by reference.

BACKGROUND OF THE INVENTION

1. Field of the Invention

The present invention relates to a base body having micropores and a method of manufacturing the base body.

More specifically, the invention relates to a base body having fine vacuum holes that trap microorganisms or cell bodies and a method of manufacturing the base body.

In addition, more specifically, the invention relates to a base body having micropores that form a lipid membrane and a method of manufacturing the base body.

2. Description of the Related Art

As a method of physically trapping a cell or cultivated cell taken from a living organism and performing electrophysiological measurement on the cell, a patch-clamp method is known.

As a method of physically trapping a cell of the related art, a method of sucking a cell 101 at a hole provided on the side surface of a resin well 108 (FIG. 45) is known (see, Adrian Y. Lau, et al., Lab Chip, 2006, 6, 1510-1515 (Non Patent Document 1)).

Non Patent Document 1 discloses a method in which the behaviors of the cell trapped at the hole are directly observed using a high-power microscope from the rear surface of an apparatus and an apparatus that can perform electrophysiological measurements on the cell membrane and the like of the cell trapped at the hole.

The method and the apparatus become effective as means for explaining new biological characteristics.

Generally, in the patch-clamp method, there is a demand for closely attaching the adsorption portion (opening portion) at the hole and the cell membrane so as to achieve robust sealing of 1 gigaohm or more (high resistance sealing).

In order to form the above high resistance sealing, it is necessary to stabilize the sealing between the cell membrane and the adsorption portion, and a decrease in the diameter of the opening of the adsorption portion and a level difference or seam-free hole shape are required.

The cell trapping apparatus disclosed in Non Patent Document 1 has a base body to which two members formed of a resin (PDMS) are adhered, and micro holes are provided in the interface of the adhesion.

The base body is provided with a space in which a fluid is accumulated.

The space is formed by punching the base body.

When the base body is punched, the micro holes formed in advance in the base body are opened to the space.

Since the cell trapping apparatus is manufactured using a method of punching a resin, it is difficult to process the shape of the adsorption portion (opening portion) of the micro holes which is to trap a cell into a desired shape.

In addition, in a case in which a plurality of adsorption portions (opening portions) are formed in the base body, it is difficult to form the plurality of adsorption portions (opening portions) into a uniform shape.

In addition, since the base body is a resin, it is difficult to form fine holes having a minor axis of approximately less than 2 μm.

Furthermore, since the micro holes are formed by adhering two members to each other, a seam or level difference at which the two members are adhered to each other is present in the adsorption portion.

When the above seam or level difference is present, there is a case in which stable trapping of a cell is difficult.

That is, since the accuracy of the size or shape of the micro holes or the adsorption portion formed in the cell trapping apparatus is low, there is a problem in that it is difficult to trap a cell as desired.

In addition, in a case in which an electrophysiological measurement is conducted, since the sealing between the cell membrane and the adsorption portion becomes unstable, there is a problem in that a highly accurate electrophysiological measurement is difficult.

Furthermore, in order to trap microorganisms (having a short side on the order of nanometers) that are smaller than cells, it is necessary to highly accurately form the diameter of the short side of the adsorption portion (opening portion) of the micro holes at least on the order of nanometers.

However, since the cell trapping apparatus is configured by adhering the plurality of resin substrates 110 and 112 in Non Patent Document 1, it is difficult to process the adsorption portion (opening portion) on the order of nanometers.

Meanwhile, as a method of detecting a macromolecule such as a protein material included in a cell only at an extremely small amount, the western blotting of the related art or the method of Patent Document 1 (PCT International Publication No. WO2008-539711) is known.

However, while the movement distance of a protein or the like differs depending on the molecular weight, the movement distance may be as extremely short as approximately 100 nm to 350 nm.

Therefore, in the western blotting having a large volume of detection area, a large amount of cells are required in order for antibodies to come into contact with and trap an extremely small amount of a protein material.

Meanwhile, in the method of Patent Document 1, since the fluidic channel is provided in the side wall including PDMS, it is difficult to process the minor axis of the fluidic channel on the order of nanometers.

Therefore, there is a low probability that an extremely small amount of a protein material comes into contact with the analysis components (detection portion) of the fluidic channel having a minor axis on the order of micrometers, and a large amount of cells are required in order to obtain a desired amount of a protein material.

In addition, in the apparatus disclosed in Patent Document 1, since the fluidic channel is formed by adhering two members to each other, a seam or level difference at which the two members are adhered to each other is also present at the fluidic channel input end, and the sealing between a cell and the fluidic channel input end becomes unstable.

Therefore, when a cell is sucked, a void is caused between the cell and the fluidic channel, and there is a possibility that an extremely small amount of a protein material will not intrude into the fluidic channel and leaks outside.

As described above, in any method, a large amount of cells are required, and there is a problem in that detection is impossible unless a cell fragment is taken from a patient or the like.

In order to stably carry out an electrophysiological measurement and increase accuracy, decreasing the cross-section area of a hole that traps a cell may become effective.

Therefore, there is a demand for development of an apparatus having a hole with a diameter of the opening which is smaller than the diameter (approximately 2 μm to 4 μm) of the opening of a hole in the related art and a method of manufacturing the apparatus.

In addition, for the hole with a diameter of the opening which is smaller than the diameter (approximately 2 μm to 4 μm) of the opening of a hole in the related art, there is a demand for development of an apparatus that can reconfigure the same lipid bilayer membrane as the cell membrane artificially and a method of manufacturing the same.

In addition, as described above, there is a demand for development of an apparatus having micropores which can be used to trap fine particles such as microorganisms and cells, form a lipid membrane, and the like, and a method of manufacturing the apparatus.

On the other hand, in order to quantitatively detect a macromolecule such as a protein material which is included only a small amount of cell or the like efficiently, there is a demand for development of an apparatus which has nanofluidic channels, has no seam at the fluidic channel input end, and is formed of a transparent base member so that fluorescent labels can be observed, and a method of manufacturing the apparatus.

SUMMARY OF THE INVENTION

The invention has been made in consideration of the above circumferences, and provides a base body for trapping microorganisms or cells in which holes that trap microorganisms or cells are formed of a single base member, and the trapped microorganisms or cells are easily observed, and provides a method of manufacturing the base body.

In addition, the invention has been made in consideration of the above circumferences, and provides a base body having holes being formed of a single base member for forming a lipid membrane, is base member, can easily form a lipid membrane, and can stably maintain the formed lipid membrane, and a method of manufacturing the base body.

In addition, the invention has been made in consideration of the above circumferences, and provides a base body having micropores which is available for a plurality of uses such as trapping of fine particles such as microorganisms, cells, and the like and forming of a lipid membrane, and a method of manufacturing the base body.

A first aspect of the invention is a base body for trapping microorganisms or cells, including a base member, a space which allows a fluid including microorganisms or cells to flow therein, and fine vacuum holes that communicate the space to the outside of the base member, in which the space is provided in the base member, and at least the portions that configure the fine vacuum holes in the base member are formed of a single member.

In the first aspect, the single member preferably transmits at least some wavelengths of light from light having a wavelength of 0.1 μm to 10 μm.

In the first aspect, the single member is preferably formed of silicon, glass, silica, or sapphire.

In the first aspect, the fine vacuum holes are preferably formed by irradiating the base body with a laser, and, furthermore, removing modified regions irradiated with the laser through an etching treatment.

A second aspect of the invention is a method of manufacturing the base body for trapping microorganisms or cells according to the first aspect, at least having a process A1 in which a laser having a pulse duration on the order of picoseconds or less is irradiated to areas in the single member which become the fine vacuum holes so as to form modified regions in the areas, a process A2 in which the space is formed in the single member, and a process A3 in which the modified regions are removed from the single member through etching.

A third aspect of the invention is the method of manufacturing the base body for trapping microorganisms or cells according to the first aspect, preferably having a process B1 in which the space is formed in the single member, a process B2 in which a laser having a pulse duration on the order of picoseconds or less is irradiated to areas in the single member which become the fine vacuum holes so as to form modified regions in the areas, and a process B3 in which the modified regions are removed from the single member through etching.

In the second or third aspect, the irradiation intensity of the laser light is preferably lower than or equal to the lower limit value of a laser irradiation intensity at which a periodic structure can be formed in the modified regions and is greater than or equal to the lower limit value of a laser irradiation intensity at which the etching resistance of the modified regions can be decreased.

In the second or third aspect, the laser light is preferably condensed using a lens.

A fourth aspect of the invention is a base body for forming a lipid membrane, including a base member, a space which allows liquid including lipids to flow therein, and micropores that communicate the space to the outside of the base member, in which the space is provided in the base member, and at least the portions that configure the micropores in the base member are formed of a single member.

In the fourth aspect, the single member preferably transmits at least some wavelengths of light from light having a wavelength of 0.1 μm to 10 μm.

In the fourth aspect, the single member is preferably formed of silicon, glass, silica, or sapphire.

In the fourth aspect, the micropores are preferably formed by irradiating the base member with a laser, and, furthermore, removing the modified regions through an etching treatment.

A fifth aspect of the invention is a method of manufacturing the base body for forming a lipid membrane according to the fourth aspect, at least having a process A1 in which a laser having a pulse duration on the order of picoseconds or less is irradiated to areas in the single member which become the micropores so as to form modified regions in the areas, a process A2 in which the space is formed in the single member, and a process A3 in which the modified regions are removed from the single member through etching.

A sixth aspect of the invention is the method of manufacturing the base body for forming a lipid membrane according to the fourth aspect, preferably having a process B1 in which the space is formed in the single member, a process B2 in which a laser having a pulse duration on the order of picoseconds or less is irradiated to areas in the single member which become the micropores so as to form modified regions in the areas, and a process B3 in which the modified regions are removed from the single member through etching.

In the fifth or sixth aspect, the irradiation intensity of the laser light is preferably lower than or equal to the lower limit value of a laser irradiation intensity at which a periodic structure can be formed in the modified regions and is greater than or equal to the lower limit value of a laser irradiation intensity at which the etching resistance of the modified regions can be decreased.

In the fifth or sixth aspect, the laser light is preferably condensed using a lens.

A seventh aspect of the invention is a base body including a base member, a space which allows a fluid to flow therein, and micropores that communicate the space to the outside of the base member, in which the space is provided in the base member, and at least the portions that configure the micropores in the base member are formed of a single member.

In the seventh aspect, the single member preferably transmits at least some wavelengths of light from light having a wavelength of 0.1 µm to 10 µm.

In the seventh aspect, the single member is preferably formed of silicon, glass, silica, or sapphire.

In the seventh aspect, the micropores are preferably formed by irradiating the base body with a laser, and, furthermore, removing the modified regions through an etching treatment.

An eighth aspect of the invention is a method of manufacturing the base body according to the seventh aspect, at least having a process A1 in which a laser having a pulse duration on the order of picoseconds or less is irradiated to areas in the single member which become the micropores so as to form modified regions in the areas, a process A2 in which the space is formed in the single member, and a process A3 in which the modified regions are removed from the single member through etching.

A ninth aspect of the invention is the method of manufacturing the base body according to the seventh aspect, preferably having a process B1 in which the space is formed in the single member, a process B2 in which a laser having a pulse duration on the order of picoseconds or less is irradiated to areas in the single member which become the micropores so as to form modified regions in the areas, and a process B3 in which the modified regions are removed from the single member through etching.

In the eighth or ninth aspect, the irradiation intensity of the laser light is preferably lower than or equal to the lower limit value of a laser irradiation intensity at which a periodic structure can be formed in the modified regions and is greater than or equal to the lower limit value of a laser irradiation intensity at which the etching resistance of the modified regions can be decreased.

In the eighth or ninth aspect, the laser light is preferably condensed using a lens.

A tenth aspect of the invention is an apparatus that detects a macromolecule, including a base member, a space, and nanofluidic channels that communicate the space to the outside of the base member, in which the space is provided in the base member, at least the portions that configure the nanofluidic channels in the base member are constituted by a single member, and the nanofluidic channels are preferably disposed substantially perpendicularly to the side surface of the space.

In the tenth aspect, the minor axis of the nanofluidic channel is preferably in a range of 0.05 µm to 1.00 µm.

In the tenth aspect, the major axis of the nanofluidic channel is preferably in a range of 1 µm to 6 µm.

In the tenth aspect, the total length of the nanofluidic channels is preferably in a range of 20 µm to 50000 µm.

In the tenth aspect, an analysis component for detecting a macromolecule is preferably disposed at the inner wall of the nanofluidic channels.

In the tenth aspect, an adsorption component is preferably disposed between the inner wall of the nanofluidic channels and the analysis components.

The base body for trapping microorganisms or cells of the invention makes it possible for microorganisms or cells to be adsorbed and trapped at the adsorption portion including one end of the fine vacuum holes that are open to the space which allows a fluid including the microorganisms or the cells to flow therein by applying suction to the fine vacuum holes from the outside of the base member.

Since the adsorption portion is formed of a single member, there is no seam, and it is possible to substantially remove level differences.

Therefore, it is possible to sufficiently attach the trapped microorganisms or cells to the adsorption portion, and to stably maintain a state in which the microorganisms or cells are trapped.

Therefore, the microorganisms or cells are easily observed, and, when an electrophysiological measurement is conducted, a highly accurate measurement is possible.

In a case in which the single member transmits at least some of the wavelengths (0.1 µm to 10 µm) of an ordinarily used processing laser light beam from light having a wavelength of 0.1 µm to 10 µm, it is possible to modify and process the single member by irradiating the laser beam.

In addition, in a case in which the single member transmits at least some wavelengths of visible light (0.36 µm to 0.83 µm) from light having the above wavelength, it becomes easier to optically observe the trapped microorganisms or cells through the single member using a microscope or the like.

Furthermore, in a case in which the single member transmits at least some wavelengths of ultraviolet light or visible light (0.1 µm to 0.83 µm) from light having the above wavelength, it is possible to fluorescently observe the structure in the microorganisms or cells dyed with a fluorescent pigment.

Here, the sentence "the single member transmits light rays having specific wavelengths" refers to everything about a state in which light rays are incident to the member so as to obtain transmitted light rays from the member.

In a case in which the single member is a member formed of silicon, glass, silica, or sapphire, it is possible to further increase the process accuracy of the fine vacuum holes, and to form the adsorption portion with a diameter of the opening on the order of nanometers.

Therefore, it is relatively easy to form high resistance sealing between the trapped cells and the adsorption portion.

At this time, in a case in which the adsorption portion having the fine vacuum holes is formed of glass, silica, or sapphire, a process in which a treatment that supplies insulation properties is conducted becomes unnecessary.

In a case in which high resistance sealing is formed, and an electrophysiological measurement of the trapped cells is conducted, it is also possible to appropriately use a method of measuring the potential difference (membrane potential) and the like between the inside and outside of the cell for the base body.

In a case in which the material that forms the adsorption portion is glass or silica, and an electrophysiological measurement of the trapped cell is conducted, since high resistance sealing on the order of gigaohms is realized between the cell and the adsorption portion, a more accurate measurement is possible.

In a case in which the method of forming the fine vacuum holes is a method in which the base member is modified through laser irradiation and the modified regions are removed through an etching treatment, it is possible to form a base body having fine vacuum holes accurately disposed at a high density in the base member.

The method of manufacturing a base body for trapping microorganisms or cells of the invention is capable of forming fine vacuum holes in the single member and to communicate one end of the fine vacuum holes to the space present in the base body.

In addition, it also becomes possible to form the adsorption portion including one end of the fine vacuum holes with a diameter of the opening on the order of nanometers.

The base body for forming a lipid membrane of the invention is capable of forming a lipid membrane at the opening portions of the micropores which are exposed to the space which allows a fluid including a lipid to flow therein.

Furthermore, an operation that applies a pressure to or reduces the pressure on the formed lipid membrane through the fluid in the micropores.

The above operation can enhance the stability of the lipid membrane or control the thickness or shape of the lipid membrane.

Since the opening portion is formed of a single member, there is no seam, and it is possible to substantially remove level differences.

Therefore, the formed lipid membrane can be stably maintained.

Therefore, the lipid membrane is easily observed, and, when an electrophysiological measurement is conducted by introducing a membrane protein material such as an ion channel or an ion pump to the lipid membrane, a highly accurate measurement is possible.

In a case in which the single member transmits at least some of the wavelengths (0.1 μm to 10 μm) of an ordinarily used processing laser light beam from light having a wavelength of 0.1 μm to 10 μm, it is possible to modify and process the single member by irradiating with the laser light ray.

In addition, in a case in which the single member transmits at least some wavelengths of visible light (0.36 μm to 0.83 μm) from light having the above wavelength, it is easier to optically observe the formed lipid membrane through the single member using a microscope or the like.

Furthermore, in a case in which the single member transmits at least some wavelengths of ultraviolet light or visible light (0.1 μm to 0.83 μm) from light having the above wavelength, it is possible to fluorescently observe the behaviors of a biomolecule such as a membrane protein material labeled with a fluorescent pigment in the lipid membrane.

Here, the sentence "the single member transmits light rays having specific wavelengths" refers to everything about a state in which light rays are incident to the member so as to obtain transmitted light rays from the member.

In a case in which the single member is a member formed of silicon, glass, silica, or sapphire, it is possible to further increase the process accuracy of the micropores, and to form the opening portion with the diameter of the opening on the order of nanometers.

Therefore, it is relatively easy to form high resistance sealing between the formed lipid membrane and the opening portion.

At this time, in a case in which a material that forms the opening portion of the micropores is glass, silica, or sapphire, a process in which a treatment that supplies insulation properties becomes unnecessary.

In a case in which high resistance sealing is formed, and an electrophysiological measurement of the membrane protein material and the like introduced to the lipid membrane is conducted, it is also possible to appropriately use a method of measuring the potential difference (membrane potential) and the like between the inside and outside of the lipid membrane for the base body.

In a case in which a material that forms the opening portion is glass or silica, and an electrophysiological measurement of the membrane protein material and the like introduced to the formed lipid membrane is conducted, since high resistance sealing on the order of gigaohms is realized between the lipid membrane and the opening portion, a more accurate measurement is possible.

In a case in which the method of forming the micropores is a method in which the base member is modified through laser irradiation and the modified regions are removed through an etching treatment, it is possible to form a base body having micropores accurately disposed at a high density in the base member.

The method of manufacturing a base body for forming a lipid membrane of the invention is capable of forming micropores in the single member and to communicate one end of the micropores to the space present in the base body.

In addition, it also becomes possible to form the opening portion including one end of the micropores with a diameter of the opening on the order of nanometers.

In addition, the base body and manufacturing method of the invention provide a base body having micropores which is available for a plurality of uses such as trapping of fine particles such as microorganisms or cells, formation of a lipid membrane, and the like.

The effects in a case in which the base body of the invention is used to trap fine particles are as follows.

The base body of the invention makes it possible for fine particles to be adsorbed and trapped at the adsorption portion including one end of the micropores (fine vacuum holes) that are open to the space which allows a fluid including the fine particles to flow therein by sucking the micropores (fine vacuum holes) from the outside of the base member.

Since the adsorption portion is formed of a single member, there is no seam, and it is possible to substantially remove level differences.

Therefore, it is possible to sufficiently attach the trapped fine particles to the adsorption portion, and to stably maintain a state in which the fine particles are trapped.

Therefore, the fine particles are easily observed.

Furthermore, in a case in which the fine particles are microorganisms or cells, it is possible to highly accurately carry out an electrophysiological measurement of the fine particles.

In a case in which the single member transmits at least some of the wavelengths (0.1 μm to 10 μm) of an ordinarily used processing laser light beam from light having a wavelength of 0.1 μm to 10 μm, it is possible to modify and process the single member by irradiating with the laser beam.

In addition, in a case in which the single member transmits at least some wavelengths of visible light (0.36 μm to 0.83 μm) from light having the above wavelength, it is easier to optically observe the trapped fine particles through the single member using a microscope or the like.

Furthermore, in a case in which the single member transmits at least some wavelengths of ultraviolet light or visible light (0.1 μm to 0.83 μm) from light having the above wavelength, it is possible to fluorescently observe the fine particles labeled with a fluorescent pigment.

Here, the sentence "the single member transmits specific wavelengths of light" refers to everything about a state in which light is incident to the member so as to obtain transmitted light from the member.

In a case in which the single member is a member formed of silicon, glass, silica, or sapphire, it is possible to further increase the process accuracy of the micropores (fine vacuum holes), and to form the adsorption portion with a diameter of the opening on the order of nanometers.

Therefore, it is relatively easy to form high resistance sealing between the trapped cell (fine particle) and the adsorption portion.

At this time, in a case in which a material that forms the adsorption portion having the micropores (fine vacuum holes) is glass, silica, or sapphire, a process in which a treatment that supplies insulation properties becomes unnecessary.

In a case in which high resistance sealing is formed, and an electrophysiological measurement of the trapped cell (fine particle) is conducted, it is also possible to appropriately use a method of measuring the potential difference (membrane potential) and the like between the inside and outside of the cell for the base body.

In a case in which a material that forms the adsorption portion is glass or silica, and an electrophysiological measurement of the trapped cell (fine particle) is conducted, since high resistance sealing on the order of gigaohms is realized between the cell and the adsorption portion, a more accurate measurement is possible.

In a case in which the method of forming the micropores (fine vacuum holes) is a method in which the base member is modified through laser irradiation and the modified regions are removed through an etching treatment, it is possible to form a base body having micropores (fine vacuum holes) accurately disposed at a high density in the base member.

The method of manufacturing a base body of the invention is capable of forming micropores (fine vacuum holes) in the single member and to communicate one end of the micropores (fine vacuum holes) to the space present in the base body.

In addition, it also becomes possible to form the adsorption portion including one end of the micropores (fine vacuum holes) with a diameter of the opening on the order of nanometers.

DESCRIPTION OF THE PREFERRED EMBODIMENTS

Hereinafter, the invention will be described based on preferable embodiments with reference to the accompanying drawings.

First Embodiment of a Base Body for Trapping Microorganisms or Cells

[Base Body 10A]

Figure 1:
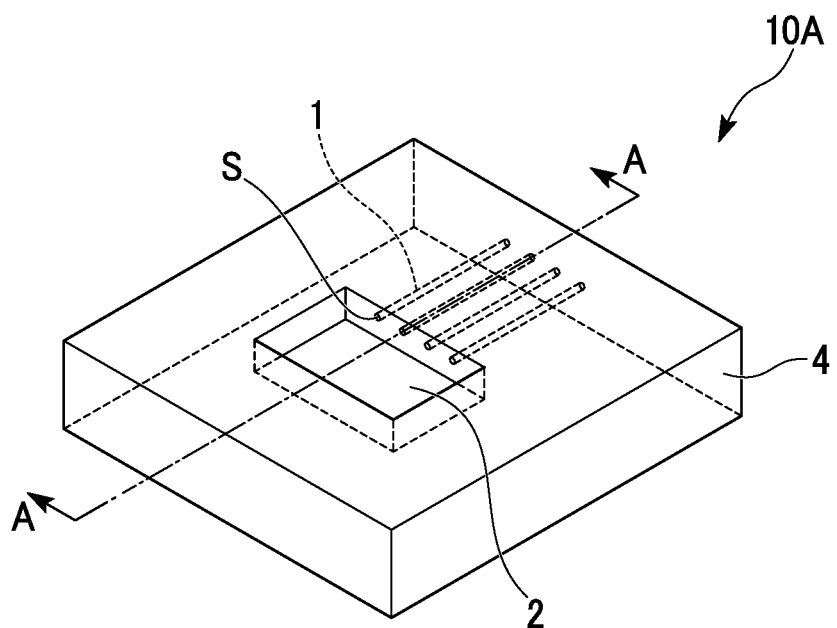
FIG. 1 is a schematic perspective view showing an example of a base body for trapping microorganisms or cells according to the invention.

FIG. 1 is a perspective view of a base body 10A which is a first embodiment of the base body for trapping microorganisms or cells according to the invention (hereinafter sometimes referred to simply as the "base body").

Figure 2:
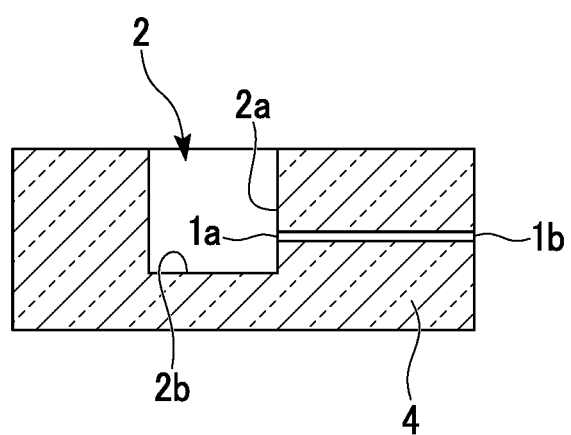
FIG. 2 is a cross-sectional view taken along the line A-A in FIG. 1.
Figure 3:
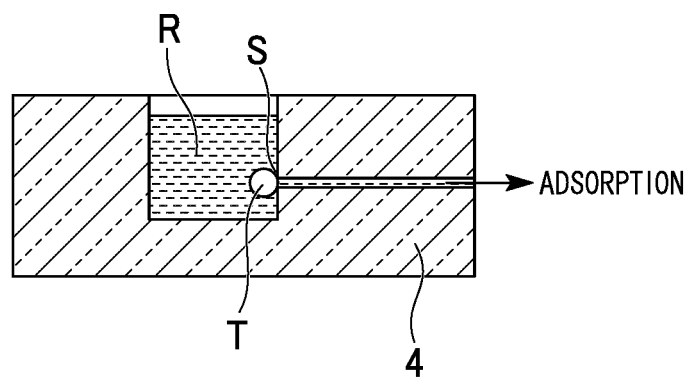
FIG. 3 is a schematic view showing an appearance in which a microorganism or cell body is trapped at the adsorption portion in the cross-sectional view of FIG. 2.

FIGS. 2 and 3 are schematic views showing a cross-section taken along the line A-A in FIG. 1.

The base body 10A is a base body having fine vacuum holes 1 that trap microorganisms or cells T.

The base body 10A includes a space (well 2) which is provided in a base member 4 and allows a fluid R including microorganisms or cells T to flow in, and the fine vacuum holes 1 that communicate the well 2 to the outside of the base member 4, and, at least portions that configure the fine vacuum holes 1 in the base member 4 are formed of a single member.

In the base body 10A, the well 2 is provided on the top surface side of the base member 4.

The well 2 configures a space which allows the microorganisms or cells T to flow in.

Adsorption portions S at which the first end portions 1a of the fine vacuum holes 1 are exposed are formed at the side surface 2a of the well 2.

At least some of the top surface or bottom surface 2b of the well 2 is opened or constituted by a transparent member (not shown) so that microorganisms or cells T trapped at the adsorption portion S can be optically observed.

In addition, at least portions that configure the fine vacuum holes 1 in the base body 10A are formed of a single member.

If the fine vacuum holes 1 are opened on a side surface 2a of the well 2 as described above, when being observed from a bottom surface 2b or a top surface of the well 2 of the base member, the fine vacuum holes 1 and observation subjects are not overlapped, and therefore it is possible to easily observe the microorganisms or cells T.

In a case in which the trapped microorganisms or cells are observed from the bottom surface of the base member, the observation subject is focused by adjusting the distance between the observation subject and the object lens (working distance).

However, in a case in which the distance between the bottom surface of the base member and the observation subjects is larger than the working distance necessary for observation, it is not possible to focus the observation subjects.

In order to avoid such a circumstance, it is possible to decrease the distance between the bottom surface of the base member and the observation subject by carrying out polishing or like of the bottom surface of the base member so as to decrease the thickness of the base member.

However, in a case in which fine vacuum holes that are opened at the bottom surface $2b$ of the well are formed, since the fine vacuum holes are present between the bottom surface $2b$ of the well and the bottom surface of the base member, there are cases in which it is difficult to decrease the thickness of the base member by carrying out polishing or the like of the bottom surface of the base member.

Therefore, the fine vacuum holes are preferably opened at the side surface $2a$ of the well as in the base body 10A.

In the invention, the fluid R including the microorganisms or cells T which are the observation subjects is not particularly limited, and examples thereof include blood, a cell culture fluid, a potable liquid, river water, and the like.

In addition, air including molds or the like is also included in the fluid R.

Here, the sentence "the fluid R is made to flow into the space" means that the fluid R is fed into the space from the outside of the space.

The fluid R that has flowed in may be stopped and remain (or come to a halt) in the space, or may be allowed to flow out of the space.

In the latter case, a flow of the fluid R is generated in the space by continuously making the fluid R flow into the space.

The above action is applied to all the base bodies according to the invention.

In the base body 10A shown in FIG. 1, the single member configures not only the fine vacuum holes 1 but also the entire base member 4.

Examples of the material of the single member include silicon, glass, silica, sapphire, and the like.

The material is preferably a material that is excellent in terms of workability when forming the fine vacuum holes 1.

Among them, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the above laser light is transmitted, it is possible to form modified regions by irradiating with the laser to the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIG. 1, the single member that configures the base member 4 is a transparent glass substrate.

As shown in FIGS. 2 and 3, the fine vacuum holes 1 communicate the well 2 to the outside of the base member 4.

First end portions $1a$ of the fine vacuum holes 1 are exposed (opened) at the side surface $2a$ of the well 2, and form the adsorption portions S.

Second end portions $1b$ of the fine vacuum holes 1 are exposed at a side surface of the base member 4, and are end portions provided at the opposite location of the first end portions.

In the invention, when the fine vacuum holes 1 communicate the space (well 2) to the outside of the base member 4, the second end portions $1b$ of the fine vacuum holes 1 may be exposed and opened at the side surface (outside) of the base member 4 like the base body 10A of FIG. 1.

Furthermore, for example, as a fine vacuum hole $31\alpha$ in the base body described below (FIG. 28), the second end portion of the fine vacuum hole $31\alpha$ may be opened to a first fluidic channel $33\alpha$, and be communicated to the outside of the base member 34 through the first fluidic channel $33\alpha$.

In addition, the fluidic channel that communicates to the outside is not limited to the first fluidic channel $33\alpha$, and the second end portion may be communicated to the outside of the base member 34 through other paths (for example, fluidic channels, wells, and the like).

The meaning of "the fine vacuum holes that communicate the space and the outside of the base member" described herein is applied to all the base bodies according to the invention.

It is possible to trap microorganisms or cells included in the fluid R on the adsorption portion S by sucking the fluid R in the well 2 from the second end portion $1b$ side of the fine vacuum holes 1 which is exposed to the outside of the base member 4.

The power for the suction is not particularly limited, and it is possible to supply the power by connecting a sucking portion (not shown), for example, a syringe or a pump, to the second end portion $1b$ of the fine vacuum hole 1.

The fine vacuum holes 1 are formed in a single glass substrate 4, and are through holes having no seam or adhered surface.

Naturally, there is no seam or adhered surface in the adsorption portions S at the end portion of the fine vacuum holes.

Therefore, the attaching force between the microorganisms or cells T and the adsorption portion S is sufficiently increased.

In addition, since the fine vacuum holes 1 and the peripheral portions of the fine vacuum holes 1 are formed of the single glass substrate 4, and are through holes having no seam or adhered surface, peeling or breakage in an adhered surface does not occur due to the deformation or chemical-induced damage of the glass substrate 4.

Therefore, even when heating sterilization or chemical sterilization is repeatedly conducted on the glass substrate 4, there is no case in which the glass substrate 4 is broken.

The above fact can be said to be a particularly excellent characteristic for base bodies that trap microorganisms or cells on which heating sterilization or chemical sterilization needs to be conducted on a routine basis.

Furthermore, since no difference in refractive index is caused in locations near the fine vacuum holes 1, it is easier to condense light from the adsorption portion S.

Therefore, it is possible to easily observe the trapped microorganisms or cells.

Here, the "adsorption portion S" refers to an area which the microorganisms or cells T come into contact with or come close to in the side surface $2a$ of the well 2.

The diameter of the hole at the first end portion 1a of the fine vacuum hole 1 and at the side surface 2a of the well 2 which configures the adsorption portion S is preferably in a range of 0.02 μm to 5 μm.

Even in the above range, the diameter is preferably in a range of 0.02 μm to 0.8 μm for microorganisms that are smaller than the cells.

In a case in which the hole is oval or substantially oval, it is possible to trap the microorganisms or cells T as long as the minor axis (the diameter of the shortest opening portion) of the hole is in a range of 0.02 μm to 5 μm.

That is, the minor axis of the hole needs to be sufficiently small such that the microorganisms or cells T cannot pass through the fine vacuum holes 1.

For example, in the case of trapping red blood cells (6 μm to 8 μm), the minor axis needs to be approximately 1 μm, and, in the case of trapping natto bacilli (grass bacilli; 0.7 μm to 2 μm), the minor axis needs to be approximately 0.2 μm.

The range of the minor axis is preferably 0.02 μm to 2 μm.

Even in the above range, the diameter is preferably in a range of 0.02 μm to 0.8 μm in order to trap microorganisms that are smaller than the cells.

When the diameter is less than the lower limit value of the range, there is a concern that the sucking force at the adsorption portion S may be too weak such that it is not possible to trap the microorganisms or cells T.

When the diameter exceeds the upper limit value of the range, there is a concern that the microorganisms or cells T may pass through the fine vacuum holes 1 and may not be able to be trapped.

On the other hand, the major axis (the diameter of the longest opening portion) of the hole may be appropriately adjusted depending on the size of the microorganisms or cells T to be trapped, and is in a range of, for example, 0.2 μm to 10 μm.

Furthermore, in a case in which an electrophysiological measurement is carried out, the major axis is preferably made to be smaller than the size of the cells or microorganisms, and is in a range of, for example, 0.2 μm to 5 μm.

When the minor axis of the hole diameter of the hole is highly accurately processed on the order of nanometers, the base bodies are capable of trapping microorganisms that are smaller than the cells, and it becomes possible to observe microorganisms which have been observed in a group singly or in a small group.

As a result, the apparatus can become means for confirming a variety of biological characteristics of microorganisms which have thus far not been explained.

If the diameter of the hole at the adsorption portion is made to be smaller, when the electrophysiological characteristics of cells are measured, stabilized sealing properties are realized between cell membranes and the adsorption portion, and therefore it is possible to stably carry out a measurement of electrophysiological characteristics.

In FIGS. 2 and 3, the fine vacuum holes 1 are formed substantially perpendicularly with respect to the side surface 2a of the well 2.

However, the fine vacuum holes do not necessarily need to be substantially perpendicular to the side surface, and can be freely disposed in the single glass substrate 4 in accordance with the design of the base body 10A.

Furthermore, it is also possible to process the diameter of the opening at a location near the first end portion 1a of the fine vacuum hole 1 to be slightly wider than the diameter of the opening of the fine vacuum hole 1.

At this time, since the base bodies are capable of trapping the microorganisms or cells T in a state in which some of the microorganisms or cells are embedded in the first end portion of the fine vacuum hole 1, the base bodies are capable of trapping the microorganisms or cells more stably for a long period of time even when liquid flows in the well 2.

Here, a description has been made regarding the well 2, but the above description is also applied to a structure having a second fluidic channels 22 described below and the like.

A plurality of fine vacuum holes 1 may be disposed in the base body 10A.

Since each of the fine vacuum holes 1 has the adsorption portion S, it is possible to trap a plurality of microorganisms or cells T.

In a case in which a plurality of fine vacuum holes 1 are disposed, the interval between the adjacent fine vacuum holes 1 is preferably provided in consideration of the size of the microorganisms or cells T to be trapped.

For example, in a case in which the size of the microorganisms or cells T to be trapped is approximately 3 μm, the interval between the adjacent fine vacuum holes 1 is greater than or equal to 6 μm.

As a result, since the plurality of trapped microorganisms or cells T do not come close to each other, it is possible to easily carry out observation or electrophysiological measurements.

When a plurality of fine vacuum holes 1 are disposed in a single well 2, it is possible to separately control the suction at the fine vacuum hole 1 by connecting an independent sucking portion (not shown) such as a syringe or a pump to the second end portion 1b side of the single fine vacuum hole 1.

Therefore, it is possible to independently control the trapping of the microorganisms or cells T using the fine vacuum holes 1.

When the material of the base member 4 is silicon, glass, silica, sapphire, or the like, since the materials are excellent in terms of workability, it is possible to tightly dispose a plurality of fine vacuum holes 1 therein.

In the base body 10A, the bottom surface 2b of the well 2 is constituted by the base member 4 including a glass substrate.

The top surface of the well 2 which is opposite to the bottom surface 2b is opened, and has no lid.

Therefore, it is possible to optically observe the microorganisms or cells T trapped at the adsorption portions S from the bottom surface 2b or top surface using a microscope or the like.

Meanwhile, it is not a definite requirement that the top surface have no lid, and the top surface may be covered with a lid including a member such as a plastic, resin, or glass member (not shown).

Since it is possible to trap the microorganisms or cells T present in the well 2 while observing the microorganisms or cells, it is possible to appropriately adjust the sucking force depending on the state of the microorganisms or cells by, for example, strengthening the sucking force when an attempt is made to trap cells, and weakening the sucking force to an extent at which the cell membranes are not broken after trapping the cells.

In a case in which an electrophysiological measurement of the trapped microorganisms or cells T is conducted, for example, electrodes (not shown) may be disposed respectively in the well 2 and the fine vacuum hole 1b side.

Alternatively, external electrodes may be used through an extracellular buffer, an intracellular fluid, or the like.

Since the adsorption portion S is formed of the single glass substrate 4, it is possible to form high resistance sealing with respect to the cell membranes of the cells T.

Therefore, a well-known patch-clamp method of the related art can be applied.

At this time, it is possible to carry out a more highly accurate electrophysiological measurement than in the related art by making the diameters of the openings of the holes on the first end portion 1a side of the fine vacuum holes 1 that configure the adsorption portions S be smaller than the diameter of the opening (approximately 2 μm to 4 μm) of the hole of a patch pipet or the like of the related art.

[Base Body 10B]

Figure 4:
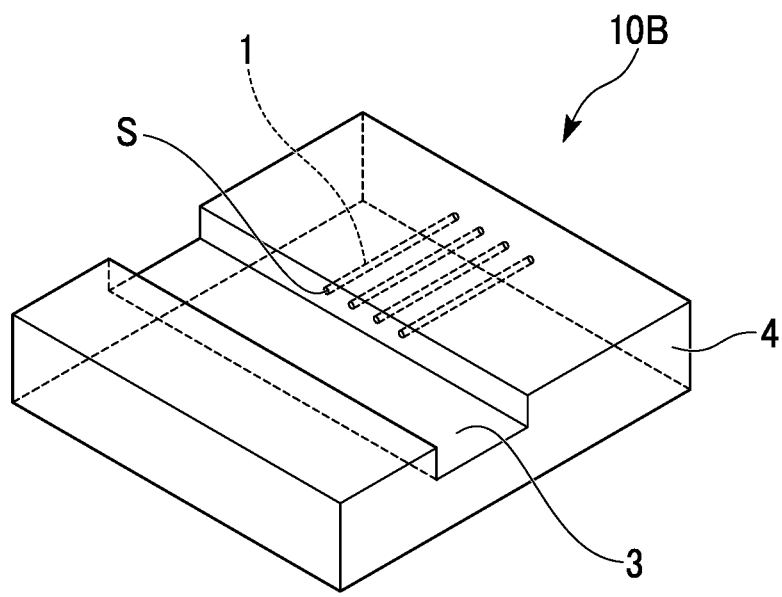
FIG. 4 is a schematic perspective view showing an example of the base body for trapping microorganisms or cells according to the invention.

An embodiment of the base body for trapping microorganisms or cells of the invention is also shown in a base body 10B of FIG. 4.

In the base body 10B, a fluidic channel 3 is provided on the top surface side of the base member 4.

The fluidic channel 3 is a space which allows the microorganisms or cells T to flow in and circulate.

Compared to the well 2 in the base body 10A, the fluidic channel 3 in the base body 10B can allow a larger amount of the fluid R to flow in and circulate.

Other configurations of the base body 10B are the same as in the base body 10A.

[Base Body 10C]

Figure 5:
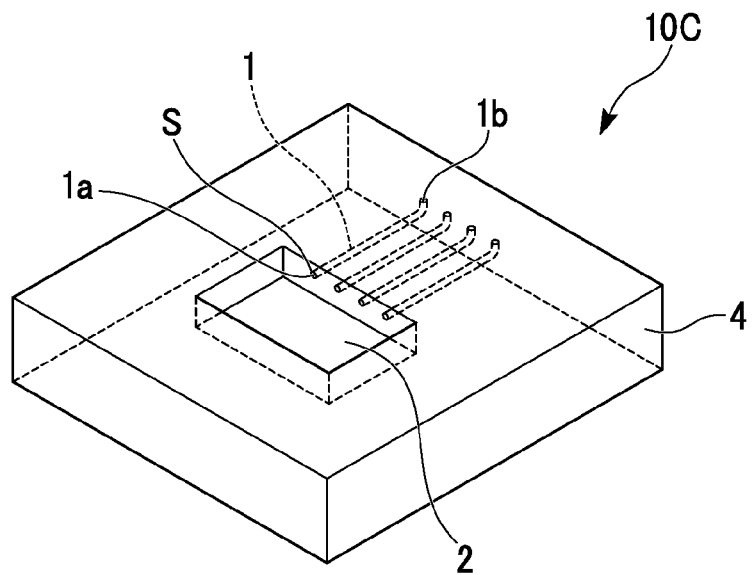
FIG. 5 is a schematic perspective view showing an example of the base body for trapping microorganisms or cells according to the invention.

An embodiment of the base body for trapping microorganisms or cells of the invention is also shown in a base body 10C of FIG. 5.

In the base body 10C, the second end portions 1b of the fine vacuum holes 1 are provided on the top surface side of the base member 4.

That is, the second end portions 1b of the fine vacuum holes 1 can be provided on an arbitrary surface in addition to the side surface of the base member 4.

Other configurations of the base body 10C are the same as in the base body 10A.

[Base Body 10D]

Figure 6:
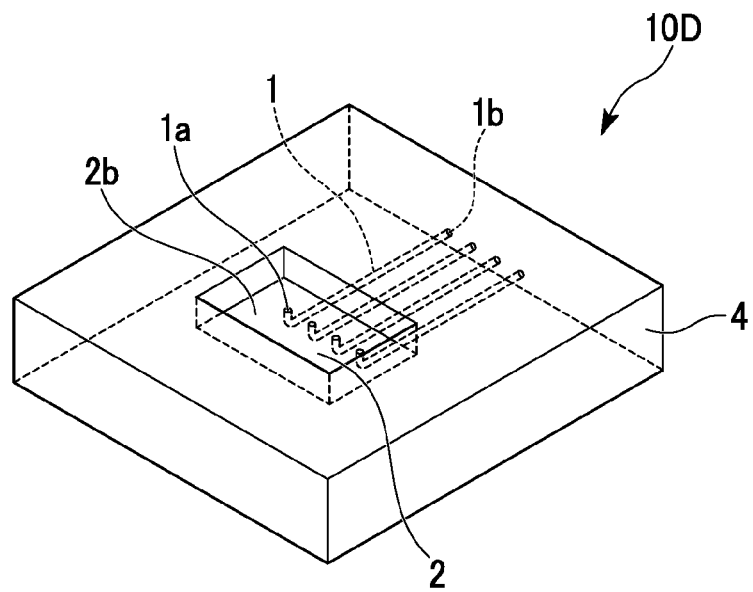
FIG. 6 is a schematic perspective view showing an example of the base body for trapping microorganisms or cells according to the invention.

An embodiment of the base body for trapping microorganisms or cells of the invention is also shown in a base body 10D of FIG. 6.

In the base body 10D, the adsorption portions including the first end portions 1a of the fine vacuum holes 1 are provided on the bottom surface 2b of the well 2.

That is, the first end portions 1a of the fine vacuum holes 1 can be provided on an arbitrary surface in addition to the side surface of the well 2 that configures the space.

In a case in which the adsorption portions are provided on the bottom surface (base surface) of the space, there is an advantage of easy trapping of microorganisms or cells included in the fluid R when the microorganisms or cells are heavy and thus settle.

Other configurations of the base body 10D are the same as in the base body 10A.

[Base Body 10E]

Figure 7:
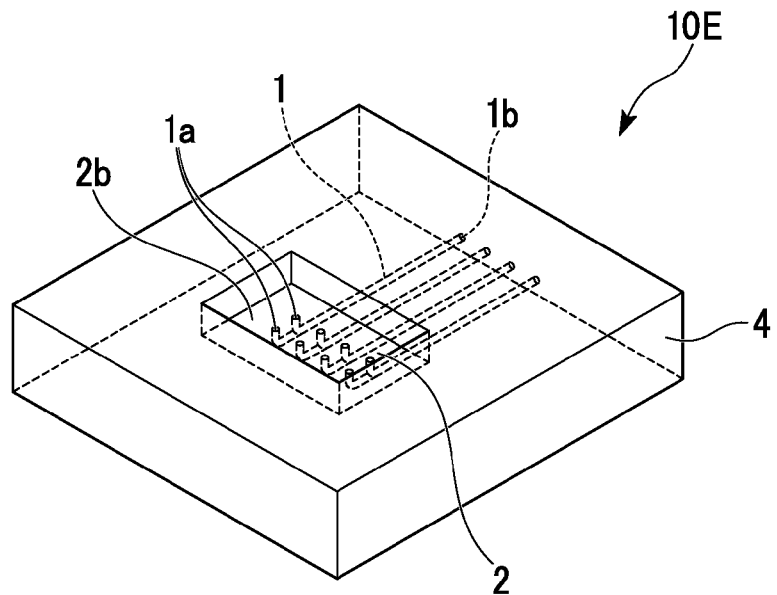
FIG. 7 is a schematic perspective view showing an example of the base body for trapping microorganisms or cells according to the invention.

An embodiment of the base body for trapping microorganisms or cells of the invention is also shown in a base body 10E of FIG. 7.

In the base body 10E, the first end portions 1a of the fine vacuum holes 1 are provided on the bottom surface 2b of the well 2.

At this time, the first end portion 1a of each of the fine vacuum holes 1 is branched into two parts so that twice as many of the adsorption portions are formed on the bottom surface 2b of the well 2 as the second end portions 1b.

That is, the first end portions 1a of the fine vacuum holes 1 may be branched and opened at a plurality of locations in the space.

This configuration can dispose a number of adsorption portions in the space, which is capable of trapping a larger number of microorganisms or cells.

In addition, it is possible to dispose as many of the first end portions 1a as desired apart from the same number of or twice as many as the second end portions 1b.

Other configurations of the base body 10E are the same as in the base body 10A.

[Base Body 10F]

Figure 8:
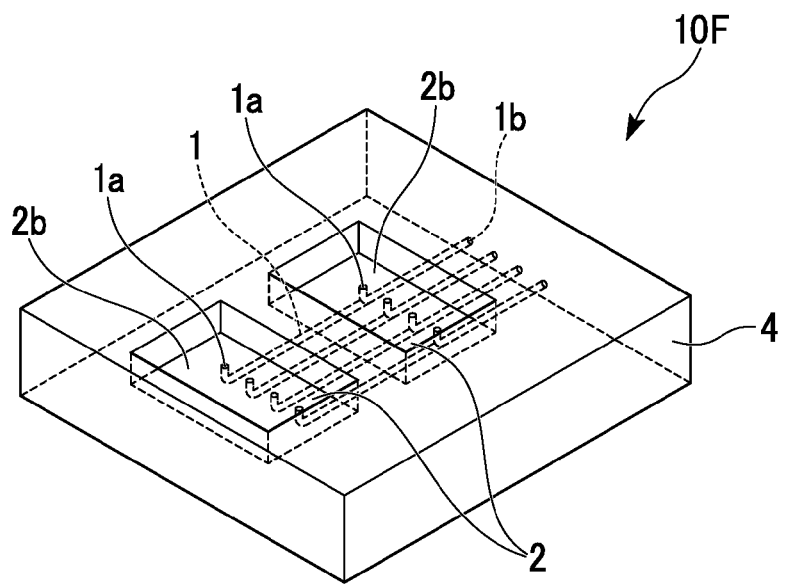
FIG. 8 is a schematic perspective view showing an example of the base body for trapping microorganisms or cells according to the invention.

An embodiment of the base body for trapping microorganisms or cells of the invention is also shown in a base body 10F of FIG. 8.

In the base body 10F, two wells 2 are disposed on the top surface of the base member 4, and the branched first end portions 1a of the fine vacuum holes 1 are disposed in each of the wells 2.

Since the configuration having two wells 2 can allow a fluid R that is different from the fluid in the well 1 to flow into the respective wells 2, the configuration is suitable for a multi-detection subject treatment.

The number of the wells 2 is not limited to 1 or 2, and as many as desired can be disposed.

Other configurations of the base body 10F are the same as in the base body 10A.

[Base Body 10G]

Figure 9:
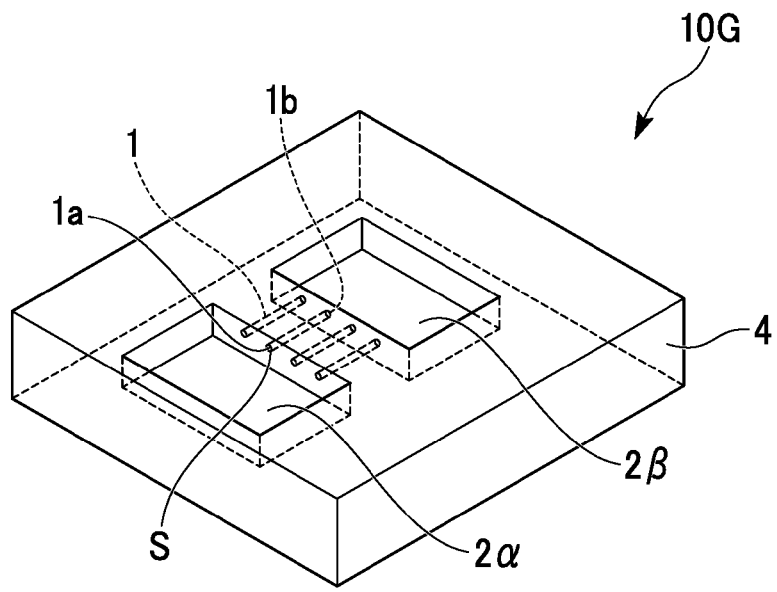
FIG. 9 is a schematic perspective view showing an example of the base body for trapping microorganisms or cells according to the invention.

An embodiment of the base body for trapping microorganisms or cells of the invention is also shown in a base body 10G of FIG. 9.

In the base body 10G; two wells 2α and 2β are disposed on the top surface of the base member 4, and the first end portions 1a and the second end portions 1b of the fine vacuum holes 1 are disposed respectively on the side surfaces of the respective wells 2.

In this case, the fluid R including microorganisms or cells is made to flow into the wells 2α to which the first end portions 1a are open.

In contrast to the above, the sucking portions are directly or indirectly connected separately to the wells 2β to which the second end portions 2b are open.

In this case, it is possible to pull the fluid R which has flowed into the well 2α to the well 2β by forming a negative pressure in the well 2β.

At this time, it is possible to trap the microorganisms or cells in the fluid R at the adsorption portions S including the first end portions 1a which are open to the side surface of the well 2α.

That is, it is also possible to provide the second end portions 1b of the fine vacuum holes 1 on the side surface of a recess portion (well 2β) provided on the top surface of the base member 4 as described above in addition to on the side surface or one surface of the base member.

In addition, the number of the wells is not limited to 2, and as many as desired can be disposed.

Other configurations of the base body 10G are the same as in the base body 10A.

It is not a definite requirement that the wells 2 or the fluidic channel 3 in the base bodies 10A to 10G have no lid, and a lid may be appropriately provided (not shown).

When a lid is provided, there are cases in which it becomes easy to hold the fluid R in the well 2, or the circularity of the fluid R in the fluidic channel 3 is enhanced.

[Base Body 10H]

Figure 10:
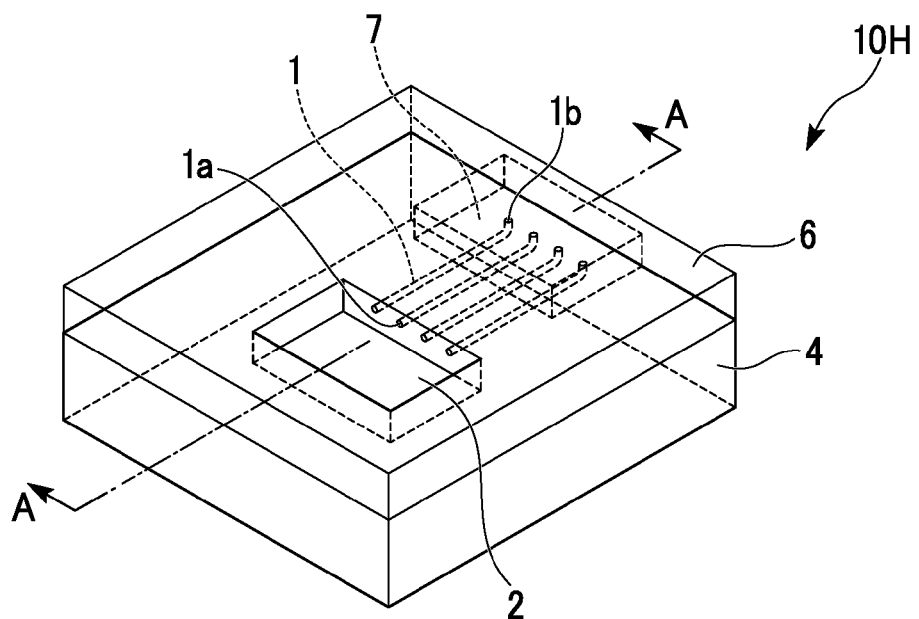
FIG. 10 is a schematic perspective view showing an example of the base body for trapping microorganisms or cells according to the invention.

An embodiment of the base body for trapping microorganisms or cells of the invention is also shown in a base body 10H of FIG. 10.

Figure 11:
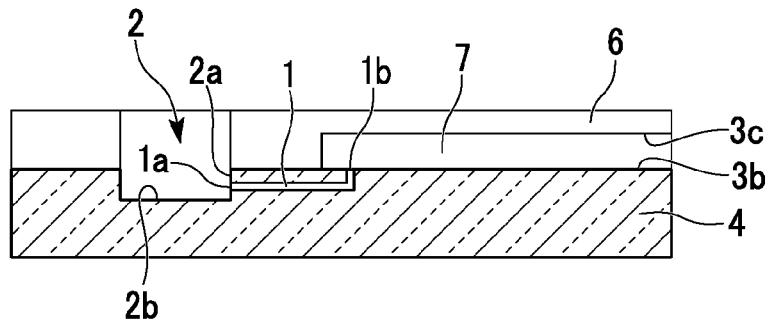
FIG. 11 is a cross-sectional view taken along the line A-A in FIG. 10.
Figure 12:
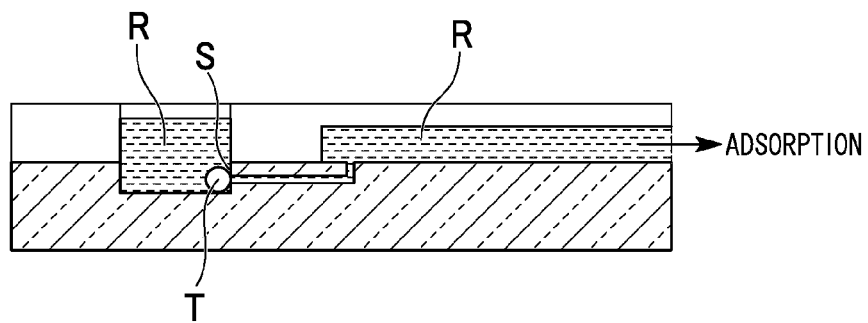
FIG. 12 is a schematic view showing an appearance in which a microorganism or cell is trapped at the adsorption portion in the cross-sectional view of FIG. 11.

FIGS. 11 and 12 are schematic views showing the cross-section taken along the line A-A in FIG. 10.

The base body 10H is formed by adhering a substrate 6 to the top surface of the base member 4 in the configuration of the above base body 10C.

The well 2 is provided on the top surface of the base member 4.

In the substrate 6, a location opposite to the well 2 is hollowed out, penetrated, and opened to the top surface.

According to the above configuration, it is possible to increase the volume of the well 2 as much as the thickness of the substrate 6, and the amount of the fluid R which flows into the well can be increased.

In addition, the second end portions 1b of the fine vacuum holes 1 are disposed on the top surface of the base member 4.

In the substrate 6, a fluidic channel 7 is provided at a location opposite to the second end portions 1b.

According to the above configuration, it is possible to pull and suction the fluid R in the well 2 to the fluidic channel 7 through the fine vacuum holes 1 by directly or indirectly connecting the adsorption portions to the fluidic channel 7.

At this time, the microorganisms or cells in the fluid R can be trapped at the adsorption portions S.

In a case in which the substrate 6 is formed of a transparent member, observation is possible from any of the top surface side and the bottom surface side.

Other configurations of the base body 10H are the same as in the base body 10A.

The material of the substrate 6 is not particularly limited, and examples thereof include resin substrates such as PDMS and PMMA, silicon substrates, and glass substrates.

In a case in which the substrate is formed of the same material as for the base member 4, it is possible to easily adhere the substrate and the base member.

The base member 4 and the substrate 6 may be adhered using a well-known method.

[Base Body 10I]

Figure 13:
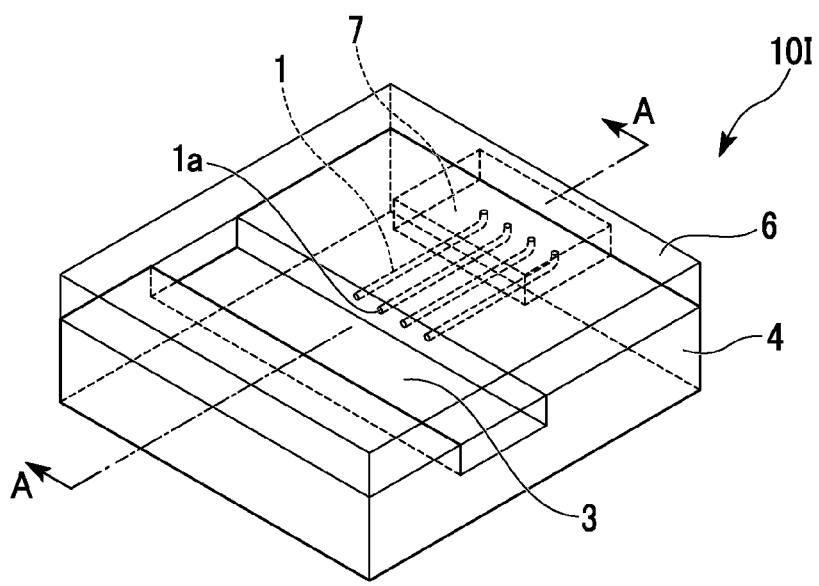
FIG. 13 is a schematic perspective view showing an example of the base body for trapping microorganisms or cells according to the invention.

An embodiment of the base body for trapping microorganisms or cells of the invention is also shown in a base body 10I of FIG. 13.

Figure 14:
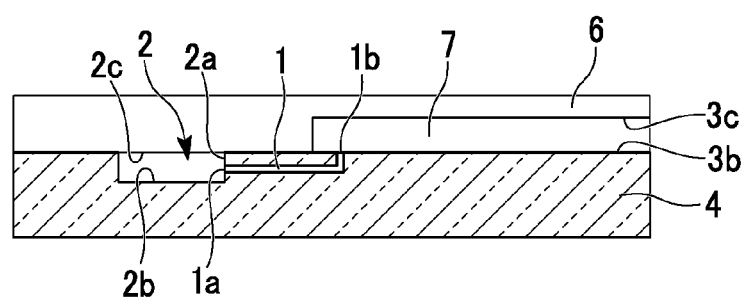
FIG. 14 is a cross-sectional view taken along the line A-A in FIG. 13.
Figure 15:
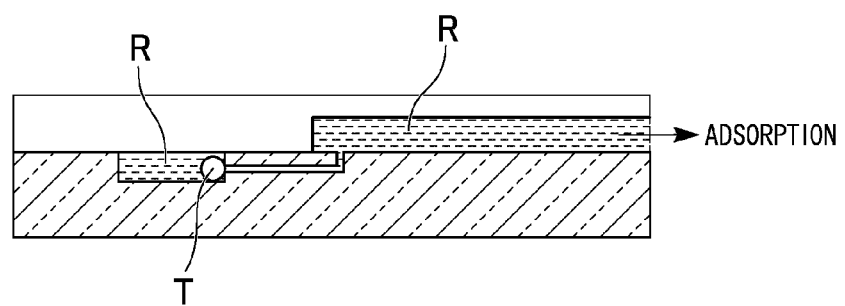
FIG. 15 is a schematic view showing an appearance in which a microorganism or cell is trapped at the adsorption portion in the cross-sectional view of FIG. 13.

FIGS. 14 and 15 are schematic views showing the cross-section taken along the line A-A in FIG. 13.

The base body 10I is formed by adhering the substrate 6 to the top surface of the base member 4 in the configuration of the above base body 10B.

The fluidic channel 3 is provided on the top surface of the base member 4.

According to the above configuration, only a necessary amount of the fluid R is allowed to flow into and circulate in the fluidic channel 3.

In addition, the second end portions 1b of the fine vacuum holes 1 are disposed on the top surface of the base member 4.

In the substrate 6, the fluidic channel 7 is provided at a location opposite to the second end portions 1b.

According to the above configuration, it is possible to pull and suction the fluid R in the fluidic channel 3 to the fluidic channel 7 through the fine vacuum holes 1 by directly or indirectly connecting the adsorption portions to the fluidic channel 7.

At this time, the microorganisms or cells in the fluid R can be trapped at the adsorption portions S.

Other configurations of the base body 10I are the same as in the base body 10B.

The material of the substrate 6 is not particularly limited, and examples thereof include resin substrates such as PDMS and PMMA, silicon substrates, and glass substrates.

In a case in which the substrate is formed of the same material as for the base member 4, it is possible to easily adhere the substrate and the base member.

The base member 4 and the substrate 6 may be adhered using a well-known method.

A Second Embodiment of the Base Body for Trapping Microorganisms or Cells

Figure 16:
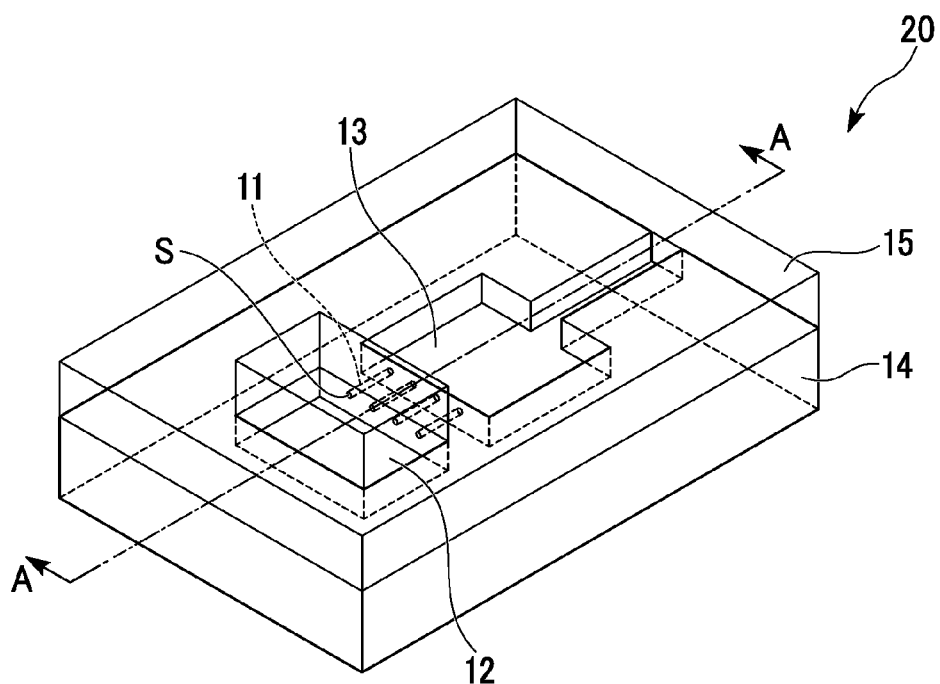
FIG. 16 is a schematic perspective view showing an example of the base body for trapping microorganisms or cells according to the invention.

FIG. 16 is a perspective view of a base body 20 which is a second embodiment of the base body for trapping microorganisms or cells according to the invention.

Figure 17:
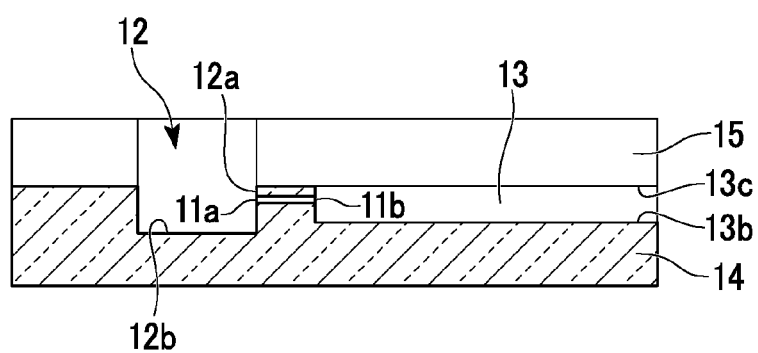
FIG. 17 is a cross-sectional view taken along the line A-A in FIG. 1.
Figure 18:
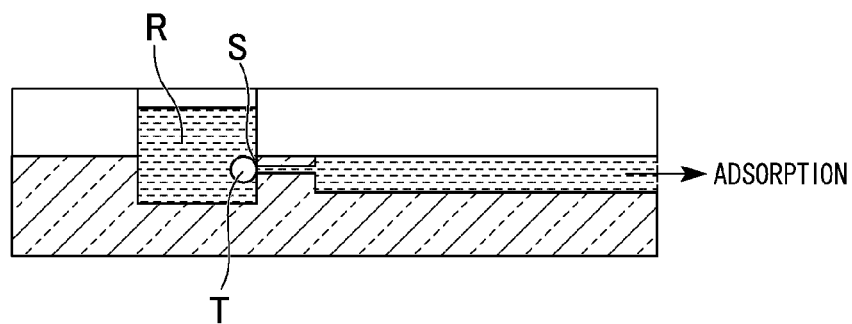
FIG. 18 is a schematic view showing an appearance in which a microorganism or cell body is trapped at the adsorption portion in the cross-sectional view of FIG. 2.

FIGS. 17 and 18 are schematic views showing the cross-section taken along the line A-A in FIG. 16.

The base body 20 is a base body for trapping microorganisms or cells having fine vacuum holes 11 that trap microorganisms or cells T.

The base body 20 has at least a well 12 that configures a space present in a base member 14 which allows the fluid R including microorganisms or cells T to flow in, a first fluidic channel 13 in which a negative pressure can be formed, and the fine vacuum holes 11 that communicate the well 12 and the first fluidic channel 13.

The fine vacuum holes 11 are communicated to the outside of the base member 14 through the first fluidic channel 13.

The adsorption portions S at which first end portions 11a of the fine vacuum holes 11 are exposed are formed on a side surface 12a of the well 12.

At least some of a top surface or bottom surface 12b of the well 12 is opened or constituted by a transparent member (not shown) so that the microorganisms or cells T trapped at the adsorption portions S can be optically observed.

At least portions that configure the fine vacuum holes 11 in the base member 14 are formed of a single member.

In the base body 20 shown in FIG. 16, the single member configures not only the fine vacuum holes 11 but also the entire base member 14.

Examples of the material of the single member include silicon, glass, silica, sapphire, and the like.

The above materials are excellent in terms of the workability of the fine vacuum holes 11, which is preferable.

Among the above, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the above laser light is transmitted, it is possible to form modified regions by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIG. 16, the single member that configures the base member 14 is a transparent glass substrate.

As shown in FIGS. 17 and 18, the fine vacuum holes 11 communicate the well 12 to the first fluidic channel 13.

First end portions 11a of the fine vacuum holes 11 are exposed (opened) at the side surface 12a of the well 12, and form the adsorption portions S.

Second end portions 11b of the fine vacuum holes 11 are exposed at a side surface of the first fluidic channel 13.

The fine vacuum holes 11 are formed in the single glass substrate 4, and are through holes having no seam or adhered surface.

Naturally, there is no seam or adhered surface in the adsorption portions S at the end portion of the fine vacuum holes.

Here, the "adsorption portion S" refers to an area which the microorganisms or cells T come into contact with or come close to in the side surface 12a of the well 12.

The shape of the first end portions 11a of the fine vacuum holes 11 which configure the adsorption portions S at the side surface 12a of the well 12 may be any of rectangular, triangular, oval, and circular.

It is possible to trap the microorganisms or cells T as long as the minor axis (the diameter of the shortest opening portion) of the hole is in a range of 0.02 μm to 5 μm.

Even in the above range, the minor axis is preferably in a range of 0.02 μm to 0.8 μm for microorganisms that are smaller than the cells.

That is, the minor axis of the hole needs to be sufficiently small such that the microorganisms or cells T cannot pass through the fine vacuum holes 11.

For example, in the case of trapping red blood cells (6 μm to 8 μm), the minor axis needs to be approximately 1 μm, and, in the case of trapping natto bacilli (grass bacilli; 0.7 μm to 2 μm), the minor axis needs to be approximately 0.2 μm.

The range of the minor axis is preferably 0.02 μm to 2 μm.

When the diameter is less than the lower limit value of the range, there is a concern that the suctioning force at the adsorption portion S may be too weak such that it is not possible to trap the microorganisms or cells T.

When the diameter exceeds the upper limit value of the range, there is a concern that the microorganisms or cells T may pass through the fine vacuum holes 11 and may not be able to be trapped.

On the other hand, the major axis (the diameter of the longest opening portion) of the hole may be appropriately adjusted depending on the size of the microorganisms or cells T to be trapped, and is in a range of, for example, 0.2 μm to 10 μm.

In FIGS. 17 and 18, the fine vacuum holes 11 are formed substantially perpendicularly with respect to the side surface 12a of the well 12.

However, the fine vacuum holes do not necessarily need to be substantially perpendicular to the side surface, and can be freely disposed in a single glass substrate 14 in accordance with the design of the base body 20.

A plurality of fine vacuum holes 11 may be disposed in the base body 20.

Since each of the fine vacuum holes 11 has the adsorption portion S, it is possible to trap a plurality of microorganisms or cells T.

The bottom surface 12b of the well 12 is constituted by the glass substrate 14.

The top surface of the well 12 which is opposite to the bottom surface 12b is opened, and has no lid.

Therefore, it is possible to optically observe the microorganisms or cells T trapped at the adsorption portions S from the bottom surface 12b or top surface using a microscope or the like.

Meanwhile, it is not a definite requirement that the top surface have no lid, and the top surface may be covered with a lid including a member such as a plastic, resin, or glass member (not shown).

A bottom surface 13b of the first fluidic channel 13 is constituted by the glass substrate 14, and a top surface 13c of the first fluidic channel 13 is constituted by a member 15 such as a plastic or glass member.

Thereby, the first fluidic channel 13 forms a space in a half-sealed state.

The second end portions 11b of the fine vacuum holes 11 are exposed and opened on the upstream of the first fluidic channel 13.

A negative pressure portion such as a syringe or a pump which can form a negative pressure in the first fluidic channel 13 is provided on the downstream of the first fluidic channel 13 (not shown).

Therefore, the fluid R which has flowed in from the top surface of the well 12 is pulled into the first fluidic channel 13 through the fine vacuum holes 11 by forming a negative pressure in the first fluidic channel 13.

At this time, it is possible to draw and trap the microorganisms or cells T included in the fluid R at the adsorption portions S configured at the first end portions 11a of the fine vacuum holes 1 (FIG. 18).

As shown in FIGS. 17 and 18, some of the side surface 12a of the well 12 may be constituted by the member 15.

Thereby, it is possible to appropriately adjust the depth of the well 12 using the thickness of the member 15.

For example, it is possible to deepen the well 12 by laminating a plurality of members 15.

Figure 19:
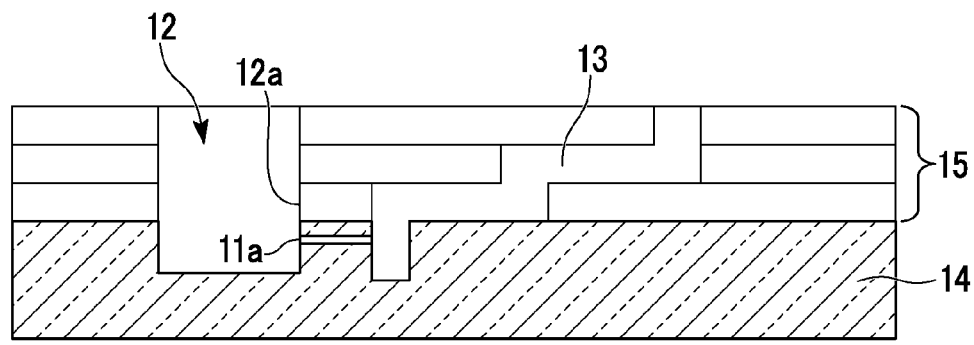
FIG. 19 is a schematic perspective view showing an example of the base body for trapping microorganisms or cells according to the invention.

Furthermore, as shown in FIG. 19, it is also possible to dispose the downstream of the first fluidic channel 13 on the top surface of the base body 20 using the height (thickness) of the laminated members 15.

The material of the member 15 is not particularly limited, and it is possible to use a resin substrate such as PDMS or PMMA, or a glass substrate.

The member that configures the side surface 12a of the well 12 and the top surface 13c of the first fluidic channel 13 may be constituted by a material that does not transmit light (for example, visible light) used for observation.

In a case in which trapping of microorganisms or cells is the only object, it is not necessarily required to transmit light that are used for observation.

When a member that transmits light used for observation is used, optical observation from the top surface becomes possible, which is preferable.

Figure 20:
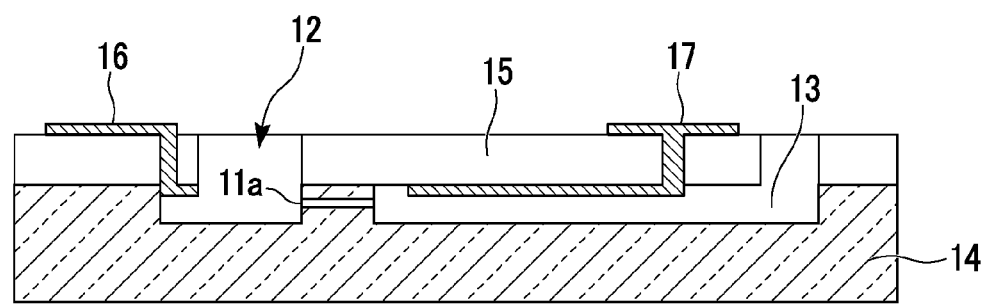
FIG. 20 is a cross-sectional view showing an example of the base body for trapping microorganisms or cells according to the invention.

In a case in which an electrophysiological measurement of the trapped microorganisms or cells T is conducted, for example, it is possible to dispose electrodes 16 and 17 respectively in the well 12 and the first fluidic channel 13 as shown in FIG. 20.

Alternatively, it is possible to carry out an electrophysiological measurement using external electrodes through an extracellular buffer, an intracellular fluid, or the like.

Since the adsorption portion S is formed of the single glass substrate 14, it is possible to form high resistance sealing with respect to the cell membranes of the cells T.

Therefore, the well-known patch-clamp method of the related art can be applied.

At this time, it is possible to carry out a more highly accurate electrophysiological measurement than in the related art by making the diameters of the openings of the holes including the first end portions 11a of the fine vacuum holes 11 that configure the adsorption portions S be smaller than the diameter of the opening (approximately 2 μm to 4 μm) of the hole of a patch pipet or the like of the related art.

The electrodes 16 and 17 may be disposed in a separate fluidic channel that is communicated to the well 12 and the first fluidic channel 13, for example, at least one of a fourth fluidic channel and a fifth fluidic channel described below.

A Third Embodiment of the Base Body for Trapping Microorganisms or Cells

Figure 21:
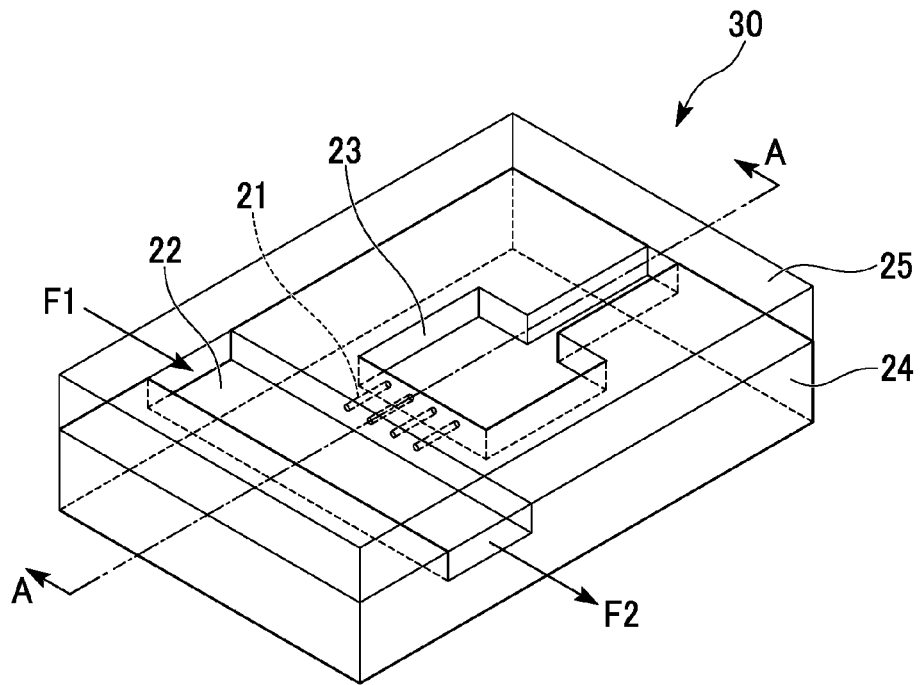
FIG. 21 is an outline perspective view showing an example of the base body for trapping microorganisms or cells according to the invention.

FIG. 21 is a perspective view of a base body 30 which is the third embodiment of the base body for trapping microorganisms or cells according to the invention.

Figure 22:
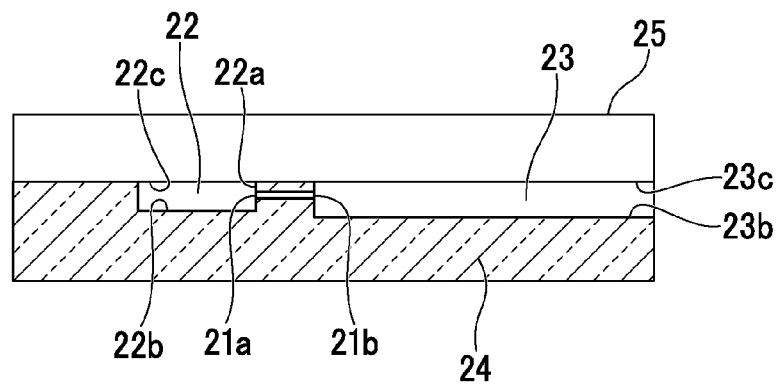
FIG. 22 is a cross-sectional view taken along the line A-A in FIG. 6.
Figure 23:
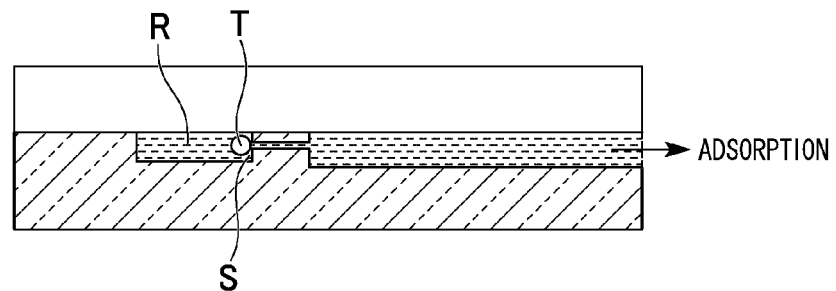
FIG. 23 is a schematic view showing an appearance in which a microorganism or cell body is trapped at the adsorption portion in the cross-sectional view of FIG. 7.

FIGS. 22 and 23 are schematic views showing the cross-section taken along the line A-A in FIG. 21.

The base body 30 is a base body for trapping microorganisms or cells having fine vacuum holes 21 that trap microorganisms or cells T.

The base body 30 has at least a second fluidic channel 22 that configures a space present in a base member 24 which allows the fluid R including microorganisms or cells T to flow in, a third fluidic channel 23 in which a negative pressure can be formed, and the fine vacuum holes 21 that communicate the second fluidic channel 22 and the third fluidic channel 23.

The fine vacuum holes 21 are communicated to the outside of the base member 24 through a first fluidic channel 23.

The adsorption portions S at which first end portions 21a of the fine vacuum holes 21 are exposed are formed on a side surface 22a of the second fluidic channel 22, and at least some of a top surface 22c or a bottom surface 22b of the second fluidic channel 22 is constituted by a transparent member 25 so that the microorganisms or cells T trapped at the adsorption portions S can be optically observed.

At least portions that configure the fine vacuum holes 21 in the base member 24 are formed of a single member.

In the base body 30 shown in FIG. 21, the single member configures not only the fine vacuum holes 21 but also the entire base member 24.

Examples of the material of the single member include silicon, glass, silica, sapphire, and the like.

The above materials are excellent in terms of the workability of the fine vacuum holes 21, which is preferable.

Among the above, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the material of the single member transmits the above laser light, it is possible to form modified regions by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIG. 21, the single member that configures the base member 24 is a transparent glass substrate.

As shown in FIGS. 22 and 23, the fine vacuum holes 21 communicate the second fluidic channel 22 and the third fluidic channel 23.

The first end portions 21a of the fine vacuum holes 21 are exposed (opened) at the side surface 22a of the second fluidic channel 22, and form the adsorption portions S.

The second end portions 21b of the fine vacuum holes 21 are exposed at a side surface of the third fluidic channel 23.

The fine vacuum holes 21 are formed in the single glass substrate 24, and are through holes having no seam or adhered surface.

Naturally, there is no seam or adhered surface in the adsorption portions S at the end portion of the fine vacuum holes.

Here, the "adsorption portion S" refers to an area which the microorganisms or cells T come into contact with or come close to in the side surface 22a of the second fluidic channel 22.

The shape of the first end portions 21a of the fine vacuum holes 21 which configure the adsorption portions S at the side surface 22a of the second fluidic channel 22 may be any of a rectangle, a triangle, an oval, and a circle.

It is possible to trap the microorganisms or cells T as long as the minor axis (the diameter of the shortest opening portion) of the hole is in a range of 0.02 μm to 5 μm.

Even in the above range, the minor axis is preferably in a range of 0.02 μm to 0.8 μm for microorganisms that are smaller than the cells.

That is, the minor axis of the hole needs to be sufficiently small such that the microorganisms or cells T cannot pass through the fine vacuum holes 21.

For example, in the case of trapping red blood cells (6 μm to 8 μm), the minor axis needs to be approximately 1 μm, and, in the case of trapping natto bacilli (grass bacilli; 0.7 μm to 2 μm), the minor axis needs to be approximately 0.2 μm.

The range of the minor axis is preferably 0.02 μm to 2 μm.

When the diameter is less than the lower limit value of the range, there is a concern that the sucking force at the adsorption portion S may be too weak such that it is not possible to trap the microorganisms or cells T.

When the diameter exceeds the upper limit value of the range, there is a concern that the microorganisms or cells T may pass through the fine vacuum holes 21 and may not be able to be trapped.

On the other hand, the major axis (the diameter of the longest opening portion) of the hole may be appropriately adjusted depending on the size of the microorganisms or cells T to be trapped, and is in a range of, for example, 0.2 μm to 10 μm.

In FIGS. 22 and 23, the fine vacuum holes 21 are formed substantially perpendicularly with respect to the side surface 22a of the second fluidic channel 22.

However, the fine vacuum holes do not necessarily need to be substantially perpendicular to the side surface, and can be freely disposed in a single glass substrate 24 in accordance with the design of the base body 30.

A plurality of fine vacuum holes 21 may be disposed in the base body 30.

Since each of the fine vacuum holes 21 has the adsorption portion S, it is possible to trap a plurality of microorganisms or cells T.

The bottom surface 22b of the second fluidic channel 22 is constituted by the glass substrate 24.

The top surface 22c of the second fluidic channel 22 which is opposite to the bottom surface 22b is constituted by a member 25 such as plastic or glass.

It is possible to optically observe the microorganisms or cells T trapped at the adsorption portions S from the top surface 22c or bottom surface 22b using a microscope or the like.

A bottom surface 23b of the third fluidic channel 23 is constituted by the glass substrate 24, and a top surface 23c of the third fluidic channel 23 is constituted by the member 25.

Thereby, the third fluidic channel 23 forms a space in a half-sealed state.

The second end portions 21b of the fine vacuum holes 21 are exposed and opened on the upstream of the third fluidic channel 23.

A negative pressure portion such as a syringe or a pump which can form a negative pressure in the third fluidic channel 23 is provided on the downstream of the third fluidic channel 23 (not shown).

Therefore, some of the fluid R which has flowed into a downstream F2 of the second fluidic channel 22 from an upstream F1 of the second fluidic channel 22 is pulled into the third fluidic channel 23 through the fine vacuum holes 21 by forming a negative pressure in the third fluidic channel 23.

At this time, it is possible to draw and trap the microorganisms or cells T included in the fluid R at the adsorption portions S configured at the first end portions 21a of the fine vacuum holes 21 (FIG. 23).

Figure 24:
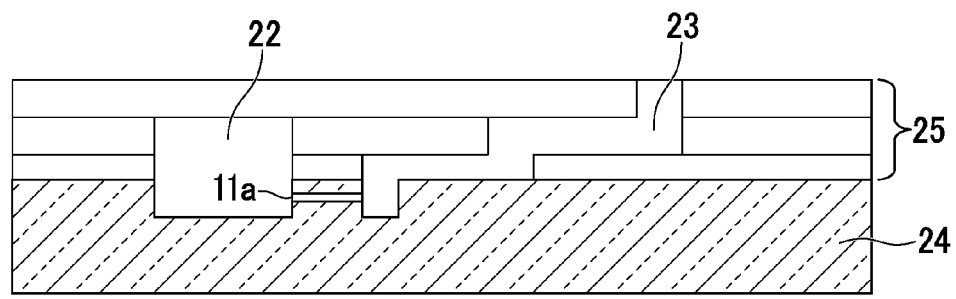
FIG. 24 is a cross-sectional view showing an example of the base body for trapping microorganisms or cells according to the invention.

As shown in FIG. 24, some of the side surface 22a of the second fluidic channel 22 may be constituted by the member 25.

Thereby, it is possible to appropriately adjust the flow rate of the fluid R at the second fluidic channel 22 using the thickness of the member 25.

For example, it is possible to increase the diameter of the second fluidic channel 22 by laminating a plurality of members 25.

Furthermore, it is also possible to dispose the downstream of the third fluidic channel 23 on the top surface of the base body 30 using the height (thickness) of the laminated members 25.

The material of the member 25 is not particularly limited, and it is possible to use a resin substrate such as PDMS or PMMA, or a glass substrate.

The member that configures the top surface 23c of the third fluidic channel 23 may be constituted by a material that does not transmit light (for example, visible light) used for observation.

In a case in which trapping of microorganisms or cells is the only object, the member does not necessarily need to transmit light that is used for observation.

When a member that transmits light used for observation is used, optical observation from the top surface becomes possible, which is preferable.

Figure 25:
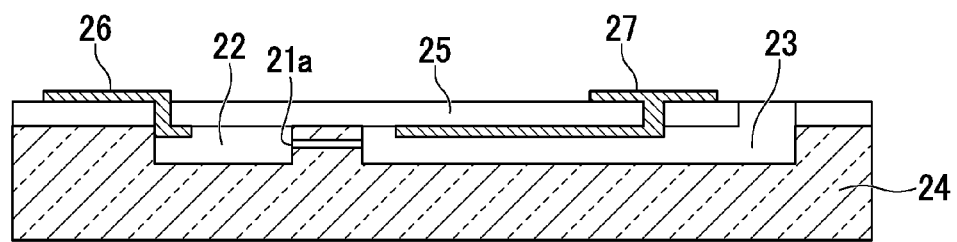
FIG. 25 is a cross-sectional view showing an example of the base body for trapping microorganisms or cells according to the invention.

In a case in which an electrophysiological measurement of the trapped microorganisms or cells T is conducted, for example, it is possible to dispose electrodes 26 and 27 respectively in the second fluidic channel 22 and the third fluidic channel 23 as shown in FIG. 25.

Alternatively, it is possible to carry out an electrophysiological measurement using external electrodes through an extracellular buffer, an intracellular fluid, or the like.

Since the adsorption portion S is formed of the single glass substrate 24, it is possible to form high resistance sealing with respect to the cell membranes of the cells T.

Therefore, the well-known patch-clamp method of the related art can be applied.

At this time, it is possible to carry out a more highly accurate electrophysiological measurement than in the related art by making the diameters of the openings of the holes including the first end portions 21a of the fine vacuum holes 21 that configure the adsorption portions S be smaller than the diameter of the opening (approximately 2 μm to 4 μm) of the hole of a patch pipet or the like of the related art.

The electrodes 26 and 27 may be disposed in a separate fluidic channel that is communicated to the second fluidic channel 22 and the third fluidic channel 23, for example, at least one of a fourth fluidic channel and a fifth fluidic channel described below.

In the base body 30 of the third embodiment, the second fluidic channel 22 is employed instead of the well 12 in the base body 20 of the second embodiment.

Since it is possible to continuously circulate the fluid R in the second fluidic channel 22, compared to a case in which the well 22 is employed, it becomes possible to allow the available fluid R to continuously flow without stopping.

A Fourth Embodiment of the Base Body for Trapping Microorganisms or Cells

Figure 26:
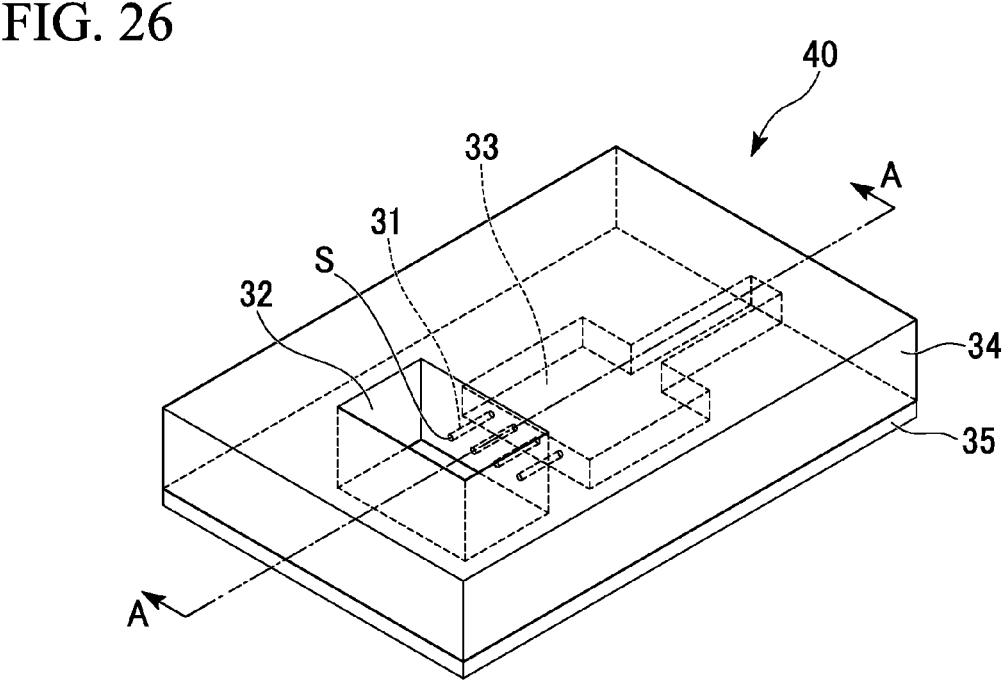
FIG. 26 is an outline perspective view showing an example of the base body for trapping microorganisms or cells according to the invention.

FIG. 26 is a perspective view of a base body 40 which is the fourth embodiment of the base body for trapping microorganisms or cells according to the invention.

Figure 27:
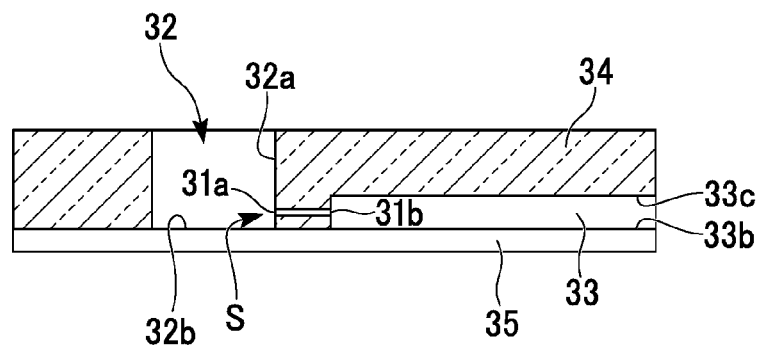
FIG. 27 is a cross-sectional view taken along the line A-A in FIG. 11.

FIG. 27 is a schematic view showing the cross-section taken along the line A-A in FIG. 26.

The base body 40 is a base body for trapping microorganisms or cells having fine vacuum holes 31 that trap microorganisms or cells T.

The base body 40 has at least a well 32 that configures a space present in a base member 34 which allows the fluid R including microorganisms or cells T to flow in, a first fluidic channel 33 in which a negative pressure can be formed, and the fine vacuum holes 31 that communicate the well 32 and the first fluidic channel 33.

The fine vacuum holes 31 are communicated to the outside of the base member 34 through the first fluidic channel 33.

The adsorption portions S at which first end portions 31a of the fine vacuum holes 31 are exposed are formed on a side surface 32a of the well 32, and at least some of a top surface or a bottom surface 32b of the well 32 is opened or constituted by a transparent member 35 so that the microorganisms or cells T trapped at the adsorption portions S can be optically observed.

At least portions that configure the fine vacuum holes 31 in the base member 34 are formed of a single member.

In the base body 40 shown in FIG. 26, the single member configures not only the fine vacuum holes 31 but also the entire base member 34.

Examples of the material of the single member include silicon, glass, silica, sapphire, and the like.

The above materials are excellent in terms of the workability of the fine vacuum holes 31, which is preferable.

Among the above, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the above laser light is transmitted, it is possible to form modified regions by irradiating, with the laser, the member as described below.

In addition, the single member more preferably transmits light in the visible light range (approximately 0.36 μm to approximately 0.83 μm).

It is possible to easily observe the trapped microorganisms or cells T visually through the single member by transmitting light in the visible light range.

Meanwhile, in the invention, the "transmission (being transparent)" refers to everything about a state in which transmitted light is obtained from the member by entering light into the member.

In FIG. 26, the single member that configures the base member 34 is a transparent glass substrate.

As shown in FIG. 27, the fine vacuum holes 31 communicate the well 32 and the first fluidic channel 33.

The first end portions 31a of the fine vacuum holes 31 are exposed (opened) at the side surface 32a of the well 32, and form the adsorption portions S.

The second end portions 31b of the fine vacuum holes 31 are exposed at a side surface of the first fluidic channel 33.

The fine vacuum holes 31 are formed in the single glass substrate 34, and are through holes having no seam or adhered surface.

Naturally, there is no seam or adhered surface in the adsorption portions S at the end portion of the fine vacuum holes.

Here, the "adsorption portion S" refers to an area which the microorganisms or cells T come into contact with or come close to in the side surface 32a of the well 32.

The shape of the first end portions 31a of the fine vacuum holes 31 which configure the adsorption portions S at the side surface 32a of the well 32 may be any of a rectangle, a triangle, an oval, and a circle.

The description of the minor axis (the diameter of the shortest opening) and major axis (the diameter of the longest opening) of the hole is the same as the description of the hole in the base body 20 of the second embodiment.

In FIG. 27, the fine vacuum holes 31 are formed substantially perpendicularly with respect to the side surface 32a of the well 32.

However, the fine vacuum holes do not necessarily need to be substantially perpendicular to the side surface, and can be freely disposed in a single glass substrate 34 in accordance with the design of the base body 40.

A plurality of fine vacuum holes 31 may be disposed in the base body 40.

Figure 28:
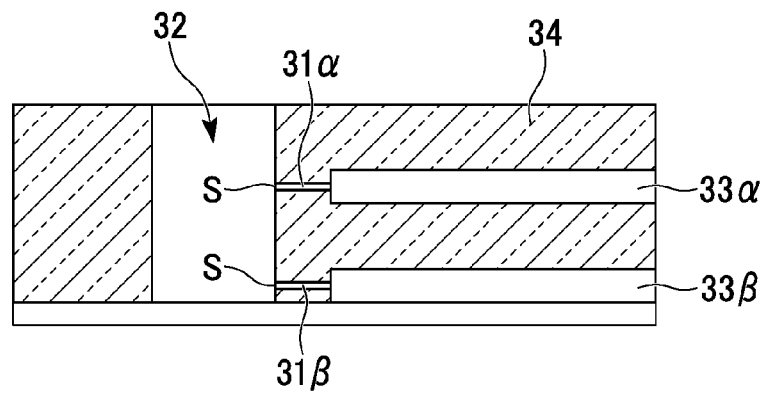
FIG. 28 is a cross-sectional view showing an example of the base body for trapping microorganisms or cells according to the invention.

For example, a plurality of fine vacuum holes 31 may be disposed in parallel in the height (thickness) direction of the base body 40 as shown in FIG. 28.

In the above example, since each of the fine vacuum holes 31 has the adsorption portion S and one of first fluidic channels 33α and 33β, it is possible to independently control the operations of the respective adsorption portions S, and to trap a plurality of microorganisms or cells T at the respective adsorption portions S.

The bottom surface 32b of the well 32 is constituted by the member 35.

The top surface of the well 32 which is opposite to the bottom surface 32b is opened, and has no lid.

Therefore, it is possible to optically observe the microorganisms or cells T trapped at the adsorption portions S from the bottom surface 32b or top surface using a microscope or the like.

Meanwhile, it is not a definite requirement that the top surface have no lid, and the top surface may be covered with a lid including a member such as a plastic, resin, or glass member (not shown).

A bottom surface 33b of the first fluidic channel 33 is constituted by the member 35 such as a plastic or glass member, and a top surface 33c of the first fluidic channel 33 is constituted by the glass substrate 34.

Thereby, the first fluidic channel 33 forms a space in a half-sealed state.

The second end portions 31b of the fine vacuum holes 31 are exposed and opened on the upstream of the first fluidic channel 33.

A negative pressure portion such as a syringe or a pump which can form a negative pressure in the first fluidic channel 33 is provided on the downstream of the first fluidic channel 33 (not shown).

Therefore, the fluid R which has flowed in from the top surface of the well 32 is pulled into the first fluidic channel 33 through the fine vacuum holes 31 by forming a negative pressure in the first fluidic channel 33.

At this time, it is possible to draw and trap the microorganisms or cells T included in the fluid R at the adsorption portions S configured at the first end portions 31a of the fine vacuum holes 31 (not shown).

The mechanism thereof is the same as in the base body 20 of the second embodiment.

Figure 29:
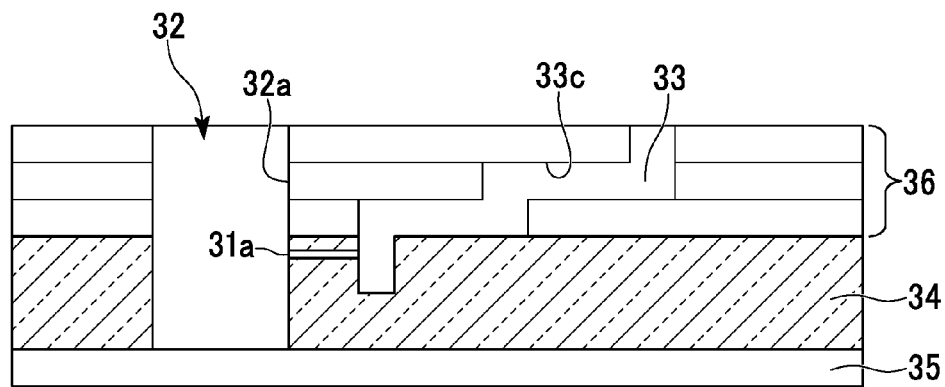
FIG. 29 is a cross-sectional view showing an example of the base body for trapping microorganisms or cells according to the invention.

As shown in FIG. 29, some of the side surface 32a of the well 32 may be constituted by a member 36.

Thereby, it is possible to appropriately adjust the depth of the well 32 using the thickness of the member 36.

For example, it is possible to deepen the well 32 by laminating a plurality of members 36.

Furthermore, it is also possible to dispose the downstream of the first fluidic channel 33 on the top surface of the base body 40 using the height (thickness) of the laminated members 36.

The material of the members 35 and 36 is not particularly limited, and it is possible to use a resin substrate such as PDMS or PMMA, or a glass substrate.

Meanwhile, the member that configures the side surface 32a of the well 32 and the top surface 33c of the first fluidic channel 33 may be constituted by a member that does not transmit light (for example, visible light) used for observation.

In a case in which trapping of microorganisms or cells is the only object, is the member does not necessarily need to transmit light being used for observation.

When a member that transmits light used for observation is used, optical observation from the top surface becomes possible, which is preferable.

In a case in which an electrophysiological measurement of the trapped microorganisms or cells T is conducted, it is possible to dispose electrodes in the well 32, the first fluidic channel 33, and the like and to carry out the measurement in a manner described for the base body 20 of the second embodiment.

A Fifth Embodiment of the Base Body for Trapping Microorganisms or Cells

Figure 30:
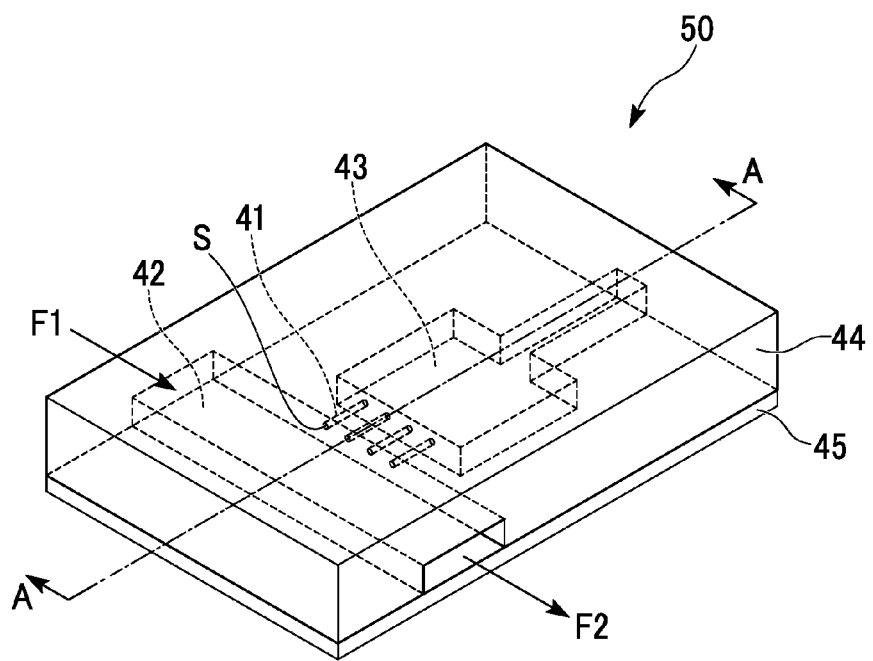
FIG. 30 is an outline perspective view showing an example of the base body for trapping microorganisms or cells according to the invention.

FIG. 30 is a perspective view of a base body 50 which is the fifth embodiment of the base body for trapping microorganisms or cells according to the invention.

Figure 31:
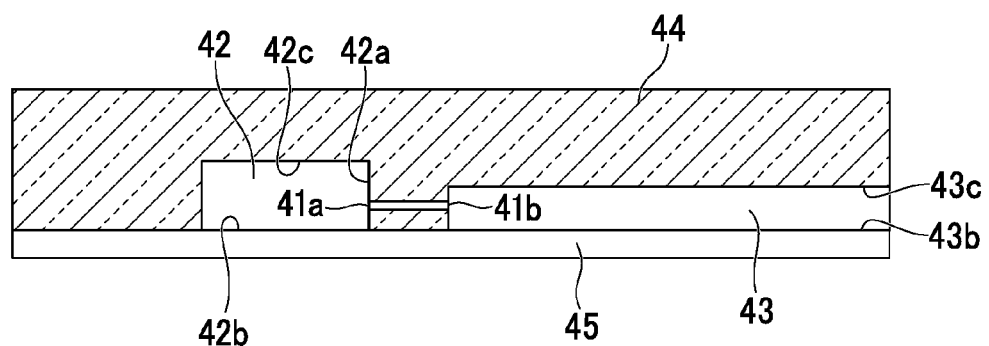
FIG. 31 is a cross-sectional view taken along the line A-A in FIG. 15.

FIG. 31 is a schematic view showing the cross-section taken along the line A-A in FIG. 30.

The base body 50 is a base body for trapping microorganisms or cells having fine vacuum holes 41 that trap microorganisms or cells T.

The base body 50 has at least a second fluidic channel 42 that configures a space present in a base member 44 which allows the fluid R including microorganisms or cells T to flow in, a third fluidic channel 43 in which a negative pressure can be formed, and the fine vacuum holes 41 that communicate the second fluidic channel 42 and the third fluidic channel 43.

The fine vacuum holes 41 are communicated to the outside of the base member 44 through the third fluidic channel 43.

The adsorption portions S at which first end portions 41a of the fine vacuum holes 41 are exposed are formed on a side surface 42a of the second fluidic channel 42, and at least some of a top surface 42c or a bottom surface 42b of the second fluidic channel 42 is constituted by a transparent member 45 so that the microorganisms or cells T trapped at the adsorption portions S can be optically observed.

At least portions that configure the fine vacuum holes 41 in the base member 44 are formed of a single member.

In the base body 50 shown in FIG. 30, the single member configures not only the fine vacuum holes 41 but also the entire base member 44.

Examples of the material of the single member include silicon, glass, silica, sapphire, and the like.

The above materials are excellent in terms of the workability of the fine vacuum holes 41, which is preferable.

Among the above, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the material of the single member transmits the above laser light, it is possible to form modified regions by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIG. 30, the single member that configures the base member 44 is a transparent glass substrate.

As shown in FIG. 31, the fine vacuum holes 41 communicate the second fluidic channel 42 and the third fluidic channel 43.

The first end portions 41a of the fine vacuum holes 41 are exposed (opened) at the side surface 42a of the second fluidic channel 42, and form the adsorption portions S.

The second end portions 41b of the fine vacuum holes 41 are exposed at a side surface of the third fluidic channel 43.

The fine vacuum holes 41 are formed in the single glass substrate 44, and are through holes having no seam or adhered surface.

Naturally, there is no seam or adhered surface in the adsorption portions S at the end portion of the fine vacuum holes.

Here, the "adsorption portion S" refers to an area which the microorganisms or cells T come into contact with or come close to in the side surface 42a of the second fluidic channel 42.

The shape of the first end portions 41a of the fine vacuum holes 41 which configure the adsorption portions S at the side surface 42a of the second fluidic channel 42 may be any of a rectangle, a triangle, an oval, and a circle.

The description of the minor axis (the diameter of the shortest opening) and major axis (the diameter of the longest opening) of the hole is the same as the description of the hole in the second embodiment.

In FIG. 31, the fine vacuum holes 41 are formed substantially perpendicularly with respect to the side surface 42a of the second fluidic channel 42.

However, the fine vacuum holes do not necessarily need to be substantially perpendicular to the side surface, and can be freely disposed in a single glass substrate 44 in accordance with the design of the base body 50.

A plurality of fine vacuum holes 41 may be disposed in the base body 50.

Since each of the fine vacuum holes 41 has the adsorption portion S, it is possible to trap a plurality of microorganisms or cells T.

The bottom surface 42b of the second fluidic channel 42 is constituted by the member 45 such as a plastic, resin, or glass member.

The top surface 42c of the second fluidic channel 42 which is opposite to the bottom surface 42b is constituted by the base member 44 including a glass substrate.

It is possible to optically observe the microorganisms or cells T trapped at the adsorption portions S from at least one of the top surface 42c and the bottom surface 42b using a microscope or the like.

A bottom surface 43b of the third fluidic channel 43 is constituted by the member 45, and a top surface 43c of the third fluidic channel 43 is constituted by the glass substrate 44.

Thereby, the third fluidic channel 43 forms a space in a half-sealed state.

The second end portions 41b of the fine vacuum holes 41 are exposed and opened on the upstream of the third fluidic channel 43.

A negative pressure portion such as a syringe or a pump which can form a negative pressure in the third fluidic channel 43 is provided on the downstream of the third fluidic channel 43 (not shown).

Therefore, some of the fluid R which has flowed in from the upstream F1 of the second fluidic channel 42 to the downstream F2 of the second fluidic channel 42 is pulled into the third fluidic channel 43 through the fine vacuum holes 41 by forming a negative pressure in the third fluidic channel 43.

At this time, it is possible to draw and trap the microorganisms or cells T included in the fluid R at the adsorption portions S configured at the first end portions 41a of the fine vacuum holes 41 (not shown).

The mechanism thereof is the same as in the base body 20 of the second embodiment.

The material of the member 45 is not particularly limited, and it is possible to use a resin substrate such as PDMS or PMMA, or a glass substrate.

The member that configures the bottom surface 43b of the third fluidic channel 43 may be constituted by a material that does not transmit light (for example, visible light) used for observation.

In a case in which trapping of microorganisms or cells is the only object, the member does not necessarily need to transmit light that is used for observation.

When a member that transmits light used for observation is used, optical observation from the top surface becomes possible, which is preferable.

In a case in which an electrophysiological measurement of the trapped microorganisms or cells T is conducted, it is possible to dispose electrodes in the second fluidic channel 42, the third fluidic channel 43, and the like and to carry out the measurement in a manner described for the base body 20 of the second embodiment.

Alternatively, it is possible to carry out an electrophysiological measurement using external electrodes through an extracellular buffer, an intracellular fluid, or the like.

Figure 32:
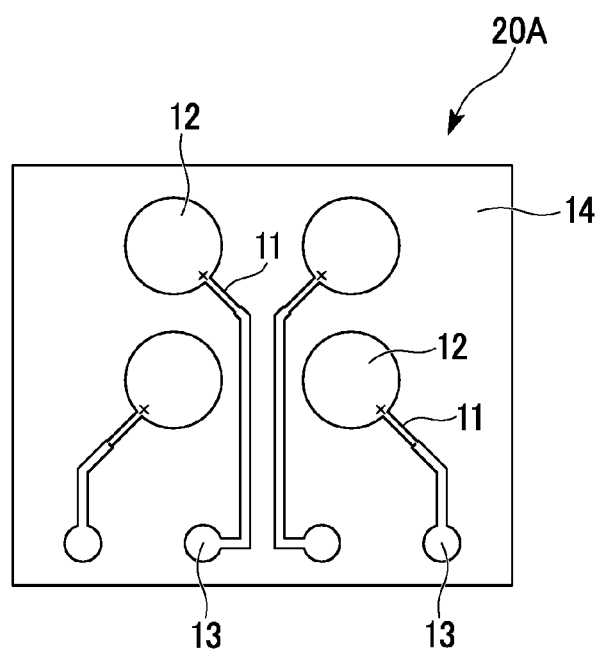
FIG. 32 is an outline top view showing an example of the base body for trapping microorganisms or cells according to the invention.

FIG. 32 is a schematic top view (transparent view seen from the top surface) of a base body 20A which is an example of the base body for trapping microorganisms or cells according to the invention.

The disposition configuration of the wells 12, the fine vacuum holes 11, and the first fluidic channels 13 on the top view can be applied to the base body 20 of the second embodiment, the base body 40 of the fourth embodiment, and the like.

Four sets of the well 12 and the first fluidic channel 13 are disposed respectively on the glass substrate 14.

The fact that the well 12 and the first fluidic channel 13 are communicated through the fine vacuum hole 11 is as described above.

The location of the adsorption portion S is shown using an "X" mark.

It is possible to dispose a plurality of first fluidic channels 13 in a well 12, and, at this time, at least one fine vacuum hole 11 is provided to one first fluidic channel 13.

In a case in which a plurality of first fluidic channels 13 are disposed in one well 12 as described above, the base bodies are capable of independently controlling the suction at the first fluidic channel 13 by independently connecting a sucking portion (not shown) such as a syringe or a pump to each of the first fluidic channels 13.

Therefore, it is possible to independently control the trapping of microorganisms or cells T at the fine vacuum holes 11.

Figure 33:
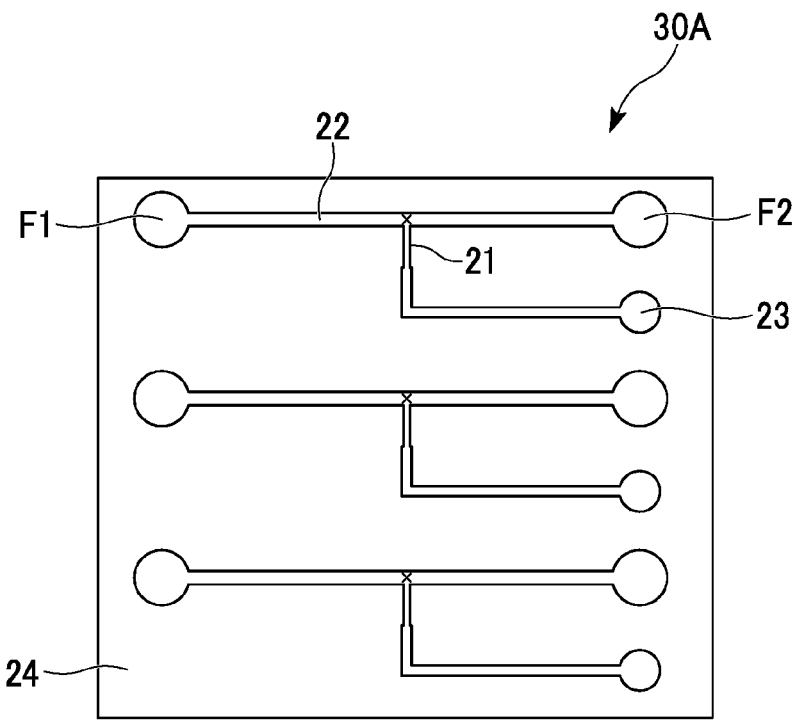
FIG. 33 is an outline top view showing an example of the base body for trapping microorganisms or cells according to the invention.

FIG. 33 is a schematic top view (transparent view seen from the top surface) of the base body 20A which is an example of the base body for trapping microorganisms or cells according to the invention.

The disposition configuration of the second fluidic channels 22, the fine vacuum holes 21, and the third fluidic channels 23 on the top view can be applied to the base body 30 of the third embodiment, the base body 50 of the fifth embodiment, and the like.

Three sets of the second fluidic channel 22 and the third fluidic channel 23 are disposed respectively on the glass substrate 24.

The fact that the second fluidic channel 22 and the third fluidic channel 23 are communicated through the fine vacuum hole 21 is as described above.

The location of the adsorption portion S is shown using an "X" mark.

The fluid R is made to flow in from the upstream F1 of the second fluidic channel 22 and circulates to the downstream F2 of the second fluidic channel 22.

It is also possible to dispose a plurality of third fluidic channels 23 in a second fluidic channel 22, and, at this time, at least one fine vacuum hole 21 is provided to one third fluidic channel 23.

In a case in which a plurality of third fluidic channels 23 are disposed in one second fluidic channel 22 as described above, the base bodies are capable of independently controlling the suction at the third fluidic channel 23 by independently connecting a sucking portion (not shown) such as a syringe or a pump to each of the third fluidic channels 23.

Therefore, it is possible to independently control the trapping of microorganisms or cells T at the fine vacuum holes 21.

Figure 34:
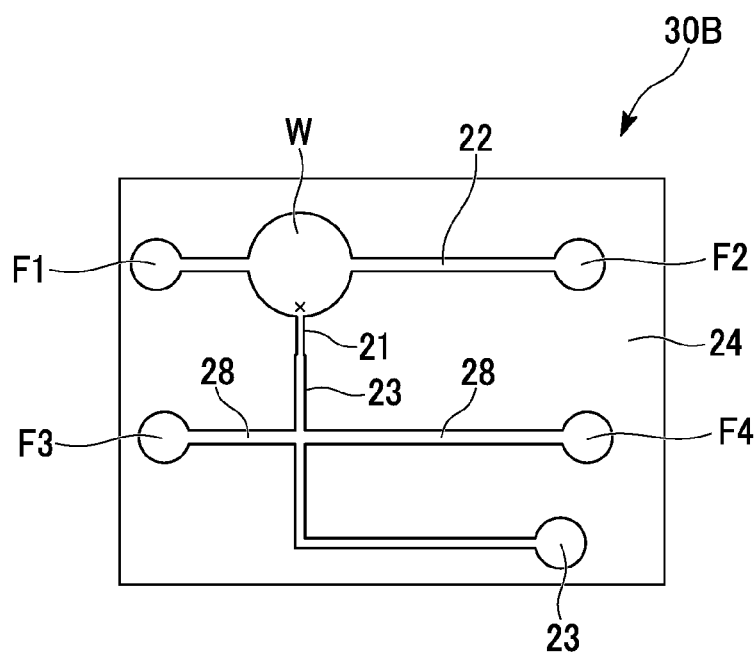
FIG. 34 is an outline top view showing an example of the base body for trapping microorganisms or cells according to the invention.

FIG. 34 is a schematic top view (transparent view seen from the top surface) of a base body 30B which is an example of the base body for trapping microorganisms or cells according to the invention.

The disposition configuration of the second fluidic channels 22, the fine vacuum holes 21, the third fluidic channels 23, and fifth fluidic channels 28 on the top view can be applied to the base body 30 of the third embodiment, the base body 50 of the fifth embodiment, and the like.

The fact that the second fluidic channel 22 and the third fluidic channel 23 which are disposed in the glass substrate 24 are communicated through the fine vacuum hole 21 is as described above.

The location of the adsorption portion S is shown using an "X" mark.

At an area W in which the adsorption portion S is provided, the fluidic channel width of the second fluidic channel 22 is expanded.

Therefore, when the fluid R is made to flow in from the upstream side F1 of the second fluidic channel 22 and circulates to the downstream F2 of the second fluidic channel 22, it is possible to make the fluid R remain in the area W.

The above remaining facilitates trapping of microorganisms or cells T included in the fluid R at the adsorption portions S.

In addition, it is possible to make the area W function as a well by opening the lid of the area.

A fifth fluidic channel 28 is disposed in the glass substrate 24.

The fifth fluidic channel 28 intersects the third fluidic channel 23 so as to communicate with the third fluidic channel.

It is also possible to make a desired chemical or gas diffuse and flow into the third fluidic channel 23 by circulating the chemical or gas from the upstream F3 to the downstream F4 of the fifth fluidic channel 28.

In addition, it is also possible to substitute a chemical diffused in the third fluidic channel 23 with gas.

The location at which the fifth fluidic channel 28 is communicated with the third fluidic channel 23 or the shape of the fifth fluidic channel 28 is not particularly limited.

Therefore, it is also possible to dispose the fifth fluidic channel 28 at, for example, a location near the fine vacuum hole 21, and to make the fifth fluidic channel 28 and the third fluidic channel 23 replace their functions respectively.

In addition, the fifth fluidic channel 28 can have a configuration in which only the F3 or the F4 is provided, it is also possible to make the third fluidic channel 23 perform the function of any of the F3 and F4, and a plurality of fifth fluidic channels 28 or the fifth fluidic channel 28 branched into a plurality of parts may be disposed.

Figure 35:
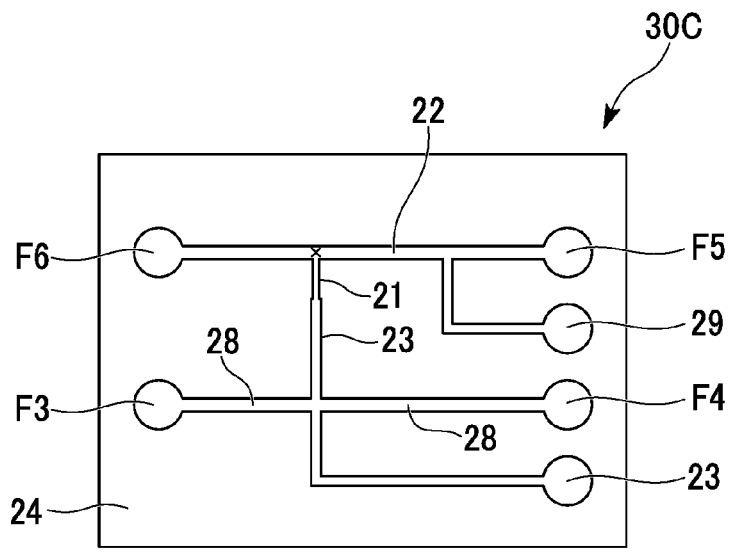
FIG. 35 is an outline top view showing an example of the base body for trapping microorganisms or cells according to the invention.

FIG. 35 is a schematic top view (transparent view seen from the top surface) of a base body 30C which is an example of the base body for trapping microorganisms or cells according to the invention.

The disposition configuration of the second fluidic channels 22, the fine vacuum holes 21, the third fluidic channels 23, the fifth fluidic channel 28, and the fourth fluidic channel 29 on the top view can be applied to the base body 30 of the third embodiment, the base body 50 of the fifth embodiment, and the like.

The fact that the second fluidic channel 22 and the third fluidic channel 23 which are disposed in the glass substrate 24 are communicated through the fine vacuum hole 21 is as described above.

The location of the adsorption portion S is shown using an "X" mark.

The fifth fluidic channel 28 disposed in the glass substrate 24 intersects the third fluidic channel 23 so as to communicate with the third fluidic channel.

It is also possible to make a desired chemical or gas diffuse and flow into the third fluidic channel 23 by circulating the chemical or gas from the upstream side F3 to the downstream side F4 of the fifth fluidic channel 28.

In addition, it is also possible to substitute a chemical diffused in the third fluidic channel 23 with gas.

The location at which the fifth fluidic channel 28 is communicated with the third fluidic channel 23 or the shape of the fifth fluidic channel 28 is not particularly limited.

Therefore, it is also possible to dispose the fifth fluidic channel 28 at a location near the fine vacuum hole 21, and to make the fifth fluidic channel 28 and the third fluidic channel 23 replace their functions respectively.

In addition, the fifth fluidic channel 28 can have a configuration in which only the F3 side or the F4 side is provided, it is also possible to make the third fluidic channel 23 perform the function of any of the F3 and F4, and a plurality of fifth fluidic channels 28 or the fifth fluidic channel 28 branched into a plurality of parts may be disposed.

In addition, the fourth fluidic channel 29 disposed in the glass substrate 24 is communicated with the second fluidic channel 22.

It is possible to make a desired chemical or gas diffuse and flow into the second fluidic channel 22 by circulating the chemical or gas from the fourth fluidic channel 29 to the second fluidic channel 22.

That is, it is possible to bring the chemical or gas into contact with the microorganisms or cells T trapped at the adsorption portions S.

In FIG. 35, the upstream of the second fluidic channel 22 is represented by F5, and the downstream is represented by F6.

The location at which the fourth fluidic channel 29 is communicated with the second fluidic channel 22 or the shape of the fourth fluidic channel is not particularly limited.

Therefore, it is also possible to dispose the fourth fluidic channel 29 at a location near the fine vacuum hole 21, and to make the fourth fluidic channel 29 and the upstream (F5 side) of the second fluidic channel 22 replace their functions respectively.

In addition, a plurality of fourth fluidic channels 29 or the fourth fluidic channel 29 branched into a plurality of parts may be communicated with the second fluidic channel 22, and may be disposed.

It is also possible to provide the fourth fluidic channel 29 so as to be communicated with a well instead of the second fluidic channel 22.

That is, in FIG. 35, it is also possible to form a configuration in which the second fluidic channel 22 is substituted with a well.

First Embodiment of a Base Body for Detecting a Small Amount of Macromolecule

[Base Body 60]

Figure 36:
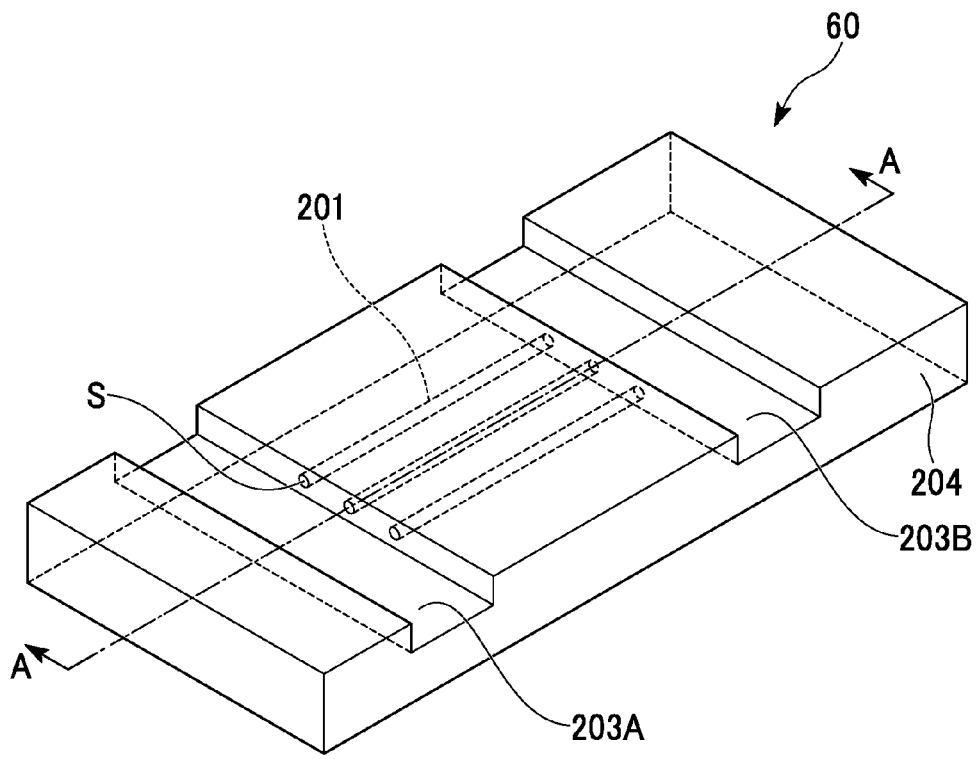
FIG. 36 is a schematic perspective view showing an example of a base body for detecting a macromolecule such as a small amount of a protein material included in a cell or the like according to the invention.

FIG. 36 is a perspective view of a base body 60 which is a first embodiment of a base body for detecting a macromolecule such as a small amount of a protein material included in a cell or the like according to the invention (hereinafter sometimes referred to simply as the "base body").

Figure 37:
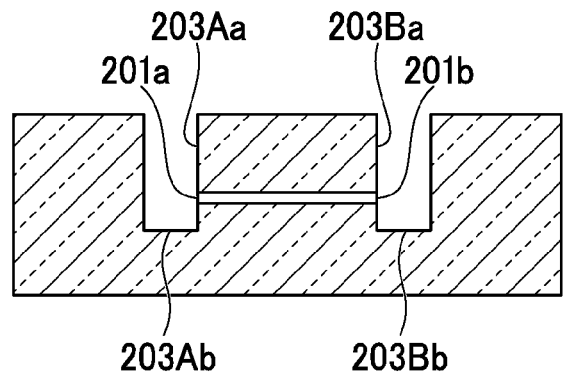
FIG. 37 is a cross-sectional view taken along the line A-A in FIG. 36.
Figure 38A:
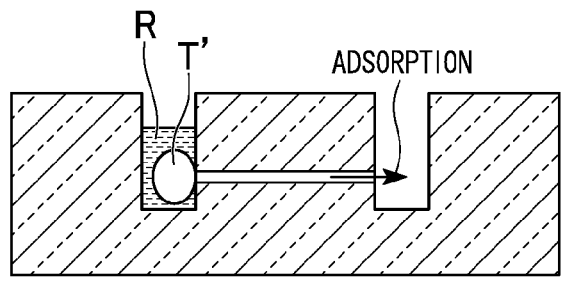
FIG. 38A is a schematic view showing an appearance in which a cell or the like is trapped at the adsorption portion in the cross-sectional view of FIG. 37.
Figure 38B:
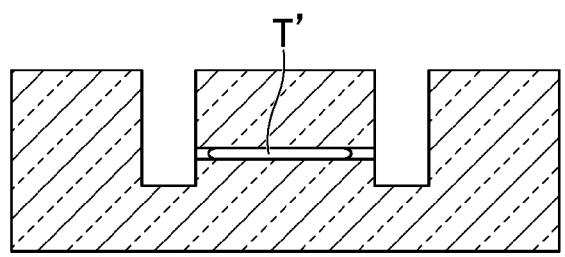
FIG. 38B is a schematic view showing an appearance in which a cell or the like is filled in a nanofluidic channel in the cross-sectional view of FIG. 37.

FIGS. 37, 38A, and 38B are schematic views showing a cross-section taken along the line A-A in FIG. 36.

The base body 60 is a base body having nanofluidic channels 201 that trap a cell or the like, and detect a small amount of macromolecule included in the cell or the like.

The base body 60 includes a micro fluidic channel 203A and a micro fluidic channel 203B which allow a fluid including the cell or the like to flow into the top surface of a base member 204 in the base member 204, and nanofluidic channels 201 that communicate the micro fluidic channel 203A and the micro fluidic channel 203B, and, at least portions that configure the nanofluidic channels 201 in the base member 204 are formed of a single member.

In addition, the nanofluidic channels 201 are present at the side surfaces 203Aa and 203Ba of the micro fluidic channels 203A and 203B, and are not in contact with the top surface and the bottom surface.

Furthermore, the single member is constituted by a transparent member (not shown) so that a macromolecule detected using an analysis component (detection portion) can be optically observed.

The base body 60 is provided with the micro fluidic channel 203A and the micro fluidic channel 203B at the top surface side of the base member 204.

The micro fluidic channel 203A or 203B configures a space which allows the cell or the like to flow in.

In addition, in FIG. 36, two micro fluidic channels are provided, but the shape and number of the micro fluidic channels are not limited.

Figure 49:
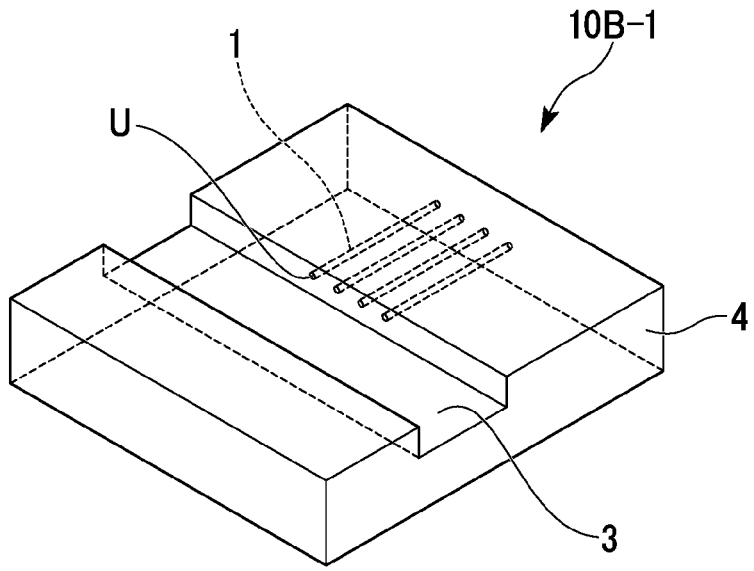
FIG. 49 is a schematic perspective view showing an example of the base body for forming a lipid membrane according to the invention.

The configuration may be the configuration of, for example, FIG. 1 or 49 as long as the space which allows the cell or the like to flow in is provided.

In a case in which the detected macromolecule is observed from the bottom surface of the base member 204, the observation subject is focused by adjusting the distance between the observation subject and the object lens (working distance).

However, in a case in which the distance between the bottom surface of the base member and the observation subjects is larger than the working distance necessary for observation, it is not possible to focus the observation subjects.

In order to avoid such a circumstance, it is possible to decrease the distance between the bottom surface of the base member and the observation subject by carrying out polishing or like of the bottom surface of the base member so as to decrease the thickness of the base member.

However, in a case in which nanofluidic channels that are open at the bottom surface 203Ab or 203Bb of the micro fluidic channels, since the nanofluidic channels are present between the bottom surface 203Ab or 203Bb of the micro fluidic channel and the bottom surface of the base member, there are cases in which it is difficult to decrease the thickness of the base member by carrying out polishing or the like of the bottom surface of the base member.

Therefore, the nanofluidic channels are preferably opened at the side surface 203Aa or 203Ba of the micro fluidic channel as in the base body 60.

Furthermore, the nanofluidic channels are preferably open as high as substantially half the side surface 203Aa or 203Ba of the micro fluidic channel in order to easily trap the observation subject.

The invention can be used not only for detecting a macromolecule in cells but also for detecting, as detection subjects, other ions or compounds in a liquid including the ions or compounds at a several molecule level.

For example, it is also possible to detect observation subjects from a liquid including the resistance properties of ATP, calcium, lipid molecules, a chemical, and an anticancer drug at a several molecule level.

In addition, for example, it is also possible to count the number of molecules of a chemical substance or a biological polymer included at an extremely small amount in blood, sweat, urine, or the like, and it is possible to make detection using gradient even for the above high-concentration liquids.

In addition, it is also possible to actively detect a small amount of ions or compounds discharged from ion channels or transporters without breaking cells.

In the base body 60 shown in FIG. 36, the single member configures not only the nanofluidic channel 201 but also the entire base member 204.

Examples of the material of the single member include glass, silica, sapphire, and the like.

The above materials are excellent in terms of the workability when forming the nanofluidic channels 201, which is preferable.

Among the above, the material is preferably an amorphous material that is not easily influenced by the working anisotropy determined by crystal orientations.

In addition, in a case in which the detected macromolecule is optically observed using a microscope or the like, the above material is more suitable for the observation since the material transmits visible light (wavelength 0.36 µm to 0.83 µm).

In addition, the material of the single member preferably transmits at least some wavelengths of light from light having a wavelength of 0.1 µm to 10 µm.

Specifically, the material of the single member preferably transmits light in at least a partial range of a general wavelength range (0.1 µm to 10 µm) which are used as a working laser light.

In a case in which the material of the single member transmits the above laser light, it is possible to form modified regions by irradiating, with the laser, the member as described below.

In addition, the single member preferably transmits light in the visible light range (approximately 0.36 µm to approximately 0.83 µm).

In a case in which the single member transmits light in the visible light range, it is possible to easily observe the detected macromolecule visually through the single member.

Furthermore, in a case in which the single member transmits at least some wavelengths of ultraviolet light or visible light (0.1 µm to 0.83 µm) of the light with the above wavelengths, it is possible to fluorescently observe a macromolecule dyed with a fluorescent pigment.

Meanwhile, in the invention, the "transmission (being transparent)" refers to everything about a state in which transmitted light is obtained from the member by entering light into the member.

In FIG. 36, the single member that configures the base member 204 is a transparent glass substrate.

As shown in FIGS. 37, 38A, and 38B, the nanofluidic channels 201 communicate the micro fluidic channel 203A and the micro fluidic channel 203B.

First end portions 201a of the nanofluidic channels 201 are exposed (opened) at the side surface 203Aa of the micro fluidic channel 203A, and form the adsorption portions S.

Second end portions 201b of the nanofluidic channels 201 are exposed at the side surface 203Ba of the micro fluidic channel 203B.

Figure 39:
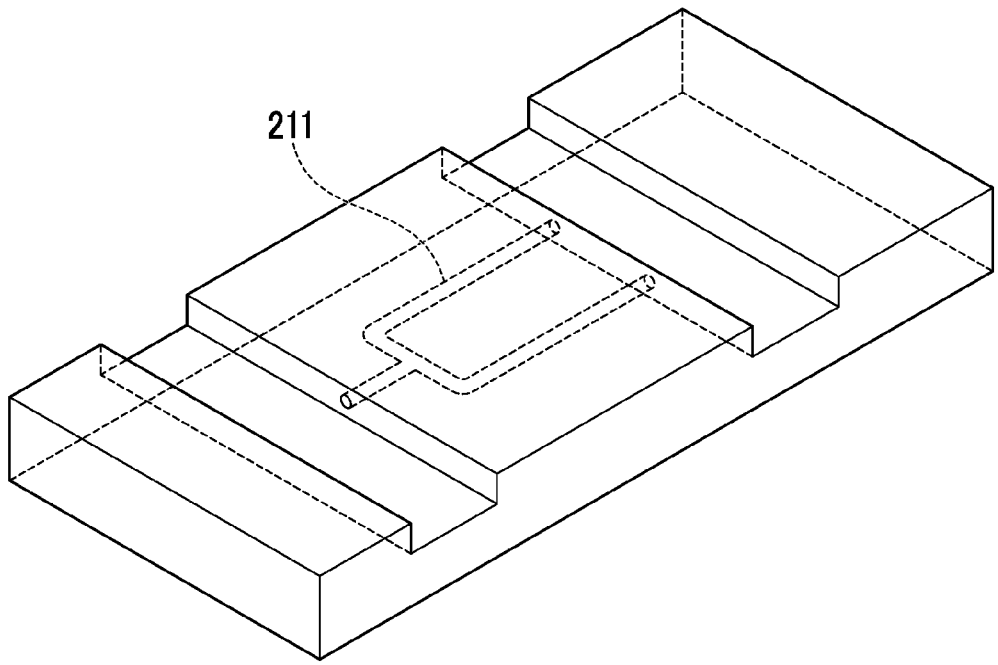
FIG. 39 is a schematic perspective view showing an example of a base body for detecting a macromolecule such as a small amount of a protein material included in a cell or the like according to the invention.
Figure 40:
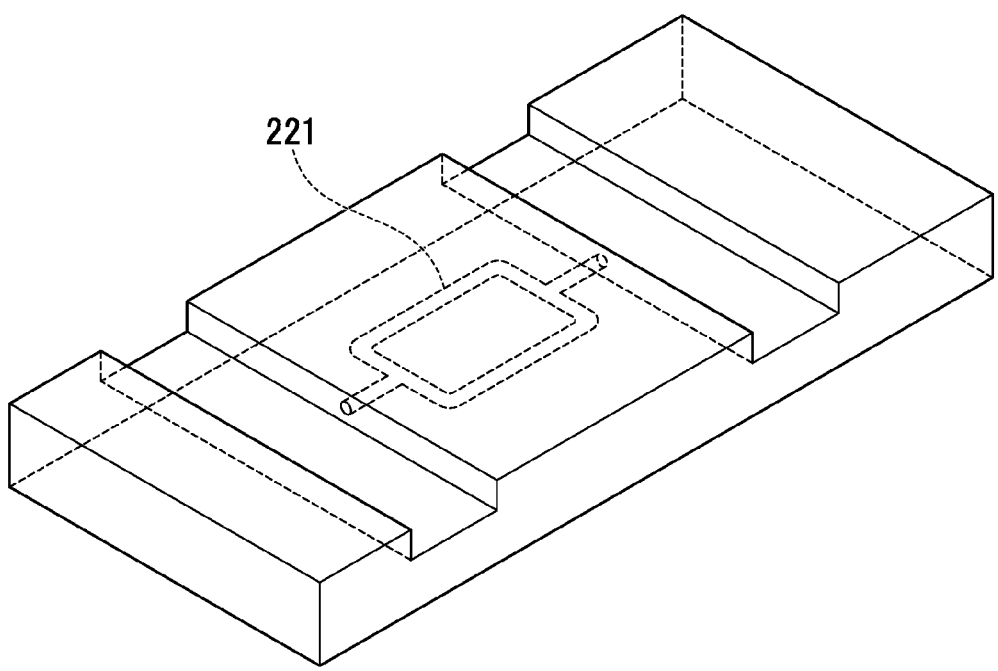
FIG. 40 is a schematic perspective view showing an example of a base body for detecting a macromolecule such as a small amount of a protein material included in a cell or the like according to the invention.

In the invention, when the nanofluidic channels 201 communicate the micro fluidic channel 203A and the micro fluidic channel 203B, the nanofluidic channel may have a branched structure like nanofluidic channels 211 and 221 provided in the base body shown in FIGS. 39 and 40.

In that case, it is possible to increase the volume of the nanofluidic channel, and, even in a case in which a small amount of macromolecule is detected from a cell or the like having a diameter of approximately several tens of it is possible to form a nanofluidic channel having a volume that is equal to or larger than the volume of the cell by having the above structure and to fill the cell or the like in the nanofluidic channel.

According to the above structure, it is possible to detect a small amount of macromolecule even from a large cell.

The branched nanofluidic channel may remain branched as in FIG. 39, or may be merged in the middle as in FIG. 40.

In addition, the structure of the nanofluidic channel is not limited to the above structure, and may be, for example, a curving structure or a structure branched into a plurality of parts (not shown).

In addition, the nanofluidic channel may have a structure in which, for example, a space having a width of 1 µm or less is provided and joined at a position other than the first end portion 201a of the nanofluidic channel 201 (not shown).

In addition, it is also possible to provide a manipulation micro fluidic channel at a location near the nanofluidic channel (not shown).

In that case, one side is preferably smaller than the dimension of the cell.

It is possible to trap the cells T included in the fluid R at the adsorption portions S (FIG. 38A) by sucking the fluid R in the fluidic channel 203A from the second end portion 201b of the nanofluidic channel 201 which is exposed to the fluidic channel 203B.

The power for the suction is not particularly limited, and, for example, it is possible to supply the power by connecting a sucking portion (not shown) such as a syringe or a pump to the second end portion 201b of the nanofluidic channel 201.

In addition, the volume of the nanofluidic channel 201 is preferably larger than the volume of the trapped cell.

In that case, it is possible to fill the cell T' trapped at the adsorption portion S in the nanofluidic channel 201 (FIG. 38B), and to detect the macromolecule included in the filled cell or the like at an analysis component (detection portion) such as an antibody directly or indirectly formed at the inner wall of the nanofluidic channel in advance.

The nanofluidic channels 201 are formed in a single glass substrate 204, and are through holes having no seam or adhered surface.

Naturally, there is no seam or adhered surface in the adsorption portions S at the end portion of the nanofluidic channels.

Therefore, the attaching force between the cells and the adsorption portion S is sufficiently increased.

In addition, since the nanofluidic channels 201 and the peripheral portions of the nanofluidic channels 201 are formed of the single glass substrate 204, and are through holes having no seam or adhered surface, peeling or breakage in an adhered surface does not occur due to the deformation or chemical-induced damage of the glass substrate 204.

Therefore, even when heating sterilization or chemical sterilization is repeatedly conducted on the glass substrate 204, there is no case in which the glass substrate 204 is broken.

The above fact can be said to be a particularly excellent characteristic for base bodies that detect cells or the like on which heating sterilization or chemical sterilization needs to be conducted on a routine basis.

Furthermore, since no difference in refractive index is caused in locations near the nanofluidic channels 201, it is easier to condense light from the adsorption portion S.

Therefore, it is possible to easily observe the detected macromolecule.

Here, the "adsorption portion S" refers to an area which the cells or the like come into contact with or come close to the side surface 203Aa of the micro fluidic channel 203A.

The shape of a hole which configures the adsorption portion S and is present at the first end portion 201a of the nanofluidic channel and at the side surface 203Aa of the micro fluidic channel 203A and the shape of the cross-section of the micro fluidic channel 203A in a direction parallel to the side surface 203Aa of the micro fluidic channel 203A are preferably oval.

In this case, it is possible to reliably detect a macromolecule having a short diffusion length in the nanofluidic channel using an analysis component (detection portion) such as an antibody as long as the minor axis (the diameter of the shortest opening portion) of the hole is in a range of 0.05 µm to 1.00 µm.

In addition, when the analysis component (detection portion) is disposed at the inner wall of the nanofluidic channel 201, the range of the minor axis is preferably 0.05 µm to 0.70 µm in order to increase the probability of the analysis component (detection portion) coming into contact with the inner wall of the nanofluidic channel.

Furthermore, the range of the minor axis is more preferably 0.05 µm to 0.40 µm.

When the minor axis is less than the lower limit value of the above range, there is a concern that the suctioning force at the adsorption portions S may weaken due to a pressure loss such that it becomes impossible to trap cells.

On the other hand, when the minor axis is the upper limit value or more of the above range, it is difficult to detect a small amount of macromolecule.

The major axis (the diameter of the longest opening portion) of the hole or the cross-section may be appropriately adjusted depending on the size of cells to be trapped, and is in a range of 1 µm to 6 µm when it is intended to trap all cells.

Furthermore, the major axis is more preferably in a range of 1 µm to 4 µm.

When the major axis is less than the lower limit value of the above range, there is a concern that the sucking force at the adsorption portions S may weaken due to a pressure loss such that the base bodies cannot trap cells.

On the other hand, when the major axis is the upper limit value or more of the above range, there is a possibility that the contents of a sample such as cells may leak outside.

Furthermore, the total length of the nanofluidic channel 201 is preferably adjusted appropriately from the minor axis and the major axis so that the volume of the nanofluidic channel 201 becomes the volume or more of cells or the like to be trapped, and the total length of the nanofluidic channel 201 is preferably 20 µm to 50000 µm in consideration of the influences of volume and pressure loss.

Furthermore, the total length is more preferably 20 µm to 25000 µm.

Similarly, the distance between the first end portion 201a and the second end portion 201b in the nanofluidic channel 201 is preferably 20 µm to 10000 µm.

Furthermore, the total length is more preferably 20 µm to 6000 µm.

In addition, the depth of the micro fluidic channels 203A and 203B is preferably 6 µm or more, and is preferably adjusted appropriately so as to become equal to or larger than the dimension of cells or the like.

As a specific example in which the invention is used, in a case in which a white blood cell (diameter of approximately 10 µm) is used as a detection subject, the nanofluidic channel needs to have a minor axis of approximately 0.20 µm, a major axis of approximately 3 µm, and a length of approximately 1.3 µm.

When the volume of the nanofluidic channel becomes approximately 1.5 times the volume of cells, a macromolecule is easily detected.

In a case in which the minor axis of the hole diameter of the hole is highly accurately processed on the order of nanometers, the base bodies are capable of detecting a macromolecule with a size of the order of nanometers, and the base bodies are capable of detecting a macromolecule such as a protein material included only at an extremely small amount in cells, it was required to detect the macromolecule at a large amount in the related art in a single or a small amount of cells.

As a result, it is possible to suppress a load on patients and the like to the minimum extent.

Furthermore, in a case in which the diameter of the hole at the adsorption portion is decreased, stabilized sealing properties between a cell and the adsorption portion is realized, and therefore it is possible to stably detect a macromolecule.

In FIGS. 37, 38A, and 38B, the nanofluidic channel 201 is formed to be substantially perpendicular to the side surface 203Aa of the micro fluidic channel 203A.

However, the nanofluidic channel does not necessarily need to be substantially perpendicular, and can be freely disposed in the single glass substrate 204 in accordance with the design of the base body 60.

In addition, the nanofluidic channel 201 is substantially horizontally disposed.

When the nanofluidic channel 201 is substantially horizontal, it is possible to easily observe a macromolecule detected using the analysis component (detection portion) using a fluorescent mark or the like.

In addition, a plurality of nanofluidic channels 201 may be disposed in the base body 60.

In this case, since the adsorption portion S is provided to each of the nanofluidic channels 201, it is possible to trap a plurality of cells and the like and to efficiently detect a macromolecule.

In addition, when a plurality of nanofluidic channels 201 are disposed in one micro fluidic channel 203A, it is possible to separately control the suction at the nanofluidic channels 201 by connecting an independent suctioning portion (not shown) such as a syringe or a pump to the second end portion 201b of a nanofluidic channel 201.

Therefore, it is possible to independently control the detection of a macromolecule using the nanofluidic channels 201.

Furthermore, when the material of the base member 204 is glass, silica, sapphire, or the like, since the materials are excellent in terms of workability, it is possible to tightly dispose a plurality of nanofluidic channels 201.

In the base body 60, the bottom surfaces 203Ab and 203Bb of the micro fluidic channel 203A and the micro fluidic channel 203B are constituted by the base member 204 including a glass substrate.

The top surface of the micro fluidic channel 203A which is opposite to the bottom surface 203Ab or 203Bb is opened, and has no lid.

Therefore, it is possible to optically observe cells and the like trapped at the adsorption portions S from the bottom surface 203Ab or 203Bb or the top surface using a microscope or the like.

It is not a definite requirement that the top surface has no lid, and the top surface may be covered with a lid including a member such as a plastic, a resin, or a glass member (not shown).

Since it is possible to detect a protein material present in the micro fluidic channel 203A while observing the protein material, it is possible to appropriately adjust the suctioning force depending on the state of the protein material by, for example, strengthening the sucking force when an attempt is made to trap cells, and weakening the sucking force to an extent at which the cell membranes are not broken after trapping the cells.

In a case in which an electrophysiological measurement of the trapped cells and the like is conducted, for example, electrodes (not shown) may be disposed respectively in the micro fluidic channel 203A and the second end portion 201b of the nanofluidic channel.

Alternatively, external electrodes may be used through an extracellular buffer, an intracellular fluid, or the like.

Since the adsorption portion S is formed of the single glass substrate 204, it is possible to form high resistance sealing with respect to cells and the like.

Therefore, the well-known patch-clamp method of the related art can be applied.

At this time, it is possible to carry out a more highly accurate electrophysiological measurement than in the related art by making the diameters of the openings of the holes on the first end portion 201a of the nanofluidic channels 201 that configure the adsorption portions S be smaller than the diameter of the opening (approximately 2 μm to 4 μm) of the hole of a patch pipet or the like of the related art.

<Method of Detecting a Small Amount of Macromolecule>

In order to detect an extremely small amount of a protein material in a cell, it is possible to apply, for example, a sandwich method in which an antibody is used.

A specific detecting method will be described below.

Firstly, an antibody (capture antibody) of a target protein material (antigen) is adsorbed in the inner wall of the nanofluidic channel 201, and the inner wall of the nanofluidic channel 201 is blocked using a macromolecule, for example, skim milk, PEG, or the like.

At this time, in order to efficiently form the antibody at the inner wall of the nanofluidic channel in advance, an adsorption film is preferably formed by carrying out a hydrophobic surface treatment using a silane coupling material or the like.

Subsequently, a primary antibody that recognizes a separate epitope from a specimen solution and the capture antibody at the inner wall of the nanofluidic channel 201 is added.

An enzyme for detecting an enzymatic binding such as alkaline phosphatase, β galactosidase, peroxidase, or luciferase is genetically or chemically coupled with the primary antibody.

In addition, it is also possible to make a detection using biotin-avidin, DIG, or the like in addition to the above.

At a point in time, a complex formed of the capture antibody, the antigen, and the primary antibody is formed on the inner walls of the nanofluidic channels 201.

In addition, it is possible to detect products of an enzyme reaction using a microscope or the like by washing unreacted antigen and primary antibody, and adding a matrix of the enzyme such as a chromogenic or luminescent reagent.

In order to carry out the above sandwich method, an antibody that recognizes the same protein material with different epitopes becomes necessary.

In addition, when the steric hindrance of the antibody is taken into consideration, it is preferable to use an antibody that recognizes a distal portion rather than a proximal portion (The distal portion is a distal portion of the steric structure, and the distal portion is not a distal portion of the amino acid array).

In addition, since two kinds of antibodies such as the capture antibody and the primary antibody are used for the same protein material, the specificity is extremely high, and it is possible to highly accurately detect the target protein material.

It is possible to maintain the detection effects of the antigen for a long period of time by disposing the above analysis component (detection portion) such as an antibody in the inner walls of the nanofluidic channels, and then drying the base body.

Therefore, it is possible to store the base body in a state in which the analysis component (detection portion) is disposed in the inner walls of the nanofluidic channels.

Here, an antibody is used as the analysis component, but it is also possible to use, for example, peptides, a macromolecule that is specifically adsorbed in a specific material, or the like, and the analysis component is not limited.

Examples of other analysis component include functional DNA, functional RNA, and the like.

In this case, examples of the functional DNA or the functional RNA include aptamers, and the aptamers can be used for analyses of ATP and the like.

In addition, it is also possible to use a peptide aptamer as the aptamer instead of the functional DNA aptamer or the RNA aptamer.

Next, a method of manufacturing the base body for trapping microorganisms or cells according to the invention will be described.

Method of Manufacturing the Base Body for Trapping Microorganisms or Cells (First Embodiment)

A first embodiment of the manufacturing method of the invention will be described using the base body 20 as an example.

In this case, in the manufacturing method, a laser L having a pulse duration on the order of picoseconds or less is irradiated to areas that form fine vacuum holes 55 in a single member 59 as shown in FIGS. 41A to 41D.

In addition, the manufacturing method includes at least a process A1 (FIG. 41A) in which modified regions 51 are formed in the areas, a process A2 (FIG. 41B) in which recess portions 53 and 54 or through holes that configure a well 57 and a first fluidic channel 58 that form the space (or a second fluidic channel 57 and a third fluidic channel 58 that form the space) are formed in the single member 59, and a process A3 (FIG. 41C) in which the modified regions 51 are removed from the single member 59 through etching.

[Process A1]

As the laser L (laser light L), laser light having a pulse width for which the pulse duration is on the order of picoseconds or less is preferably used.

For example, it is possible to use a titanium sapphire laser, a fiber laser having the above pulse width, or the like.

However, it is necessary to use a wavelength at which the member 59 transmits the laser light.

More specifically, laser light having a transmittance with respect to the member 59 of 60% or more is preferably used.

As the laser L (laser light L), it is possible to apply light in a general wavelength area (0.1 μm to 10 μm) which is used as a working laser.

Among the above, the laser needs to transmit the member 59 which is a member to be worked.

It is possible to form the modified regions 51 with respect to the member 59 by applying laser light having a wavelength at which the laser light transmits the member 59.

Examples of the material of the member 59 include silicon, glass, silica, sapphire, and the like.

The above materials are excellent in terms of the workability when forming the fine vacuum holes 55, which is preferable.

Among the above, the material is preferably an amorphous material that is not easily influenced by the working anisotropy determined by crystal orientations.

Furthermore, in a case in which glass, silica, or sapphire is employed as the material of the member 59, and the trapped microorganisms or cells T are optically observed using a microscope or the like, the above material is more suitable for the observation since the material transmits visible light (wavelength 0.36 μm to 0.83 μm).

In addition, the material of the member 59 preferably transmits at least some wavelengths of light from light having a wavelength of 0.1 μm to 10 μm.

Specifically, the material of the member 59 preferably transmits light in at least a partial range of a general wavelength range (0.1 μm to 10 μm) which are used as a working laser light beam.

In a case in which the material of the member 59 transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIGS. 41A to 41D, the single member 59 is a transparent glass substrate (hereinafter referred to as the glass substrate 59).

Hereinafter, a case in which the member 59 is a glass substrate will be described, but it is possible to manufacture the base body in the same manner even in a case in which the material of the member 59 is other member, for example, silicon, silica, or sapphire.

In the process A2 described below, silicon, silica, or glass which has favorable workability is more preferable.

As the glass substrate 59, it is possible to use, for example, a glass substrate including silica, a glass substrate including glass mainly including silicate or borosilicate glass, or the like.

A glass substrate including synthetic silica is preferable due to the favorable workability.

In addition, the thickness of the glass substrate 59 is not particularly limited.

Figure 41A:
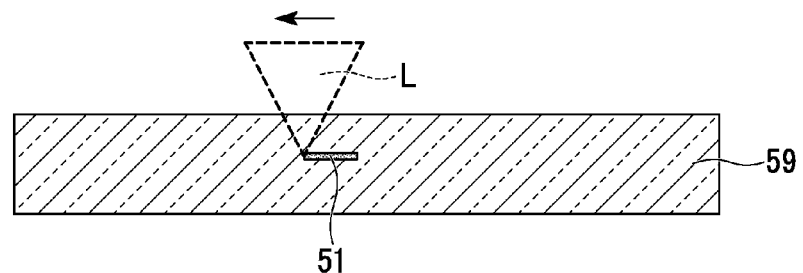
FIG. 41A is an outline cross-sectional view showing an example of a method of manufacturing the base body for trapping microorganisms or cells according to the invention.

As the method of irradiating with the laser light L, a method shown in FIG. 41A can be used.

That is, the modified regions 51 modified from glass are formed by irradiating with the laser light L so as to be condensed and focused in the glass substrate 59, and scanning the focus in the direction of arrow.

It is possible to form the modified region 51 with a desired shape by scanning the focus over areas that form the fine vacuum holes 55 in the glass substrate 59.

Here, the "modified region" refers to a portion which has a decreasing etching resistance, and is selectively or preferentially removed through etching.

When the laser light L is irradiated, it is preferable that the irradiation intensity is a value near the working threshold value or is lower than the working threshold value of the glass substrate 59, and the polarization direction (electric field direction) of the laser light L so as to become perpendicular to the scanning direction.

This laser irradiating method will be hereinafter referred to as the laser irradiating method S.

The laser irradiating method S will be described in FIG. 42.

The propagation direction of the laser light L is indicated with the arrow Z, and the polarization direction (electric field direction) of the laser light L is indicated by the arrow Y.

In the laser irradiating method S, the irradiation area of the laser light L is so as to be in a planar surface 50a including the propagation direction of the laser light S and the direction perpendicular to the polarization direction of the laser light S.

Together with the above, the laser irradiation intensity is a value near the working threshold value or is lower than the working threshold value of the glass substrate 59.

It is possible to form the modified regions 51 having a diameter of the opening on the order of nanometers in the glass substrate 59 using the laser irradiating method S.

For example, the modified region 51 having a substantially oval cross-section with a minor axis of approximately 20 nm and a major axis of approximately 0.2 μm to 5 μm are obtained.

The substantially oval shape has the long axis in a direction along the propagation direction of the laser and the short axis in a direction along the electric field direction of the laser.

Depending on the conditions of the laser irradiation, there are cases in which the cross-section forms a shape similar to rectangular.

In a case in which the laser irradiation intensity is greater than or equal to the working threshold value of the glass substrate 59, there is a possibility that the obtained modified regions 51 are formed in accordance with the periodic structure.

That is, when a pulse laser on the order of picoseconds or less is irradiated in a collective manner at a working threshold value or more, interruption between an electronic plasma wave and the incident light occurs at the light-condensing portion, and a periodic structure that is perpendicular to the polarization of the laser and has a periodicity in the polarization direction is formed in a self-assembled manner.

The formed periodic structure forms a layer with a low etching resistance.

For example, in the case of silica, low oxygen concentration layers and high oxygen concentration layer are periodically arrayed (FIGS. 43C and 43D), the etching resistance decreases at the low oxygen concentration portions, and periodic recess portions and protrusions are formed when etching is conducted.

The above periodic recess portions and protrusions are not necessary when forming the fine vacuum holes 55 described below.

Figure 43A:
FIG. 43A is a view schematically showing the relationship between laser irradiation energy and a formed modified region (low oxygen concentration low oxygen concentration portion).
Figure 43B:
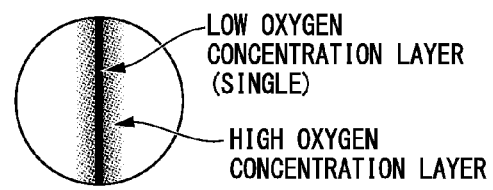
FIG. 43B is a view schematically showing the relationship between laser irradiation energy and the formed modified region (low oxygen concentration portion).
Figure 43C:
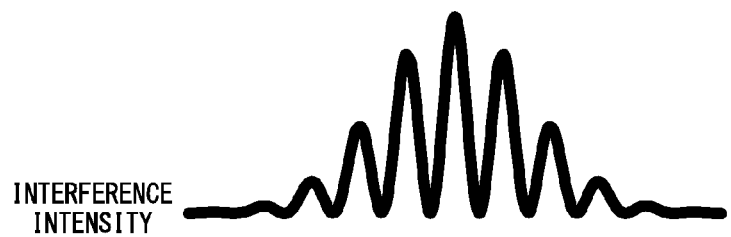
FIG. 43C is a view schematically showing the relationship between laser irradiation energy and the formed modified region (low oxygen concentration portion).
Figure 43D:
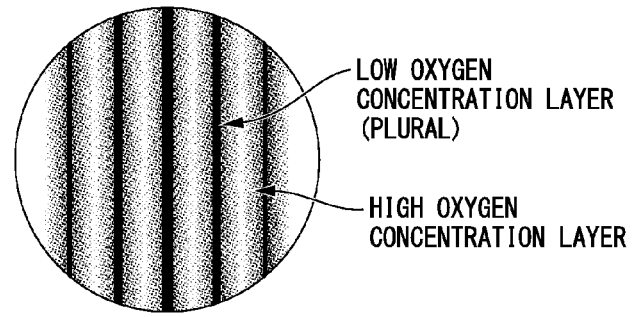
FIG. 43D is a view schematically showing the relationship between laser irradiation energy and the formed modified region (low oxygen concentration portion).

When the laser irradiation intensity is lower than the working threshold value of the glass substrate 59 and is greater than or equal to the lower limit value of the laser irradiation intensity at which the etching resistance can be decreased by modifying the glass substrate 59 as in the above laser irradiation method S, one low oxygen concentration portion (a layer having a low etching resistance) is formed through laser irradiation without forming the periodic structure (FIGS. 43A and 43B).

When the above etching is conducted, it is possible to form one fine vacuum hole 55.

The above laser irradiating method S can make the shape of the fine vacuum hole 55 be oval or substantially oval.

In addition, the base bodies are capable of being controlled the minor axis at a size on the order of nanometers through etching.

When the minor axis of the oval or substantially oval shape is made to be smaller than the size of microorganisms, the base bodies are capable of trapping microorganisms.

At this time, since it is possible to make the major axis larger than a size on the order of nanometers, it is possible to decrease the pressure loss of a fluid which flows into the fine vacuum holes 55.

In addition, as a preliminary preparation for trapping cells or microorganisms, it is necessary to fill a fluid in the fine vacuum holes 55 in advance.

In this case, since the capillary force increases as the holes become finer, there are cases in which an adverse effect of the fluid failing to flow outside the space or the like from the fine vacuum holes 55 is caused.

However, when the fine vacuum holes 55 are made to be oval or substantially oval, the capillary force is suppressed even in a minor axis that is small enough to trap microorganisms so that it is possible to suppress the adverse effect of the fluid failing to flow outside the space or the like.

Even when only one layer having a low etching resistance (the low oxygen concentration layer for silica or glass) is formed through laser irradiation (in the present specification, referred to as the modified region 51), the low oxygen concentration portions become layers which are extremely easily etched.

The above fact was found through thorough studies by the present inventors.

Therefore, the working threshold value is defined as the lower limit value (the upper limit value of the range of laser irradiation intensities at which the periodic structure is not formed) of laser irradiation intensities at which the periodic structure can be formed.

Hereinafter, in order to avoid confusion with the "working lower limit threshold value" described below, the working threshold value will be referred to as the working upper limit threshold value.

In addition, the "lower limit value of laser irradiation intensities at which the etching resistance can be decreased by modifying the glass substrate 59" refers to a limit value at which it is possible to open the fine vacuum holes 55 in the glass substrate 59 through an etching treatment.

When the laser irradiation intensity is lower than the lower limit value, it is not possible to form a layer with a low etching resistance through laser irradiation, and therefore the fine vacuum holes 55 are not opened.

Hereinafter, the lower limit value of the laser irradiation intensity will be referred to as the "working lower limit threshold value".

That is, the "working upper limit threshold value" refers to the lower limit value of laser irradiation intensities at which interruption between an electronic plasma wave generated by the interaction between the base member and the laser light and the entering laser light occurs in the focus (light-condensing area) of light irradiated into the base member, and a banded modified region can be formed in a self-assembled manner in the base member due to the interruption.

In addition, the "working lower limit threshold value" refers to the lower limit value of laser irradiation intensities at which the modified region modified from the base member is formed in the focus (light-condensing area) of laser light irradiated into the base member, and the etching resistance of the modified region can be decreased so that the modified region can be selectively or preferentially etched through an etching treatment which is a post process.

An area to which a laser is irradiated with a laser irradiation intensity lower than the working lower limit threshold value is not easily etched selectively or preferentially in the etching treatment which is a post process.

Therefore, in order to form the modified region that forms a micro hole after etching, it is preferable to set a laser irradiation intensity of the lower limit threshold value to the upper limit threshold value.

The working upper limit threshold value and the working lower limit threshold value are roughly determined depending on the wavelength of the laser light, the material (material quality) of the base member which is a subject of laser irradiation, and the laser irradiation conditions.

However, when the relative orientation of the polarization direction and scanning direction of the laser light differs, there are cases in which the working upper limit threshold value and the working lower limit threshold value also somewhat differ.

For example, in a case in which the scanning direction is perpendicular to the polarization direction and a case in which the scanning direction is parallel to the polarization direction, there are cases in which the working upper limit threshold value and the working lower limit threshold value differ.

Therefore, for the wavelength of the laser light to be used and the base member to be used, it is preferable to investigate in advance the working upper limit threshold values and the working lower limit threshold values of cases in which the relative relationship between the polarization direction and the scanning direction of the laser light is changed.

A linear polarization has been described in detail as the polarization, it can be easily assumed that the same structure (modified region) is formed even when a laser pulse having a somewhat oval polarization component is used.

The method of scanning the focus of the laser light L is not particularly limited, and the modified region 51 that can be formed through a single process of continuous scanning is limited in the planar surface 50a including the propagation direction (the arrow Z direction) of the laser light and the direction perpendicular to the polarization direction (the arrow Y direction) of the laser light.

It is possible to form the modified region in an arbitrary shape as long as the modified region is formed in the planar surface.

Figure 42:
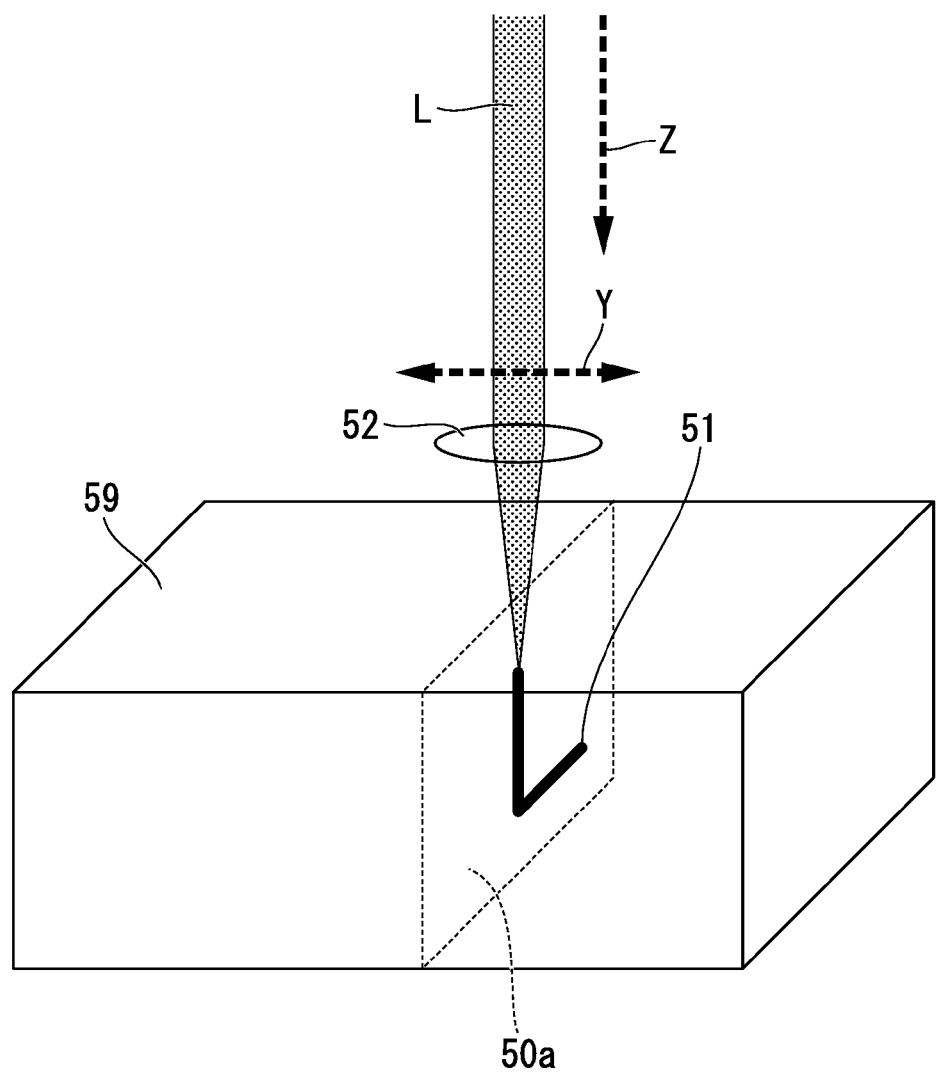
FIG. 42 is a schematic perspective view showing a laser irradiation method S.

Here, a case in which the propagation direction of the laser light L is perpendicular to the top surface of the glass substrate 59 has been shown in FIG. 42, but the propagation direction is not necessarily perpendicular.

The laser L may be irradiated at a desired incident angle with respect to the top surface.

Generally, the transmittance of the laser at the modified region differs from the transmittance of the laser at an unmodified region.

Therefore, it is generally difficult to control the focus location of the laser light being transmitted at the modified region.

Therefore, the modified region is desirably formed at an area located inside when seen from a surface on the laser irradiation side.

In addition, it is also possible to form the modified region having an arbitrary shape in the three-dimensional direction in the glass substrate 59 by appropriately changing the polarization direction (the arrow Y direction) of the laser.

In addition, as shown in FIG. 42, the modified region 51 may be formed by condensing the laser light L using a lens 52 and irradiating with the laser light as described above.

As the lens, it is possible to use, for example, a refractive object lens or a reflective lens, and, alternatively, it is also possible to irradiate the laser light, for example, in a Fresnel, reflective, oil immersion, or water immersion manner.

In addition, for example, when a cylindrical lens is used, it is possible to irradiate with the laser in a wide range on the glass substrate 59 at a single process.

In addition, for example, when a conical lens is used, it is possible to irradiate with the laser light L in a wide range in the perpendicular direction of the glass substrate 59 at a single process.

However, in a case in which a cylindrical lens is used, the polarization of the laser light L needs to be horizontal to a direction in which the lens has a curvature.

Specific examples of the laser irradiation conditions S include a variety of the following conditions.

For example, a titanium sapphire laser (a laser using a crystal obtained by doping titanium in sapphire as a laser medium) is used.

The laser light to irradiate has, for example, a wavelength of 800 nm and a repetition frequency of 200 kHz, and the laser light L is irradiated in a collective manner at a laser scanning rate of 1 mm/second.

The values of the above wavelength, repetition frequency, and scanning rate are an example, are not limited thereto for the invention, and can be arbitrarily changed.

As the lens 52 used for condensing light, for example, an object lens having N.A.<less than 0.7 is preferably used.

In order to form finer vacuum holes 55, when the glass substrate 59 is irradiated, the pulse intensity is preferably a value near the working upper limit threshold value, for example, a power of approximately 80 nJ/pulse or less.

When the power is the above value or more, since the periodic structure is formed, and is connected through etching, it becomes difficult to form the fine vacuum holes 55 having a diameter of the opening on the order of nanometers.

In addition, even when N.A.≥0.7, working is possible; however, since the size of the spot becomes smaller, and the laser fluence becomes larger, there is a demand for irradiation of the laser at a smaller pulse intensity.

[Process A2]

Subsequently, the recess portions 53 and 54 or through holes which configure the well 57 and the first fluidic channel 58 which forms the space (or the second fluidic channel 57 and the third fluidic channel 58 which form the space) are formed in the single glass substrate 59.

Examples of the method of forming the recess portions 53 and 54 include the following method.

Firstly, a resist 52 is patterned on the top surface of the glass substrate 59 through, for example, photolithography or the like.

Figure 41B:
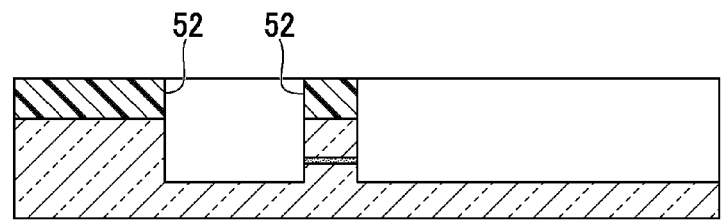
FIG. 41B is an outline cross-sectional view showing an example of the method of manufacturing the base body for trapping microorganisms or cells according to the invention.

Subsequently, areas in which the resist 52 is not patterned on the top surface of the glass substrate 59 are etched and removed to a desired depth using a method such as dry etching, wet etching, or sand blasting (FIG. 41B).

At the end, when the resist 52 which has become unnecessary is peeled off, the glass substrate 59 on which the first recess portion 53 and the second recess portion 54 are formed is obtained.

In the above example, a case in which the first recess portion 53 becomes the well 57, and the second recess portion 54 becomes the first fluidic channel 58 has been described.

In the process A2, the cross-section of the modified region 51 formed in the process A1 is preferably exposed at the side surfaces of the first recess portion 53 and the second recess portion 54 to be formed.

It becomes easier to form the fine vacuum holes 55 through an etching treatment in the process A3 at the later phase.

In addition, in the process A2, through holes may be formed instead of forming the recess portions 53 and 54.

In this case, the first fluidic channel (the second fluidic channel and the third fluidic channel) may be formed by excavating areas that form the first fluidic channel and the second fluidic channel in the glass substrate 59 from the surface of the glass substrate 59 using a fine drilling (laser drilling) or the like so as to form through holes.

In addition, combinations of the excavating method using the drill and a variety of etching methods may be used.

[Process A3]

Figure 41C:
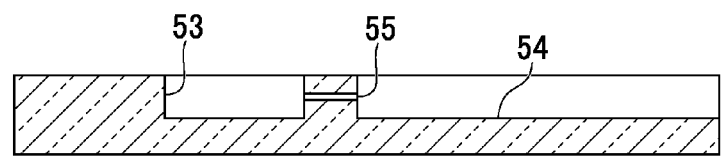
FIG. 41C is an outline cross-sectional view showing an example of the method of manufacturing the base body for trapping microorganisms or cells according to the invention.

Subsequently, the modified regions 51 formed in the process A1 are removed from a single glass substrate 59 through etching (FIG. 41C).

Wet etching is preferable as the etching method.

Since the modified regions 51 having the cross-section exposed at the side surfaces of the recess portions 53 and 54 (or the through holes) have a decreased etching resistance, selective or preferential etching is possible.

The above etching is a method in which a phenomenon in which the modified regions 51 are etched extremely faster than the unmodified regions in the glass substrate 59 is used, and, consequently, it is possible to form the fine vacuum holes 55 in accordance with the shape of the modified regions 51.

The etching fluid is not particularly limited, and, for example, a solution mainly including hydrofluoric acid (HF), a hydrofluoric-nitric acid-based mixed acid obtained by adding an appropriate amount of nitric acid or the like to hydrofluoric acid, or the like can be used.

In addition, it is also possible to use other chemicals in accordance with the material of the member 59.

As a result of the etching, it is possible to form the fine vacuum holes 55 having a diameter of the opening on the order of nanometers at predetermined locations in the glass substrate 59 so as to communicate the first recess portion 53 and the second recess portion 54.

As the size of the fine vacuum holes 55, for example, it is possible to make through holes having a substantially oval cross-section having a minor axis of approximately 20 nm to 200 nm and a major axis of approximately 0.2 μm to 5 μm.

There are cases in which the cross-section becomes substantially rectangular depending on the conditions of the etching treatment.

It is possible to control the size of the fine vacuum holes 55 by adjusting the treatment duration of the wet etching.

Theoretically, it is possible to make the minor axis several nm to several tens of nm by shortening the treatment duration.

In contrast to the above, it is also possible to make the minor axis approximately 1 μm to 2 μm and the major axis approximately 5 μm to 10 μm.

Figure 41D:
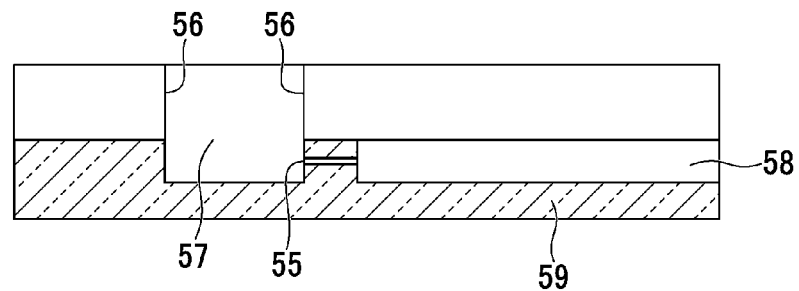
FIG. 41D is an outline cross-sectional view showing an example of the method of manufacturing the base body for trapping microorganisms or cells according to the invention.

Next, it is possible to form the first fluidic channel 58 by adhering a member 56 to the top surface of the glass substrate 59 so as to cover the formed second recess portion 54 (FIG. 41D).

The formed first recess portion 53 can be used as the well 57 as it is, and it is possible to appropriately adjust the depth of the well 57 by adhering the member 56 to the glass substrate 59 while the top surface of the well 57 is made to remain open as shown in FIG. 41D.

It is also possible to form the second fluidic channel 57 instead of the well 57 by adhering the member 56 to the top surface of the glass substrate 59 so as to cover the first recess portion 53 (not shown).

In this case, the first fluidic channel 68 can be differently referred to as the third fluidic channel 68.

As the method of adhering the member 56 and the top surface of the glass substrate 59, a well-known method may be conducted depending on the material of the member 56.

In addition, it is also possible to appropriate install electrodes, wires, and the like for an electrophysiological measurement in the first fluidic channel 58 during the adhering.

The material of the member 56 is not particularly limited, and it is possible to use a resin substrate such as PDMS or PMMA, or a glass substrate.

In addition, the material of the member 56 may be constituted by a material that does not transmit light (for example, visible light) used for observation.

In a case in which trapping of microorganisms or cells is the only object, the material does not necessarily need to transmit light that is used for observation.

When a member that transmits light used for observation is used, optical observation from the top surface becomes possible, which is preferable.

The member that is used to form the first fluidic channel 58 and covers the second recess portion 54 does not necessarily need to be a member that transmits light that is used for observation, and may be a member that does not transmits light that is used for observation.

As the etching in the process A2 and the process A3, wet etching or dry etching can be applied.

In the wet etching, for example, use of 1% or less of hydrofluoric acid is most preferable, but a material having other acidic or basic properties may be used.

Among the dry etching, examples of an isotropic etching method include a variety of dry etching methods such as barrel-type plasma etching, parallel plate-type plasma etching, and down flow-type chemical dry etching.

Among anisotropic dry etching methods, as a method in which reactive ion etching (hereinafter RIE) is used, it is possible to use, for example, parallel plate RIE, magnetron-type RIE, ICP-type RIE, NLD-type RIE, and the like.

In addition to RTE, it is possible to use etching in which, for example, a neutral beam etching is used.

In addition, in a case in which an anisotropic dry etching method is used, it is also possible to carry out a process similar to isotropic etching by shortening the mean free path of ions using a method of increasing the process pressure or the like.

As a gas being used, it is possible to use a gas mixture obtained by mixing a main component of a gas that can chemically etch the material such as fluorocarbon-based gas, SF-based gas, $CHF_3$, fluorine gas, or chlorine gas, and other appropriate gases, such as for example, oxygen, argon, helium, or the like.

In addition, it is also possible to carry out the process using other dry etching methods.

Anisotropic etching is more preferable in the process A2, and isotropic etching is more preferable in the process A3.

Method of Manufacturing the Base Body for Trapping Microorganisms or Cells (Second Embodiment)

A second embodiment of the manufacturing method of the invention will be described using the base body 20 as an example.

In this case, as shown in FIGS. 44A to 44E, the manufacturing method includes at least a process B1 (FIG. 44B) in which recess portions 63 and 64 or through holes that configure a well 67 and a first fluidic channel 68 that form the space (or a second fluidic channel 67 and a third fluidic channel 68 that form the space) are formed in a single member 69, a process B2 (FIG. 44C) in which modified regions 61 are formed in areas which form fine vacuum holes 65 in the single member 69 by irradiating, with the laser L having a pulse duration on the order of picoseconds or less, the areas, and a process B3 (FIG. 44D) in which the modified regions 61 are removed from the single member 69 through etching.

Examples of the material of the member 69 include silicon, glass, silica, sapphire, and the like.

The above materials are excellent in terms of the workability when forming the fine vacuum holes 65, which is preferable.

Among the above, the material is preferably an amorphous material that is not easily influenced by the working anisotropy determined by crystal orientations.

Furthermore, in a case in which glass, silica, or sapphire is employed as the material of the member 69, and the trapped microorganisms or cells T are optically observed using a microscope or the like, the above material is more suitable for the observation since the material transmits visible light (wavelength 0.36 μm to 0.83 μm).

In addition, the material of the member 69 preferably transmits at least some wavelengths of light from light having a wavelength of 0.1 μm to 10 μm.

Specifically, the material of the member 69 preferably transmits light in at least a partial range of a general wavelength range (0.1 μm to 10 μm) which are used as a working laser light beam.

In a case in which the material of the member 69 transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the trapped microorganisms or cells T visually through the single member.

Meanwhile, in the invention, the "transmission (being transparent)" refers to everything about a state in which transmitted light is obtained from the member by entering light into the member.

In FIGS. 44A to 44E, the single member 69 is a transparent glass substrate (hereinafter referred to as the glass substrate 69).

[Process B1]

The process B1 can be conducted in the same manner as for Process A2 in the first embodiment of the manufacturing method of the invention.

Figure 44A:
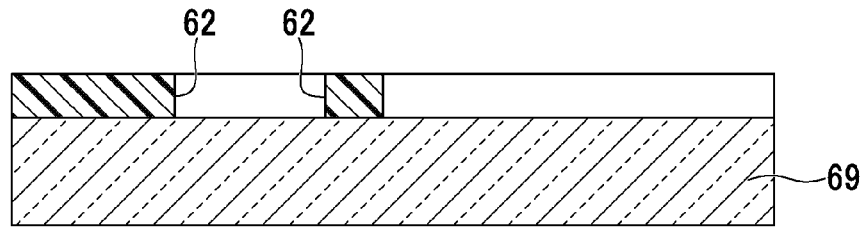
FIG. 44A is an outline cross-sectional view showing an example of the method of manufacturing the base body for trapping microorganisms or cells according to the invention.

That is, a resist 62 is patterned on the top surface of the glass substrate 69 through photolithography (FIG. 44A).

Figure 44B:
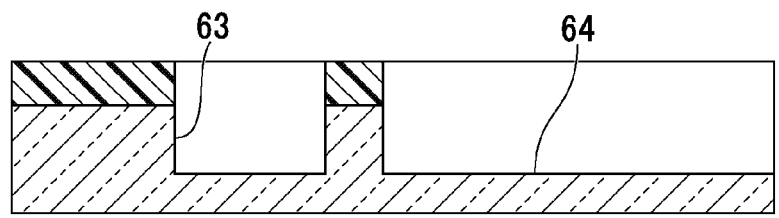
FIG. 44B is an outline cross-sectional view showing an example of the method of manufacturing the base body for trapping microorganisms or cells according to the invention.

Subsequently, areas in which the resist 62 is not patterned on the top surface of the glass substrate 69 are etched and removed to a desired depth using a method such as dry etching, wet etching, or sand blasting (FIG. 44B).

At the end, when the resist 62 which has become unnecessary is peeled off, the glass substrate 69 on which the first recess portion 63 and the second recess portion 64 are formed is obtained.

In the above example, a case in which the first recess portion 63 becomes the well 67, and the second recess portion 64 becomes the first fluidic channel 68 has been described.

In addition, in the process B1, fluidic channels may be formed in the substrate instead of forming the recess portions 63 and 64.

In this case, the first fluidic channel (the second fluidic channel and the third fluidic channel) may be formed by excavating areas that form the first fluidic channel and the second fluidic channel in the glass substrate 69 from the surface of the glass substrate 69 through drilling (laser drilling), combination of laser modification having a duration on the order of picoseconds or less, and selective etching, or the like so as to form through holes.

In addition, combinations of the excavating method using the drill and a variety of etching methods may be used.

[Process B2]

Figure 44C:
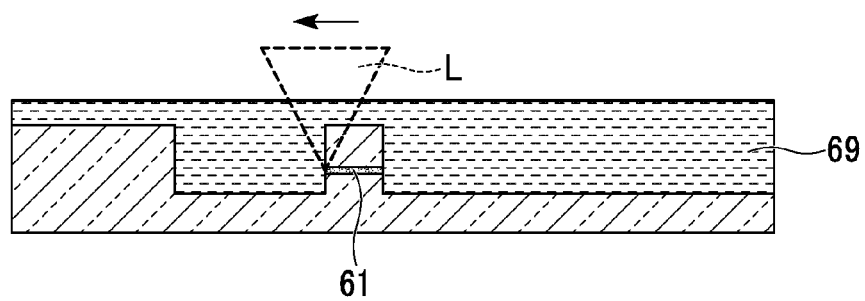
FIG. 44C is an outline cross-sectional view showing an example of the method of manufacturing the base body for trapping microorganisms or cells according to the invention.

Next, the modified regions 61 are formed in areas that form the fine vacuum holes 65 in the single glass substrate 69 by irradiating, with the laser L having a pulse duration on the order of picoseconds or less, the areas (FIG. 44C).

Specifically, the modified regions can be formed in the same manner as in Process A1 in the first embodiment of the manufacturing method of the invention.

At this time, in a case in which the modified regions 61 are formed at portions at which the modified regions are exposed to the side surface of the first recess portion 63 and the second recess portion 64 by irradiating with the laser L in a collective manner, the laser light L is more desirably irradiated through liquid immersion exposure (FIG. 44C).

It is possible to increase the accuracy of the shape of the modified regions 61 formed at the portions at which the modified regions are exposed to the side surfaces (the shape of the fine vacuum holes 65 at the end portions).

[Process B3]

Figure 44D:
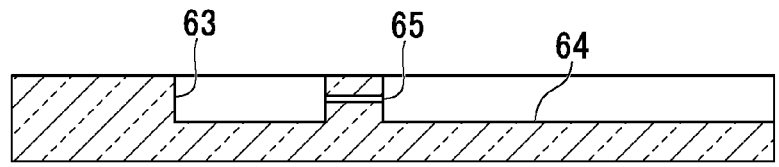
FIG. 44D is an outline cross-sectional view showing an example of the method of manufacturing the base body for trapping microorganisms or cells according to the invention.

Subsequently, the modified regions 61 formed in the process A2 are removed from the single glass substrate 69 through etching (FIG. 44D).

Wet etching is preferable as the etching method.

Since the modified regions 61 having the cross-section exposed at the side surfaces of the recess portions 63 and 64 (or the through holes) have a decreased etching resistance, selective or preferential etching is possible.

Specifically, the modified regions can be removed in the same manner as in Process A3 in the first embodiment of the manufacturing method of the invention.

As a result of the etching, it is possible to form the fine vacuum holes 65 having a diameter of the opening on the order of nanometers at predetermined locations in the glass substrate 69 so as to communicate the first recess portion 63 and the second recess portion 64.

Figure 44E:
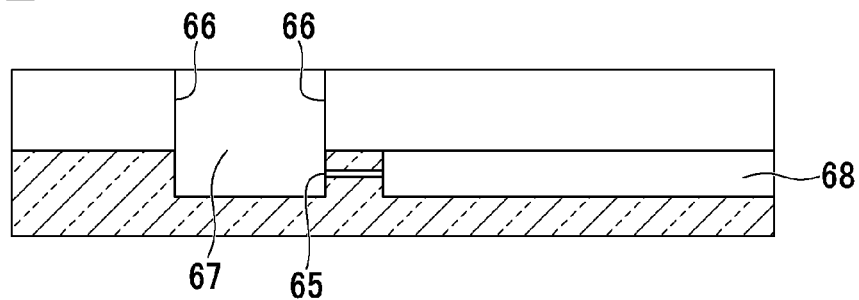
FIG. 44E is an outline cross-sectional view showing an example of the method of manufacturing the base body for trapping microorganisms or cells according to the invention.
Figure 45:
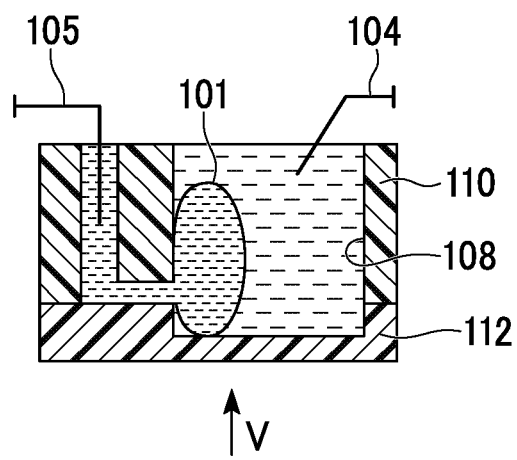
FIG. 45 is an outline cross-sectional view showing an example of an apparatus configuration which is used in the patch-clamp method of the related art.

Next, it is possible to form the first fluidic channel 68 by adhering a member 66 to the top surface of the glass substrate 69 so as to cover the formed second recess portion 64 (FIG. 44E).

The formed first recess portion 63 can be used as the well 67 as it is, and it is possible to appropriately adjust the depth of the well 67 by adhering the member 66 to the glass substrate 69 while the top surface of the well 67 is made to remain open as shown in FIG. 44E.

It is also possible to form the second fluidic channel 67 instead of the well 67 by adhering the member 66 to the top surface of the glass substrate 69 so as to cover the first recess portion 63 (not shown).

In this case, the first fluidic channel 68 can be differently referred to as the third fluidic channel 68.

As the method of adhering the member 66 and the top surface of the glass substrate 69, a well-known method may be conducted depending on the material of the member 66.

In addition, it is also possible to appropriate install electrodes, wires, and the like for an electrophysiological measurement in the first fluidic channel 68 during the adhering.

The material of the member 66 is not particularly limited, and it is possible to use a resin substrate such as PDMS or PMMA, or a glass substrate.

In addition, the material of the member 66 may be constituted by a material that does not transmit light (for example, visible light) used for observation.

In a case in which trapping of microorganisms or cells is the only object, the material does not necessarily need to transmit light that is used for observation.

When a member that transmits light used for observation is used, optical observation from the top surface becomes possible, which is preferable.

The member that is used to form the first fluidic channel 68 and covers the second recess portion 64 does not necessarily need to be a member that transmits light that is used for observation, and may be a member that does not transmits light that is used for observation.

First Embodiment of the Base Body for Forming a Lipid Membrane

[Base Body 10A-1]

Figure 46:
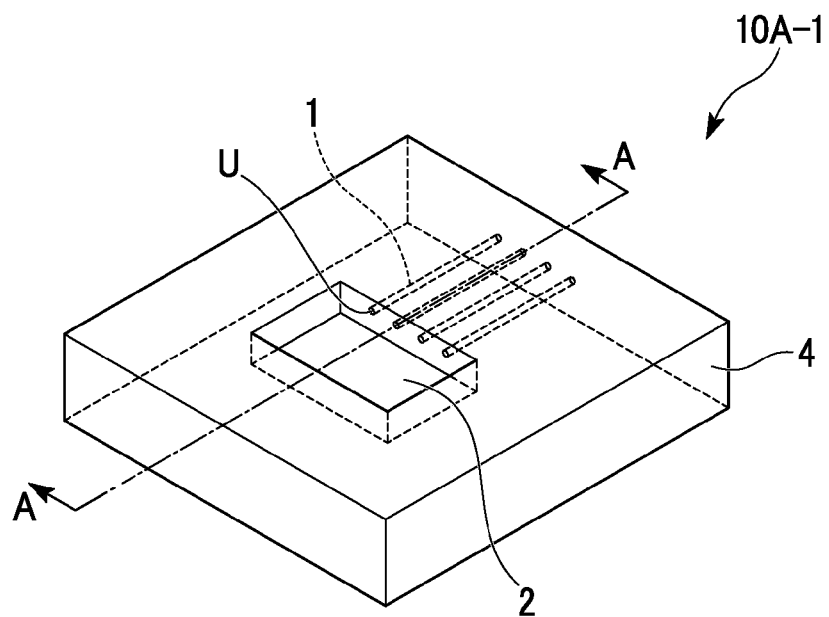
FIG. 46 is a schematic perspective view showing an example of a base body for forming a lipid membrane according to the invention.

FIG. 46 is a perspective view of a base body 10A-1 which is a first embodiment of a base body for forming a lipid membrane according to the invention (hereinafter sometimes referred to as simply the "base body").

Figure 47:
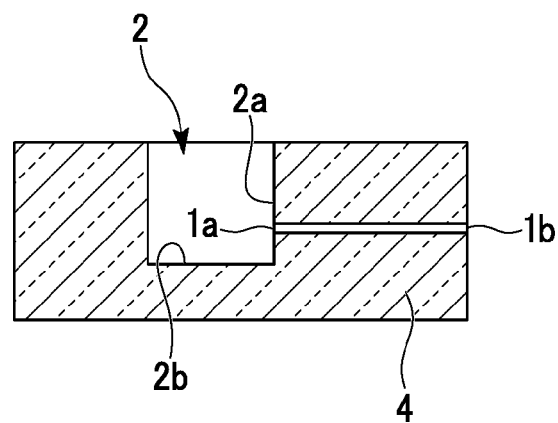
FIG. 47 is a cross-sectional view taken along the line A-A in FIG. 46.

FIG. 47 is a schematic view showing a cross-section taken along the line A-A in FIG. 46.

The base body 10A-1 is a base body having micropores 1 that form a lipid membrane.

The base body 10A-1 includes a space (well 2) which is provided in the base member 4 and allows a liquid P including lipids to flow in, and the micropores 1 that communicate the well 2 to the outside of the base member 4, and, at least portions that configure the micropores 1 in the base member 4 are formed of a single member.

Here, the sentence "the liquid P including lipids is made to flow into the space" means that the liquid P is fed into the space from the outside of the space.

The liquid P that has flowed in may be stopped and remain (or come to a halt) in the space, or may be allowed to flow out of the space.

In the latter case, a flow of the liquid P is generated in the space by continuously making the liquid P flow into the space.

The above action is applied to all the base bodies according to the invention.

In the base body 10A-1, the well 2 is provided on the top surface side of the base member 4.

The well 2 configures the space which allows the fluid including the lipids to flow in.

Opening portions U at which the first end portions 1a of the micropores 1 are exposed are formed on the side surface 2a of the well 2.

At least some of the top surface or bottom surface 2b of the well 2 is opened or constituted by a transparent member (not shown) so that the lipid membrane M formed at the opening portions U can be optically observed.

In addition, at least portions that configure the micropores 1 in the base body 10A-1 are formed of a single member.

If the micropores 1 are opened on the side surface 2a of the well 2 as described above, since the formation process of the lipid membrane M can be easily observed from the side surface of the well 2 by observing it from the top surface of the base body 10A-1, control becomes easy during the formation of the lipid membrane M.

Alternatively, it is also possible to observe the lipid membrane M formed at the opening portions U from an inclined angle with respect to the side surface 2a.

In the invention, the lipid included in the liquid P is not particularly limited, and examples thereof include phospholipid which is a lipid included in a cell membrane.

Examples of the phospholipid include phosphatidylcholine, phosphatidylserine, phosphatidylethanolamine, and the like.

When the above amphipathic lipid is used, it is possible to form the lipid membrane M having a lipid bilayer membrane structure at the opening portions U of the micropores 1.

At this time, when cholesterol is added as a lipid component, there are cases in which the strength of the lipid membrane increases.

In the invention, the solvent that dissolves the lipids included in the liquid P is not particularly limited as long as the solvent can dissolve the lipids, but a solvent that mixes with water is not preferable.

The lipid membrane M can be easily formed.

Examples of the above solvent include organic solvents such as hexadecane and fat and oil such as squalene.

In the base body 10A-1 shown in FIG. 46, the single member configures not only the micropores 1 but also the entire base member 4.

Examples of the material of the single member include silicon, glass, silica, sapphire, and the like.

The above materials are excellent in terms of the workability when forming the micropores 1, which is preferable.

Among the above, the material is preferably an amorphous material that is not easily influenced by the working anisotropy determined by crystal orientations.

Furthermore, in a case in which glass, silica, or sapphire is employed as the material of the single member, and the trapped microorganisms or cells T are optically observed using a microscope, the above material is more suitable for the observation since the material transmits visible light (wavelength 0.36 µm to 0.83 µm).

Since the above materials do not absorb the solvent, changes in the diameter of the opening of the opening portions or changes in the volume of the micropores do not occur when forming a lipid membrane.

The above fact is a decisively important element in a case in which the opening portions U of the micropores 1 are formed at a unit (nm) of a nanometer scale.

When absorbing the solvent so as to expand, the opening portions U on the nanometer scales easily close.

Since the shape or size of the opening portion U does not change so that there is no case in which the size of a formed lipid membrane changes in each experiment, experiments with high reproducibility is possible.

In a case in which the material that configures the opening portion U absorbs the solvent and expands, it is difficult to form the opening portions U on the nanometer scale.

However, it is possible to form the opening portions U at a unit (µm) of the micrometer scale.

The opening portion U of the micropore 1 of the invention is constituted by a single member having no adhered surface.

That is, the periphery of the opening portion U is constituted by a member having the same coefficient of linear expansion.

Therefore, even in a case in which an abrupt change in the temperature at locations near the opening portions U which may be caused when the operation temperature of the base body 10A-1 changes or a liquid having a different temperature from the temperature of the base body 10A-1 is made to flow into the space 2 (the well 2), there is no concern that the opening portions U may rupture at the adhered surfaces.

Furthermore, since the opening portions U do not have adhered surfaces, the chemical resistance of the opening portions U with respect to chemicals is also high.

Therefore, it is possible to use a chemical which may corrode the adhered surfaces.

In addition, in a case in which the formed lipid membrane is observed using an optical microscope or the like, when the opening portion U has an adhered surface, there are cases in which light is reflected on the adhered surface so as to cause hindrance of the observation.

Since the opening portions U of the micropores 1 of the invention are formed of a single member having no adhered surface, there is no concern that reflected light which may hinder observation are generated.

In addition, the material of the member preferably transmits at least some wavelengths of light from light having a wavelength of 0.1 µm to 10 µm.

Specifically, the material of the single member preferably transmits light in at least a partial range of a general wavelength range (0.1 µm to 10 µm) which are used as a working laser light beam.

In a case in which the material of the single member transmits the above laser light, it is possible to form the modified region by irradiating, with the laser, the member as described below.

In addition, the single member more preferably transmits light in the visible light range (approximately 0.36 µm to approximately 0.83 µm).

In a case in which the single member transmits light in the visible light range, it is possible to easily observe the formed lipid membrane M optically through the single member using an optical microscope or the like.

Meanwhile, in the invention, the "transmission (being transparent)" refers to everything about a state in which transmitted light is obtained from the member by entering light into the member.

In FIG. 46, the single member that configures the base member 4 is a transparent glass substrate.

As shown in FIG. 47, the micropores 1 communicate the well 2 to the outside of the base member 4.

First end portions 1a of the micropores 1 are exposed (opened) at the side surface 2a of the well 2, and form the opening portions U.

Second end portions 1b of the micropores 1 are exposed at a side surface of the base member 4.

In the invention, when the micropores 1 communicate the space (well 2) to the outside of the base member 4, the second end portions 1b of the micropores 1 may be exposed and opened at the side surface (outside) of the base member 4 like the base body 10A-1 of FIG. 46.

Furthermore, for example, as a micropore 31α in the base body (FIG. 69) described below, the second end portion of the micropore 31α may be opened to a first fluidic channel 33α, and be communicated to the outside of the base member 34 through the first fluidic channel 33α.

In addition, the fluidic channel that communicates to the outside is not limited to the first fluidic channel 33α, and the second end portion may be communicated to the outside of the base member 34 through other paths (for example, fluidic channels, wells, and the like).

The meaning of "the fine vacuum holes that communicate the space and the outside of the base member" described herein is applied to all the base bodies according to the invention.

Examples of the method of forming the lipid membrane M at the opening portions U in the base body of the invention include the following method.

Figure 48A:
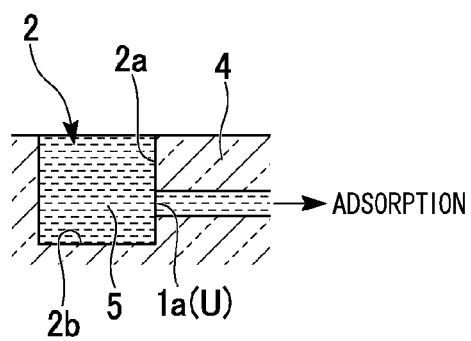
FIG. 48A is a schematic cross-sectional view showing an example of a method of forming a lipid membrane in the base body according to the invention.

Firstly, a buffer solution 5 such as a physiological saline solution or a pH buffer solution is fed into the well 2 (space 2), and the buffer solution 5 is made to flow into the micropores 1 from the second end portion 1b of the micropores 1 through an adsorption portion such as a syringe or pump (not shown) (FIG. 48A).

At this time, there are cases in which the buffer solution 5 does not flow out of the other end portion 1b as the pore diameter of the micropores 1 decreases.

In this case, it becomes necessary to make, for example, a liquid having a small capillary force such as ethanol flow in from the well 2 (space 2) in advance, discharge the liquid through the other end portion 1b, and then substitute the liquid with the buffer solution 5.

Subsequently, the buffer solution 5 is removed from the well 2 using a pipet or the like (not shown).

Figure 48B:
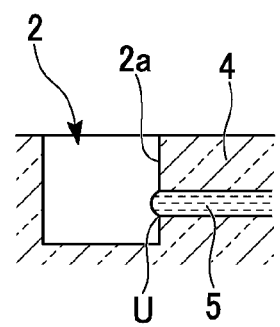
FIG. 48B is a schematic cross-sectional view showing an example of the method of forming a lipid membrane in the base body according to the invention.

At this time, the buffer solution 5 in the micropores 1 exposes the water surfaces at the opening portions U due to the surface tension (FIG. 48B).

Next, the liquid P including the lipid is made to flow into the well 2, and the liquid P and the water surfaces of the buffer solution 5 are brought into contact at the opening portions U.

At this time, the lipid molecules included in the liquid P attach polar portions in the molecules to the water surfaces of the buffer solution 5 toward the buffer solution 5 side.

Figure 48C:
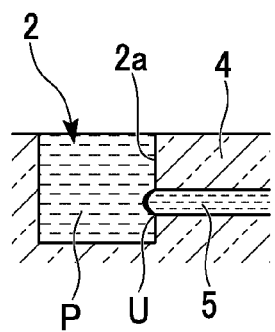
FIG. 48C is a schematic cross-sectional view showing an example of the method of forming a lipid membrane in the base body according to the invention.

Thereby, the water surfaces of the buffer solution 5 are covered with the lipid molecules (FIG. 48C).

Figure 48D:
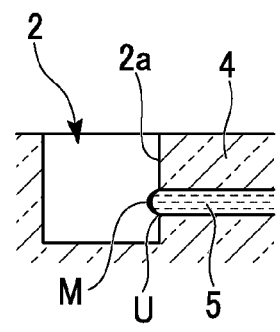
FIG. 48D is a schematic cross-sectional view showing an example of the method of forming a lipid membrane in the base body according to the invention.

After that, when the liquid P is removed from the well 2 using a pipet or the like, the lipid membrane M formed of the attached lipid molecules is formed on the water surfaces of the buffer solution 5 remaining in the opening portions U (FIG. 48D).

Figure 48E:
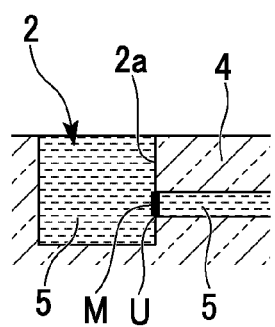
FIG. 48E is a schematic cross-sectional view showing an example of the method of forming a lipid membrane in the base body according to the invention.

Furthermore, when the buffer solution 5 is made to flow into the well 2, a state in which the buffer solution 5 in the well 2 and the buffer solution 5 in the micropores 1 are isolated through the lipid membrane M at the opening portions U is formed (FIG. 48E).

The lipid membrane M in the above state can have at least one of a lipid bilayer membrane structure formed of the lipid molecules and a single layer lipid membrane structure formed of the lipid molecules.

Figure 48F:
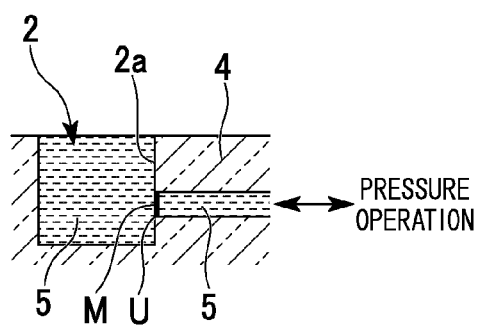
FIG. 48F is a schematic cross-sectional view showing an example of the method of forming a lipid membrane in the base body according to the invention.

In this state, it is possible to control the thickness of the lipid membrane M by carrying out an operation that increases or decreases pressure in the buffer solution 5 in the micropores 1 using a syringe or a pump, and it is also possible to form a lipid bilayer membrane structure (FIG. 48F).

During the above pressure operation, the well 2 is preferably closed.

Thereby, it is possible to cause a sufficient change in pressure in the lipid membrane M.

The micropores 1 are formed in the single glass substrate 4, and are through holes having no seam or adhered surface.

Naturally, there is no seam or adhered surface in the opening portions U at the end portion of the micropores.

Therefore, the attaching force between the lipid membrane M and the opening portions U is sufficiently increased.

In addition, since the micropores 1 and the peripheral portions of the micropores 1 are formed of the single glass substrate 4, and are through holes having no seam or adhered surface, peeling or breakage in the adhered surfaces does not occur due to the deformation or chemical-induced damage of the glass substrate 4.

Therefore, even when heating sterilization or chemical sterilization is repeatedly conducted on the glass substrate 4, there is no case in which the glass substrate 4 is broken.

The above fact can be said to be a particularly excellent characteristic for base bodies that form a lipid membrane on which heating sterilization or chemical sterilization needs to be conducted on a routine basis.

Furthermore, since no difference in refractive index is caused in locations near the micropores 1, it is easier to condense light from the opening portion U.

Therefore, it is possible to easily observe the formed lipid membrane M.

Here, the "opening portion U" refers to an area at which the first end portion 1a of the micropore 1 is opened, and the lipid membrane M is formed in the side surface 2a of the well 2.

The shape of the hole of the first end portion 1a of the micropore 1 which configures the opening portion U at the side surface 2a of the well 2 may be any shape, and it is possible to form, for example, a circular shape or a substantially circular shape, an oval shape or a substantially oval shape, a rectangle, or a triangle.

In a case in which the shape of the hole is circular or substantially circular, the diameter or major axis is preferably in a range of 0.02 µm to 5 µm.

In addition, in the formed lipid membrane M, the diameter or major axis is more preferably in a range of 0.02 µm to 5 µm even in a case in which an electric physiological measurement is conducted using the patch-clamp method.

It is possible to carry out a more accurate electrophysiological measurement by forming the lipid membrane M having a smaller area.

Therefore, the diameter or major axis is more preferably in a range of 0.02 µm to 3 µm.

When the diameter or major axis is less than the lower limit value of the above range, there is a concern that the area of the opening portion U may be too small such that the lipid membrane M is not appropriately formed.

When the diameter or major axis exceeds the upper limit value of the range, there is a concern that the sealing properties between the micropores 1 and the lipid membrane M may decrease such that it is not possible to form lipid membrane that is stabilized for a long period of time.

It becomes possible to form lipid membrane having a smaller size than in the related art by highly accurately processing the pore diameter of the micropores on the order of nanometers, and it becomes possible to observe the functions of a membrane protein material which was observed as a collection of a plurality of molecules in the related art at a single molecular level.

As a result, the invention can be means for confirming a variety of molecular characteristics of a membrane protein material which thus far has not been explained.

Furthermore, since the stabilized sealing properties between the lipid membrane and the opening portions are realized by decreasing the diameter of the opening portions of the holes when the electrophysiological characteristics of the membrane protein material introduced into the lipid membrane are measured, it is possible to stably carry out the measurement of electrophysiological characteristics.

In FIG. 47, the micropore 1 is formed so as to be substantially perpendicular to the side surface 2a of the well 2.

However, the micropores do not necessarily need to be substantially perpendicular to the side surface, and can be freely disposed in the single glass substrate 4 in accordance with the design of the base body 10A-1.

A plurality of micropores 1 may be disposed in the base body 10A-1.

Since each of the micropores 1 has the opening portion U, it is possible to form a plurality of lipid membranes M.

When a plurality of micropores 1 are disposed in a single well 2, it is possible to separately control the suction at the micropores 1 by connecting an independent sucking portion (not shown) such as a syringe or a pump to the second end portion 1b of the micropore 1.

Therefore, it is possible to independently control the formation and maintenance of the lipid membrane M at the micropores 1.

When the material of the base member 4 is silicon, glass, silica, sapphire, or the like, since the materials are excellent in terms of workability, it is possible to tightly dispose a plurality of micropores 1.

In the base body 10A-1, the bottom surface 2b of the well 2 is constituted by the base member 4 including a glass substrate.

The top surface of the well 2 which is opposite to the bottom surface 2b is opened, and has no lid.

Therefore, it is possible to observe the lipid membrane M formed at the opening portions U from at least one of the bottom surface 2b and top surface using an optical observation portion such as a microscope or the like.

Meanwhile, it is not a definite requirement that the top surface have no lid, and the top surface may be covered with a lid including a member such as a plastic, resin, or glass member (not shown).

Since it is possible to form the lipid membrane M at the opening portions U while observing the lipid membrane, it is possible to appropriately adjust the sucking force in accordance with the state of the lipid membrane M.

In a case in which an electrophysiological measurement of the formed lipid membrane M is conducted, for example, electrodes (not shown) may be disposed respectively in the well 2 and the micropore 1b side.

Alternatively, external electrodes may be used through the buffer solution or the like.

Since the opening portion U is formed of the single glass substrate 4, it is possible to form high resistance sealing with respect to the lipid membrane M.

Therefore, the well-known patch-clamp method of the related art can be applied.

At this time, it is possible to carry out a more highly accurate electrophysiological measurement than in the related art by making the diameters of the openings of the holes on the first end portion 1a side of the micropores 1 that configure the opening portions U be smaller than the diameter of the opening (approximately 2 µm to 4 µm) of the hole of a patch pipet or the like of the related art.

[Base body 10B-1]

An embodiment of the base body for forming a lipid membrane of the invention is also shown in a base body 10B-1 of FIG. 49.

In the base body 10B-1, the fluidic channel 3 is provided on the top surface side of the base member 4.

The fluidic channel 3 is a space which allows the liquid P including the lipid to flow in and circulate.

Compared to the well 2 in the base body 10A-1, the fluidic channel 3 in the base body 10B-1 can allow a larger amount of the liquid P to flow in and circulate.

In addition, there is an advantage that liquids are easily exchanged at the fluidic channel 3 (space 2).

As described in the above method of forming the lipid membrane M, the operation in which a plurality of liquids such as the buffer solution 5 and the liquid P including the lipid are sequentially brought into contact with the opening portions U becomes easier.

Other configurations of the base body 10B-1 are the same as in the base body 10A-1.

[Base Body 10C-1]

Figure 50:
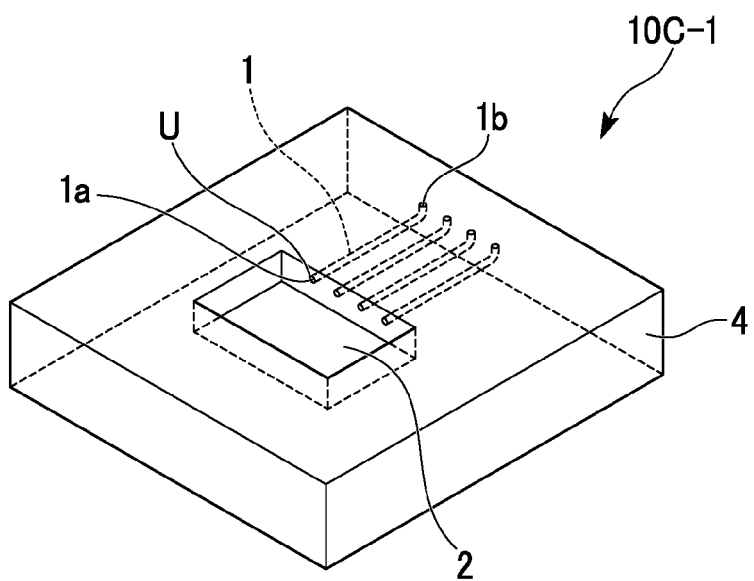
FIG. 50 is a schematic perspective view showing an example of the base body for forming a lipid membrane according to the invention.

An embodiment of the base body for forming a lipid membrane of the invention is also shown in a base body 10C-1 of FIG. 50.

In the base body 10C-1, the second end portions 1b of the micropores 1 are provided on the top surface side of the base member 4.

That is, the second end portions 1b of the micropores 1 can be provided on an arbitrary surface in addition to the side surface of the base member 4.

Other configurations of the base body 10C-1 are the same as in the base body 10A-1.

[Base body 10D-1]

Figure 51:
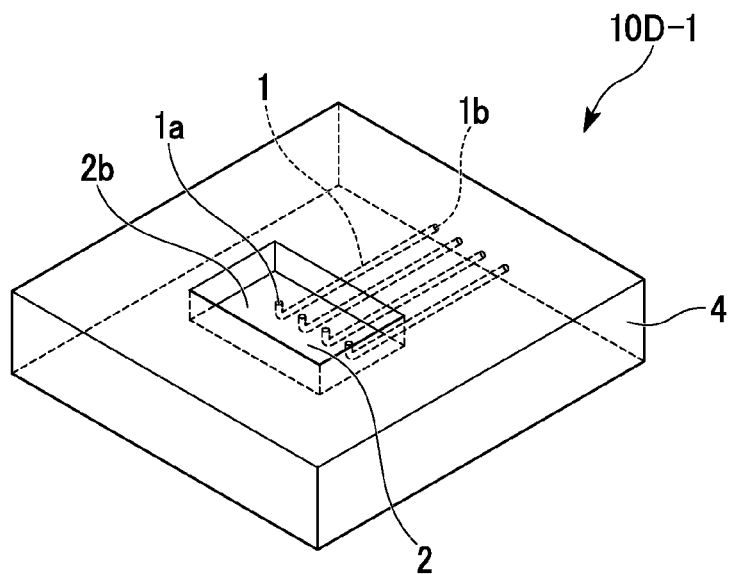
FIG. 51 is a schematic perspective view showing an example of the base body for forming a lipid membrane according to the invention.

An embodiment of the base body for forming a lipid membrane of the invention is also shown in a base body 10D-1 of FIG. 51.

In the base body 10D-1, the opening portions including the first end portions 1a of the micropores 1 are provided on the bottom surface 2b of the well 2.

That is, the first end portions 1a of the micropores 1 can be provided on an arbitrary surface in addition to the side surface of the well 2 that configures the space.

In a case in which the opening portions are provided on the bottom surface (base surface) of the space, there is an advantage of easy observation of the lipid membrane M formed at the opening portions from the top surface.

Other configurations of the base body 10D-1 are the same as in the base body 10A-1.

[Base body 10E-1]

Figure 52:
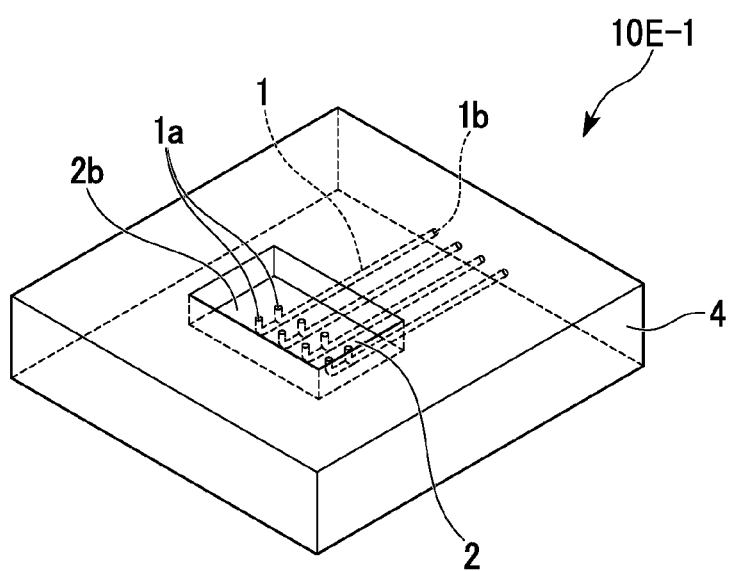
FIG. 52 is a schematic perspective view showing an example of the base body for forming a lipid membrane according to the invention.

An embodiment of the base body for forming a lipid membrane of the invention is also shown in a base body 10E-1 of FIG. 52.

In the base body 10E-1, the first end portions 1a of the micropores 1 are provided on the bottom surface 2b of the well 2.

At this time, the first end portion 1a of each of the micropores 1 is branched into two parts so that twice as many of the opening portions are formed on the bottom surface 2b of the well 2 as the second end portions 1b.

That is, the first end portions 1a of the micropores 1 may be branched and opened at a plurality of locations in the space.

This configuration can dispose a number of opening portions in the space, which makes it possible to form a larger number of lipid membranes M.

In addition, it is possible to dispose as many of the first end portions 1a as many as desired apart from the same number of or twice as many as the second end portions 1b.

Other configurations of the base body 10E-1 are the same as in the base body 10A-1.

[Base body 10E-1]

Figure 53:
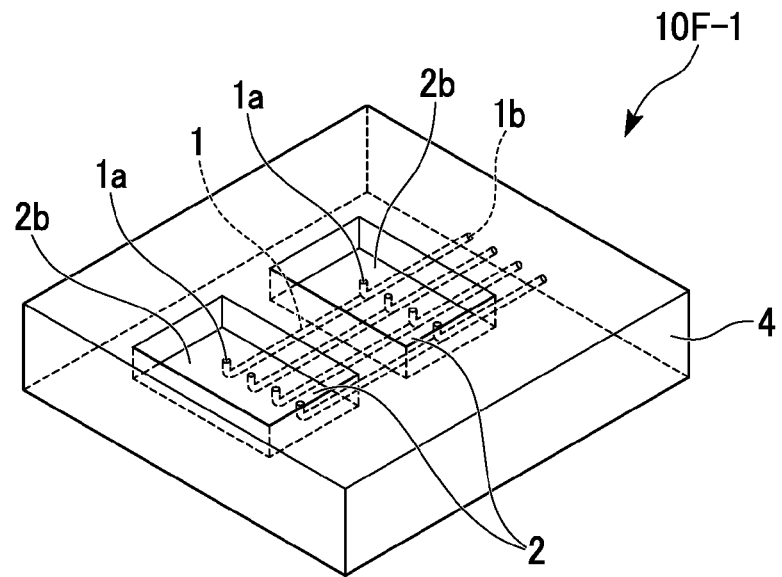
FIG. 53 is a schematic perspective view showing an example of the base body for forming a lipid membrane according to the invention.

An embodiment of the base body for forming a lipid membrane of the invention is also shown in a base body 10E-1 of FIG. 53.

In the base body 10E-1, two wells 2 are disposed on the top surface of the base member 4, and the branched first end portions 1a of the micropores 1 are disposed in each of the wells 2.

Since the configuration having two wells 2 can allow a liquid P that is different from the liquid in the well 1 to flow into the respective wells 2, the configuration is suitable for a multi-detection subject treatment.

The number of the wells 2 is not limited to 1 or 2, and as many as desired can be disposed.

Other configurations of the base body 10F-1 are the same as in the base body 10A-1.

[Base body 10G-1]

Figure 54:
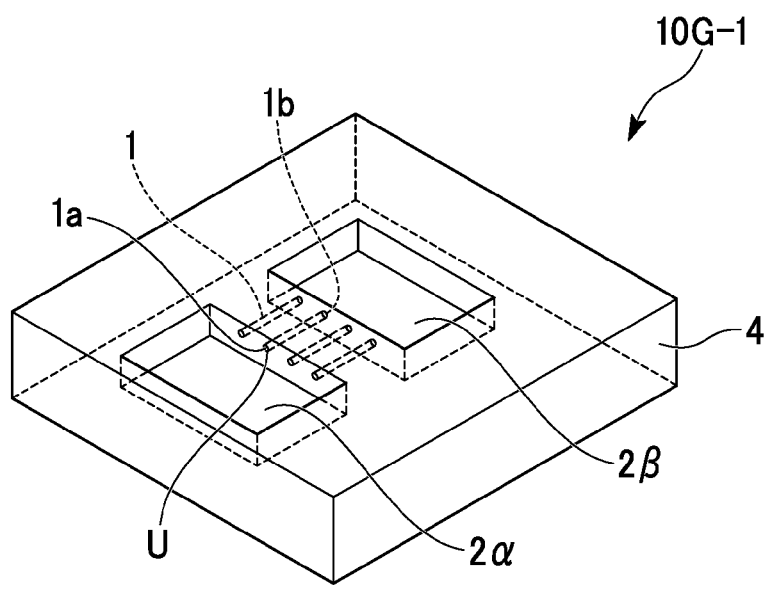
FIG. 54 is a schematic perspective view showing an example of the base body for forming a lipid membrane according to the invention.

An embodiment of the base body for forming a lipid membrane of the invention is also shown in a base body 10G-1 of FIG. 54.

In the base body 10G-1, two wells 2α and 2β are disposed on the top surface of the base member 4, and the first end portions 1a and the second end portions 1b of the micropores 1 are disposed respectively on the side surfaces of the respective wells 2.

In this case, the liquid P including the lipid is made to flow into the wells 2a to which the first end portions 1a are open.

In contrast to the above, the sucking portions are directly or indirectly connected separately to the wells 2β to which the second end portions 2b are open.

In this case, it is possible to pull the liquid P which has flowed into the well 2α to the well 2β side by forming a negative pressure in the well 2β.

Therefore, it is possible to form the lipid membrane M at the opening portions U including the first end portions 1a which are open to the side surface of the well 2α using, for example, the above method of forming the lipid membrane M.

That is, it is also possible to provide the second end portions 1b of the micropores 1 on the side surface of a recess portion (well 2β) provided on the top surface of the base member 4 as described above in addition to on the side surface or one surface of the base member.

In addition, the number of the wells is not limited to 2, and as many as desired can be disposed.

Other configurations of the base body 10G-1 are the same as in the base body 10A-1.

Meanwhile, it is not a definite requirement that the wells 2 or the fluidic channel 3 in the base bodies 10A-1 to 10G-1 have no lid, and a lid may be appropriately provided (not shown).

There are cases in which it becomes easy to hold the liquid P in the well 2, or the circularity of the liquid P in the fluidic channel 3 is enhanced in accordance with provision of the lid.

In addition, when the pressure operation is conducted with respect to the lipid membrane M formed at the opening portions U, the fluidic channel 3 is preferably closed.

Thereby, it is possible to cause a sufficient change in pressure in the lipid membrane M.

[Base Body 10H-1]

Figure 55:
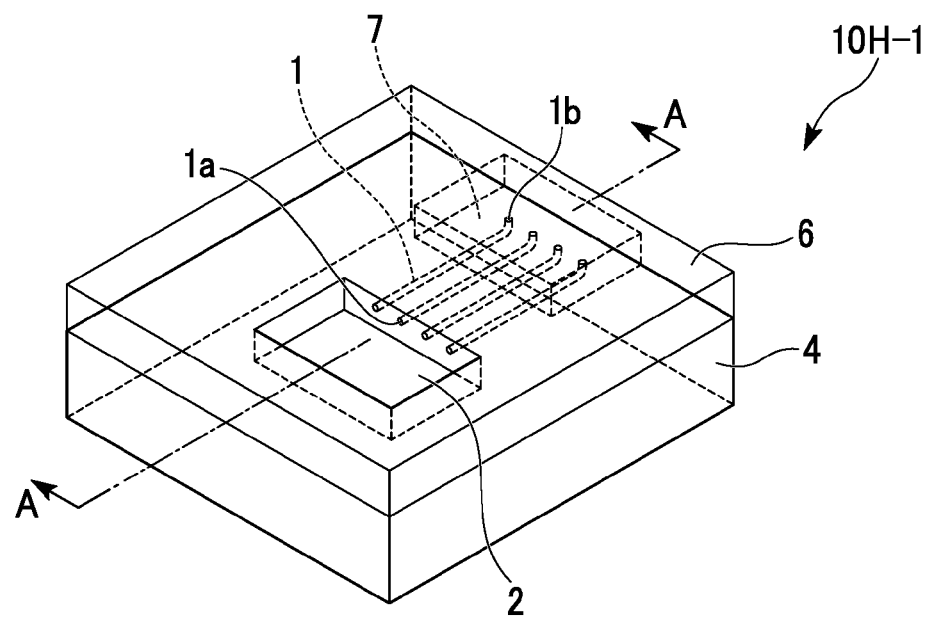
FIG. 55 is a schematic perspective view showing an example of the base body for forming a lipid membrane according to the invention.

An embodiment of the base body for forming a lipid membrane of the invention is also shown in a base body 10H-1 of FIG. 55.

Figure 56:
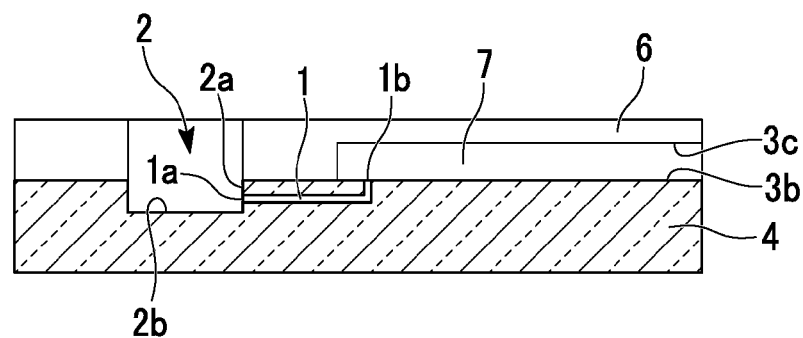
FIG. 56 is a cross-sectional view taken along the line A-A in FIG. 55.

FIG. 56 is a schematic view showing the cross-section taken along the line A-A in FIG. 55.

The base body 10H-1 is formed by adhering the substrate 6 to the top surface of the base member 4 in the configuration of the above base body 10C-1.

The well 2 is provided on the top surface of the base member 4.

In the substrate 6, a location opposite to the well 2 is hollowed out, penetrated, and opened to the top surface.

According to the above configuration, it is possible to increase the volume of the well 2 as much as the thickness of the substrate 6, and the amount of the liquid P which flows into the well can be increased.

In addition, the second end portions 1b of the micropores 1 are disposed on the top surface of the base member 4.

In the substrate 6, the fluidic channel 7 is provided at a location opposite to the second end portions 1b.

According to the above configuration, it is possible to pull and suction the liquid P in the well 2 to the fluidic channel 7 through the micropores 1 by directly or indirectly connecting the suctioning portions to the fluidic channel 7.

Therefore, it is possible to form the lipid membrane M at the opening portions U in the first end portions 1a of the micropores 1 using, for example, the above method of forming the lipid membrane M.

In a case in which the substrate 6 is formed of a transparent member, observation is possible from any of the top surface side and the bottom surface side.

Other configurations of the base body 10H-1 are the same as in the base body 10A-1.

The material of the substrate 6 is not particularly limited, and examples thereof include resin substrates such as PDMS and PMMA, silicon substrates, and glass substrates.

In a case in which the substrate is formed of the same material as for the base member 4, it is possible to easily adhere the substrate and the base member.

The base member 4 and the substrate 6 may be adhered using a well-known method.

[Base body 10I-1]

Figure 57:
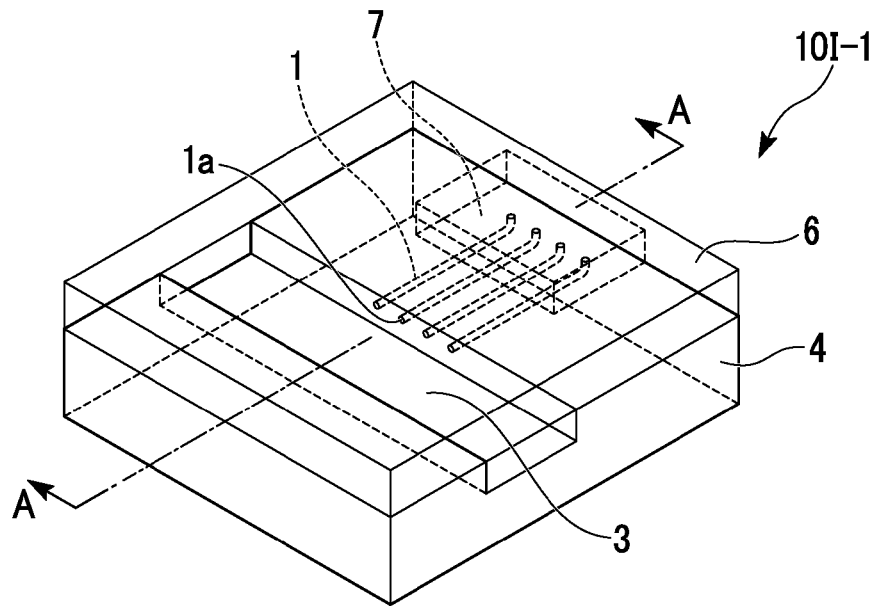
FIG. 57 is a schematic perspective view showing an example of the base body for forming a lipid membrane according to the invention.

An embodiment of the base body for forming a lipid membrane of the invention is also shown in a base body 10I-1 of FIG. 57.

Figure 58:
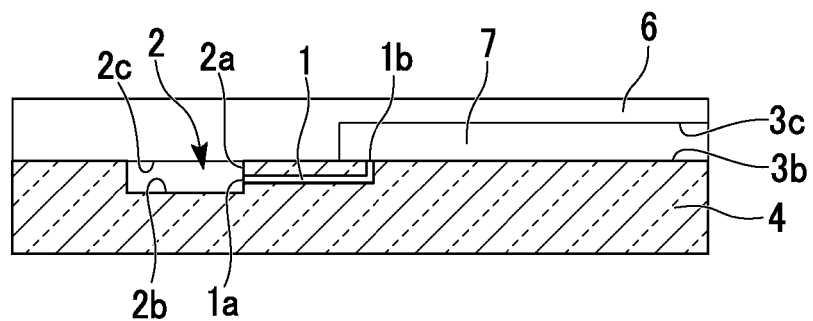
FIG. 58 is a cross-sectional view taken along the line A-A in FIG. 57.

FIG. 58 is a schematic view showing the cross-section taken along the line A-A in FIG. 57.

The base body 10I-1 is formed by adhering the substrate 6 to the top surface of the base member 4 in the configuration of the above base body 10B-1.

The fluidic channel 3 is provided on the top surface of the base member 4.

According to the above configuration, the buffer solution and the liquid P including the lipid are made to sequentially flow into and circulate in the fluidic channel 3.

In addition, the second end portions 1b of the micropores 1 are disposed on the top surface of the base member 4.

In the substrate 6, the fluidic channel 7 is provided at a location opposite to the second end portions 1b.

According to the above configuration, it is possible to pull and suction the liquid P in the fluidic channel 3 to the fluidic channel 7 through the micropores 1 by directly or indirectly connecting the sucking portions to the fluidic channel 7.

Therefore, it is possible to form the lipid membrane M at the opening portions U in the first end portions 1a of the micropores 1 using, for example, the above method of forming the lipid membrane M.

Other configurations of the base body 10I-1 are the same as in the base body 10B-1.

The material of the substrate 6 is not particularly limited, and examples thereof include resin substrates such as PDMS and PMMA, silicon substrates, and glass substrates.

In a case in which the substrate is formed of the same material as for the base member 4, it is possible to easily adhere the substrate and the base member.

The base member 4 and the substrate 6 may be adhered using a well-known method.

Second Embodiment of a Base Body for Forming a Lipid Membrane

Figure 59:
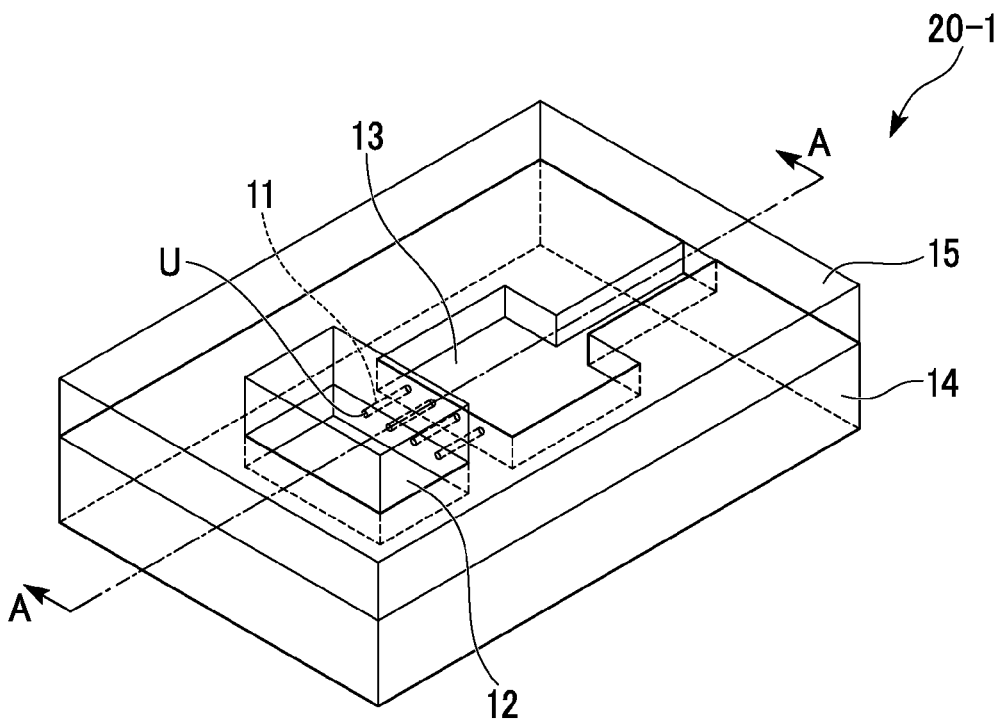
FIG. 59 is a schematic perspective view showing an example of the base body for forming a lipid membrane according to the invention.

FIG. 59 is a perspective view of a base body 20-1 which is a second embodiment of a base body for forming a lipid membrane according to the invention.

Figure 60:
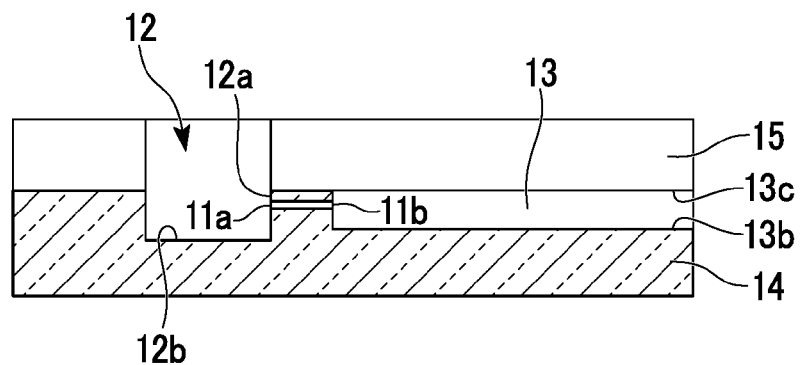
FIG. 60 is a cross-sectional view taken along the line A-A in FIG. 59.

FIG. 60 is a schematic view showing a cross-section taken along the line A-A in FIG. 59.

The base body 20-1 is a base body for forming a lipid membrane which has the micropores 11 that form the lipid membrane M.

The base body 20-1 includes at least the well 12 that configures a space present in the base member 14 which allows the liquid P including the lipids to flow in, the first fluidic channel 13 in which a negative pressure can be formed, and the micropores 11 that communicate between the well 12 and the first fluidic channel 13.

The micropores 11 communicate to the outside of the base member 14 through the first fluidic channel 13.

The opening portions U through which the first end portions 11a of the micropores 11 are exposed are formed at the side surface 12a of the well 12, and at least a part of the top surface or bottom surface 12b of the well 12 is opened or constituted by a transparent member (not shown) so that the lipid membrane M formed at the opening portions U can be optically observed.

At least the portions that configure the micropores 11 in the base member 14 are formed of a single member.

In the base body 20-1 shown in FIG. 59, the single member configures not only the micropores 11 but also the entire base member 14.

Examples of the material of the single member include silicon, glass, silica, sapphire, and the like.

The above materials are excellent in terms of the workability when forming the micropores 11, which is preferable.

Among the above, the material is preferably an amorphous material that is not easily influenced by the working anisotropy determined by crystal orientations.

Furthermore, in a case in which glass, silica, or sapphire is employed as the material of the single member, and the lipid membrane M are optically observed using a microscope, the above material is more suitable for the observation since the material transmits visible light (wavelength 0.36 μm to 0.83 μm).

In addition, the material of the member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the material of the single member transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the formed lipid membrane M visually through the single member.

Meanwhile, in the invention, the "transmission (being transparent)" refers to everything about a state in which transmitted light is obtained from the member by entering light into the member.

In FIG. 59, the single member that configures the base member 14 is a transparent glass substrate.

As shown in FIG. 60, the micropores 1 communicate the well 12 and the first fluidic channel 13.

The first end portions 11a of the micropores 11 are exposed (opened) at the side surface 12a of the well 12, and form the opening portions U.

The second end portions 11b of the micropores 11 are exposed at a side surface of the first fluidic channel 13.

The micropores 11 are formed in the single glass substrate 4, and are through holes having no seam or adhered surface.

Naturally, there is no seam or adhered surface in the opening portions U at the end portion of the micropores.

Here, the "opening portion U" refers to an area at which the first end portion 11a of the micropore 11 is opened, and the lipid membrane M is formed in the side surface 12a of the well 12.

The shape of the hole of the first end portion 11a of the micropore 11 which configures the opening portion U at the side surface 12a of the well 12 may be any of a rectangle, a triangle, an oval, and a circle.

When the diameter or major axis of the hole is in a range of 0.02 μm to 5 μm, it is possible to easily form the lipid membrane M.

In addition, in the formed lipid membrane M, the minor axis is preferably in a range of 0.02 μm to 5 μm even in a case in which an electric physiological measurement is conducted using the patch-clamp method.

It is possible to carry out a more accurate electrophysiological measurement by forming the lipid membrane M having a smaller area.

Therefore, the diameter or major axis is more preferably in a range of 0.02 μm to 3 μm.

When the diameter or major axis is less than the lower limit value of the above range, there is a concern that the area of the opening portion U may be too small such that the lipid membrane M is not appropriately formed.

When the diameter or major axis exceeds the upper limit value of the range, there is a concern that the sealing properties between the micropores 11 and the lipid membrane M may decrease such that it is not possible to form lipid membrane that is stabilized for a long period of time.

In FIG. 60, the micropore 11 is formed so as to be substantially perpendicular to the side surface 12a of the well 12.

However, the micropores do not necessarily need to be substantially perpendicular to the side surface, and can be freely disposed in the single glass substrate 14 in accordance with the design of the base body 20-1.

A plurality of micropores 11 may be disposed in the base body 20-1.

Since each of the micropores 11 has the opening portion U, it is possible to form a plurality of lipid membranes M.

The bottom surface 12b of the well 12 is constituted by the glass substrate 14.

The top surface of the well 12 which is opposite to the bottom surface 12b is opened, and has no lid.

It is possible to observe the lipid membrane M formed at the opening portions U from at least one of the bottom surface 12b and top surface using the optical observation portion such as a microscope or the like.

Meanwhile, it is not a definite requirement that the top surface have no lid, and the top surface may be covered with a lid including a member such as a plastic, resin, or glass member (not shown).

The bottom surface 13b of the first fluidic channel 13 is constituted by the glass substrate 14, and the top surface 13c of the first fluidic channel 13 is constituted by the member 15 such as plastic or glass.

Thereby, the first fluidic channel 13 forms a space in a half-sealed state.

The second end portions 11b of the micropores 11 are exposed and opened on the upstream of the first fluidic channel 13.

A negative pressure portion such as a syringe or a pump which can form a negative pressure in the first fluidic channel 13 is provided on the downstream of the first fluidic channel 13 (not shown).

Therefore, the liquid P which has flowed in from the top surface of the well 12 is pulled into the first fluidic channel 3 through the micropores 11 by forming a negative pressure in the first fluidic channel 13.

Therefore, it is possible to form the lipid membrane M at the opening portions U in the first end portions 1a of the micropores 11 using, for example, the above method of forming the lipid membrane M.

As shown in FIG. 60, some of the side surface 12a of the well 12 may be constituted by the member 15.

Thereby, it is possible to appropriately adjust the depth of the well 12 using the thickness of the member 15.

For example, it is possible to deepen the well 12 by laminating a plurality of members 15.

Figure 61:
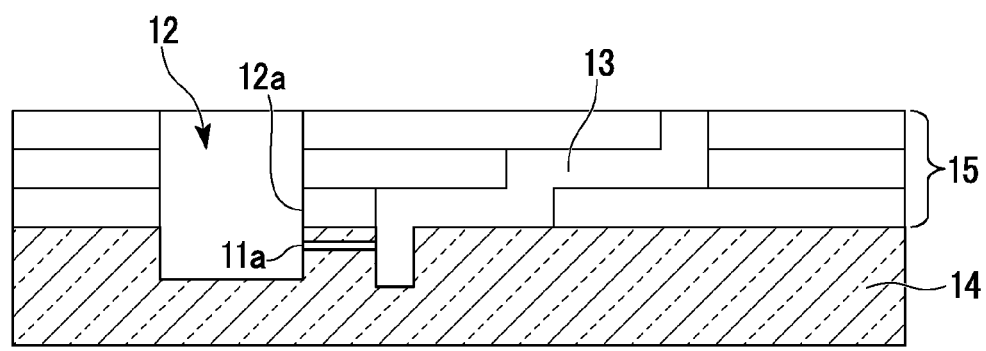
FIG. 61 is a cross-sectional view showing an example of the base body for forming a lipid membrane according to the invention.

Furthermore, as shown in FIG. 61, it is also possible to dispose the downstream of the first fluidic channel 13 on the top surface of the base body 20 using the height (thickness) of the laminated members 15.

The material of the member 15 is not particularly limited, and it is possible to use a resin substrate such as PDMS or PMMA, or a glass substrate.

The member that configures the side surface 12a of the well 12 and the top surface 13c of the first fluidic channel 13 may be constituted by a material that does not transmit light (for example, visible light) used for observation.

In a case in which the formation of the lipid membrane M is the only object, it is not necessarily required for the material of the member 15 to transmit light that is used for observation.

When a member that transmits light used for observation is used, optical observation from the top surface becomes possible, which is preferable.

Figure 62:
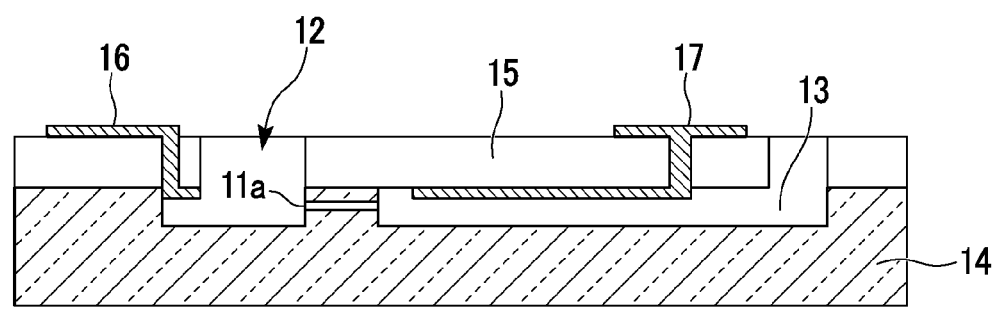
FIG. 62 is a cross-sectional view showing an example of the base body for forming a lipid membrane according to the invention.

In a case in which an electrophysiological measurement on the formed lipid membrane M is conducted, for example, it is possible to dispose electrodes 16 and 17 respectively in the well 12 and the first fluidic channel 13 as shown in FIG. 62.

Alternatively, it is possible to carry out an electrophysiological measurement using external electrodes through a buffer solution or the like.

Since the opening portion U is formed of the single glass substrate 14, it is possible to form high resistance sealing with respect to the lipid membrane M.

Therefore, the well-known patch-clamp method of the related art can be applied.

At this time, it is possible to carry out a more highly accurate electrophysiological measurement than in the related art by making the diameters of the openings of the holes including the first end portions 11a of the fine vacuum holes 11 that configure the opening portions U be smaller than the diameter of the opening (approximately 2 μm to 4 μm) of the hole of a patch pipet or the like of the related art.

the electrodes 16 and 17 may be disposed in a separate fluidic channel that is communicated to the well 12 and the first fluidic channel 13, for example, at least one of a fourth fluidic channel and a fifth fluidic channel described below.

Third Embodiment of a Base Body for Forming a Lipid Membrane

Figure 63:
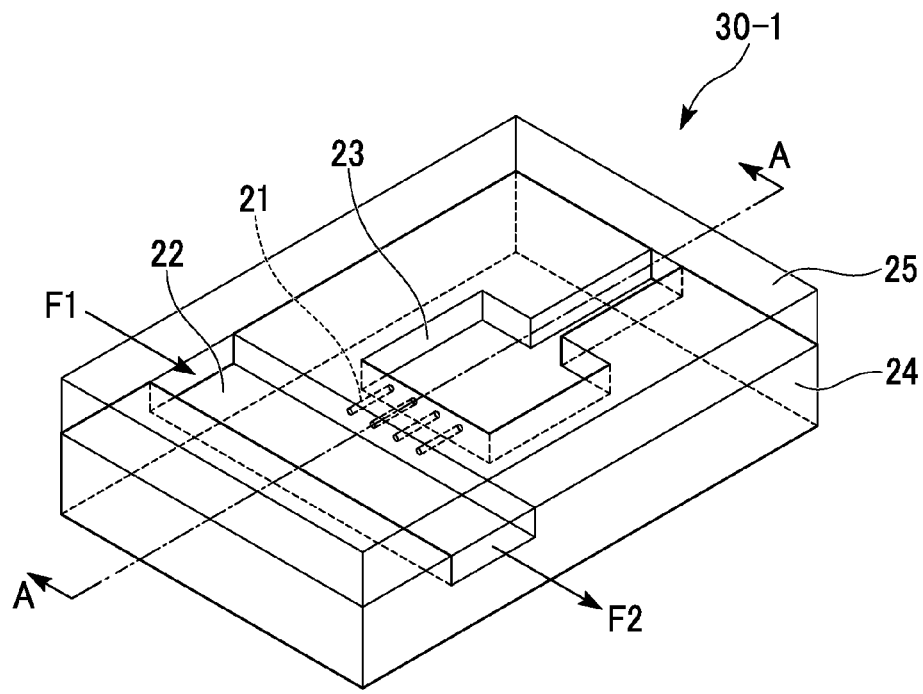
FIG. 63 is a schematic perspective view showing an example of a base body for forming a lipid membrane according to the invention.

FIG. 63 is a perspective view of a base body 30-1 which is a third embodiment of a base body for forming a lipid membrane according to the invention.

Figure 64:
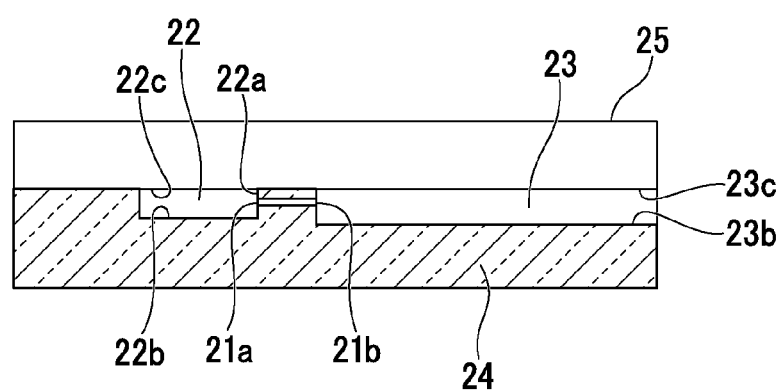
FIG. 64 is a cross-sectional view taken along the line A-A in FIG. 59.

FIG. 64 is a schematic view showing a cross-section taken along the line A-A in FIG. 63.

The base body 30-1 is a base body for forming a lipid membrane which has the micropores 21 that form the lipid membrane M.

The base body 30-1 includes at least the second fluidic channel 22 that configures a space present in the base member 24 which allows the liquid P including the lipids to flow in, the third fluidic channel 23 in which a negative pressure can be formed, and the micropores 21 that communicate the second fluidic channel 22 and the third fluidic channel 23.

The micropores 21 communicate to the outside of the base member 24 through the third fluidic channel 23.

The opening portions U through which the first end portions 21a of the micropores 21 are exposed are formed at the side surface 22a of the second fluidic channel 22, and at least some of the top surface 22c or bottom surface 22b of the second fluidic channel 22 is constituted by the transparent member 25 so that the lipid membrane M formed at the opening portions U can be optically observed.

At least portions that configure the micropores 21 in the base member 24 are formed of a single member.

In the base body 30-1 shown in FIG. 63, the single member configures not only the micropores 21 but also the entire base member 24.

Examples of the material of the single member include silicon, glass, silica, sapphire, and the like.

The above materials are excellent in terms of the workability when forming the micropores 21, which is preferable.

Among the above, the material is preferably an amorphous material that is not easily influenced by the working anisotropy determined by crystal orientations.

Furthermore, in a case in which glass, silica, or sapphire is employed as the material of the single member, and the lipid membrane M is optically observed using a microscope or the like, the above material is more suitable for the observation since the material transmits visible light (wavelength 0.36 μm to 0.83 μm).

In addition, the material of the member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light.

In a case in which the material of the single member transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the formed lipid membrane M visually through the single member.

Meanwhile, in the invention, the "transmission (being transparent)" refers to everything about a state in which transmitted light is obtained from the member by entering light into the member.

In FIG. 63, the single member that configures the base member 24 is a transparent glass substrate.

As shown in FIG. 64, the micropores 21 communicate the second fluidic channel 22 and the third fluidic channel 23.

The first end portions 21a of the micropores 21 are exposed (opened) at the side surface 22a of the second fluidic channel 22, and form the opening portions U.

The second end portions 21b of the micropores 21 are exposed at a side surface of the third fluidic channel 23.

The micropores 21 are formed in the single glass substrate 24, and are through holes having no seam or adhered surface.

Naturally, there is no seam or adhered surface in the opening portions U at the end portion of the micropores.

Here, the "opening portion U" refers to an area at which the first end portion 21a of the micropore 21 is opened, and the lipid membrane M is formed in the side surface 22a of the second fluidic channel 22.

The shape of the hole of the first end portion 21a of the micropore 21 which configures the opening portion U at the side surface 22a of the second fluidic channel 22 may be any shape of rectangular, triangular, oval and circular.

When the diameter or major axis of the hole is in a range of 0.02 µm to 5 µm, it is possible to easily form the lipid membrane M.

In addition, in the formed lipid membrane M, the diameter is preferably in a range of 0.02 µm to 5 µm even in a case in which an electric physiological measurement is conducted using the patch-clamp method.

It is possible to carry out a more accurate electrophysiological measurement by forming the lipid membrane M having a smaller area.

Therefore, the diameter or major axis is more preferably in a range of 0.02 µm to 3 µm.

When the diameter or major axis is less than the lower limit value of the above range, there is a concern that the area of the opening portion U may be too small such that the lipid membrane M is not appropriately formed.

When the diameter or major axis exceeds the upper limit value of the range, there is a concern that the sealing properties between the micropores 21 and the lipid membrane M may decrease such that it is not possible to form lipid membrane that is stabilized for a long period of time.

In FIG. 63, the micropore 21 is formed so as to be substantially perpendicular to the side surface 22a of the second fluidic channel 22.

However, the micropores do not necessarily need to be substantially perpendicular to the side surface, and can be freely disposed in the single glass substrate 24 in accordance with the design of the base body 30-1.

A plurality of micropores 21 may be disposed in the base body 30-1.

Since each of the micropores 21 has the opening portion U, it is possible to form a plurality of lipid membranes M.

The bottom surface 22b of the second fluidic channel 22 is constituted by the glass substrate 24.

The top surface 22c of the second fluidic channel 22 which is opposite to the bottom surface 22b is constituted by the member 25 such as plastic or glass.

It is possible to observe the lipid membrane M formed at the opening portions U from the top surface 22c or bottom surface 22b using the optical observation portion such as a microscope or the like.

The bottom surface 23b of the third fluidic channel 23 is constituted by the glass substrate 24, and the top surface 23c of the third fluidic channel 23 is constituted by the member 25.

Thereby, the third fluidic channel 23 forms a space in a half-sealed state.

The second end portions 21b of the micropores 21 are exposed and opened on the upstream of the third fluidic channel 23.

A negative pressure portion such as a syringe or a pump which can form a negative pressure in the third fluidic channel 23 is provided on the downstream of the third fluidic channel 23 (not shown).

Therefore, some of the liquid P which has flowed in from the upstream F1 of the second fluidic channel 22 to the downstream F2 of the second fluidic channel 22 is pulled into the third fluidic channel 23 through the micropores 21 by forming a negative pressure in the third fluidic channel 23.

Therefore, it is possible to form the lipid membrane M at the opening portions U in the first end portions 21a of the micropores 21 using, for example, the above method of forming the lipid membrane M.

Figure 65:
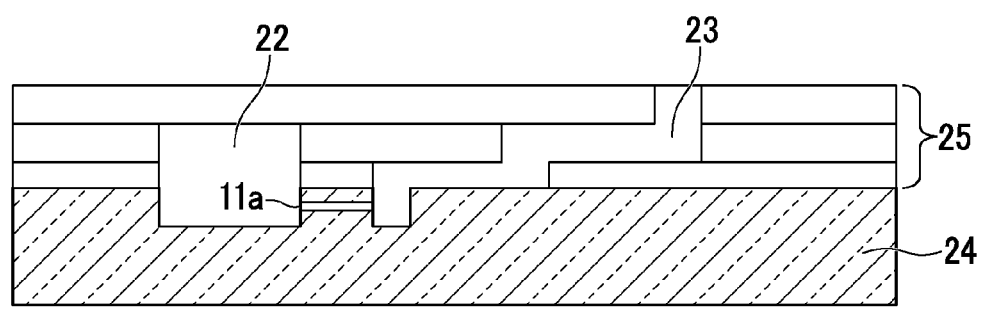
FIG. 65 is a cross-sectional view showing an example of the base body for forming a lipid membrane according to the invention.

In addition, as shown in FIG. 65, some of the side surface 22a of the second fluidic channel 22 may be constituted by the member 25.

Thereby, it is possible to appropriately adjust the flow rate of the liquid P in the second fluidic channel 22 using the thickness of the member 25.

For example, it is possible to increase the diameter of the second fluidic channel 22 by laminating a plurality of members 25.

Furthermore, it is also possible to dispose the downstream of the third fluidic channel 23 on the top surface of the base body 30 using the height (thickness) of the laminated members 25.

The material of the member 25 is not particularly limited, and it is possible to use a resin substrate such as PDMS or PMMA, or a glass substrate.

Meanwhile, the member that configures the top surface 23c of the third fluidic channel 23 may be constituted by a material that does not transmit light (for example, visible light) used for observation.

In a case in which the formation of the lipid membrane M is the only object, it is not necessarily required for the material of the member 25 to transmit light that is used for observation.

When a member that transmits light used for observation is used, optical observation from the top surface becomes possible, which is preferable.

Figure 66:
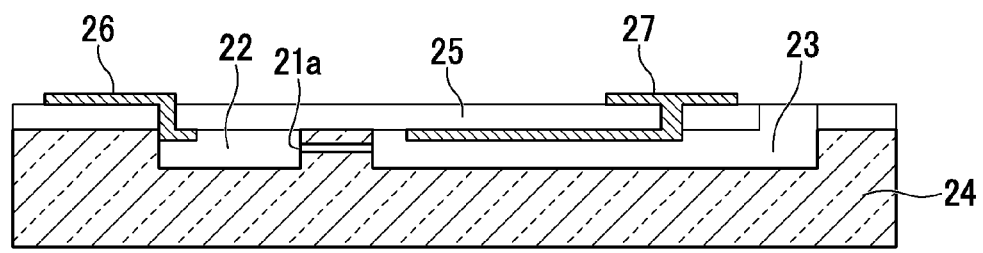
FIG. 66 is a cross-sectional view showing an example of the base body for forming a lipid membrane according to the invention.

In a case in which an electrophysiological measurement of the formed lipid membrane M is conducted, for example, it is possible to dispose the electrodes 26 and 27 respectively in the second fluidic channel 22 and the third fluidic channel 23 as shown in FIG. 66.

Alternatively, it is possible to carry out an electrophysiological measurement using external electrodes through a buffer solution or the like.

Since the opening portion U is formed of the single glass substrate 24, it is possible to form high resistance sealing with respect to the lipid membrane M.

Therefore, the well-known patch-clamp method of the related art can be applied.

At this time, it is possible to carry out a more highly accurate electrophysiological measurement than in the related art by making the diameters of the openings of the holes including the first end portions 21a of the fine vacuum holes 21 that configure the opening portions U be smaller than the diameter of the opening (approximately 2 μm to 4 μm) of the hole of a patch pipet or the like of the related art.

The electrodes 26 and 27 may be disposed in a separate fluidic channel that is communicated to the second fluidic channel 22 and the third fluidic channel 23, for example, at least one of the fourth fluidic channel and the fifth fluidic channel described below.

In the base body 30-1 of the third embodiment, the second fluidic channel 22 is employed instead of the well 12 in the base body 20-1 of the second embodiment.

Since it is possible to continuously circulate the liquid P in the second fluidic channel 22, compared to a case in which the well 22 is employed, it becomes possible to allow the available liquid P to continuously flow without stopping.

In addition, there is an advantage that liquids can be easily exchanged in the fluidic channel 22.

As described in the above method of forming the lipid membrane M, the operation in which a plurality of liquids such as the buffer solution and the liquid P including the lipid are sequentially brought into contact with the opening portions U becomes easier.

Fourth Embodiment of a Base Body for Forming a Lipid Membrane

Figure 67:
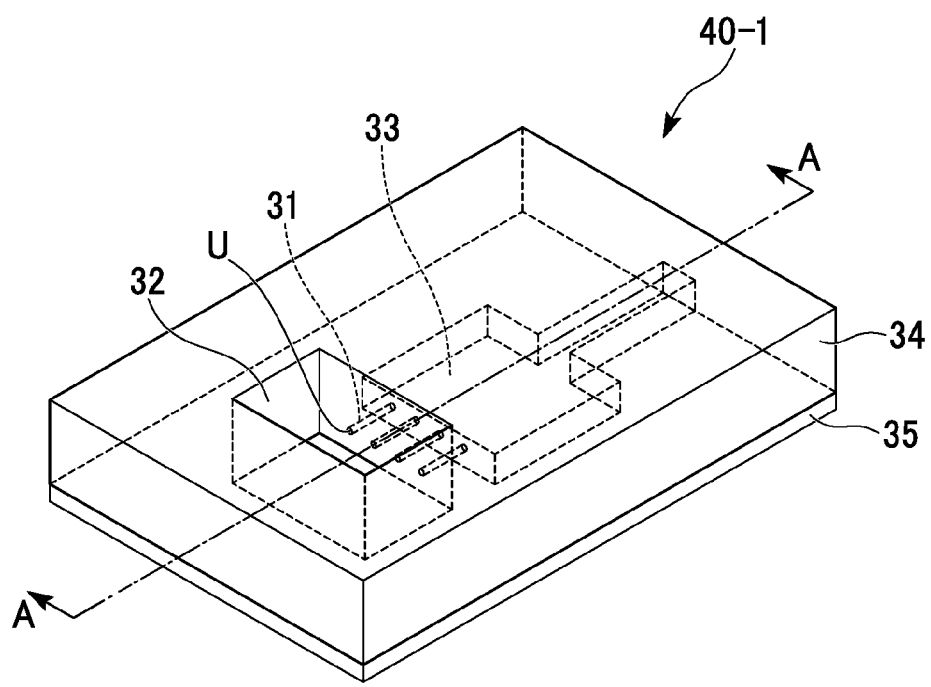
FIG. 67 is a schematic perspective view showing an example of a base body for forming a lipid membrane according to the invention.

FIG. 67 is a perspective view of a base body 40-1 which is a fourth embodiment of a base body for forming a lipid membrane according to the invention.

Figure 68:
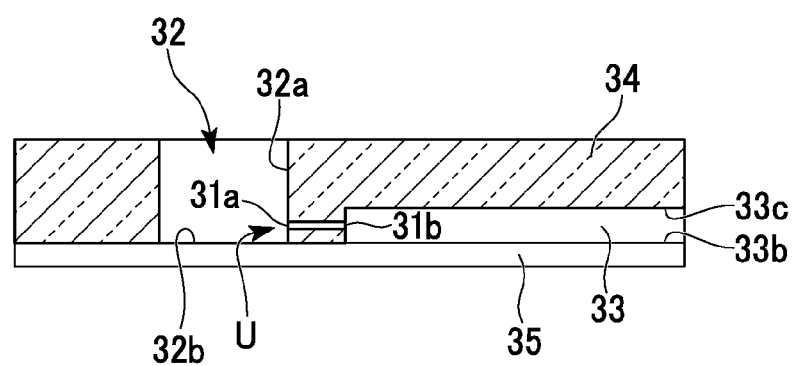
FIG. 68 is a cross-sectional view taken along the line A-A in FIG. 59.

FIG. 68 is a schematic view showing a cross-section taken along the line A-A in FIG. 67.

The base body 40-1 is a base body for forming a lipid membrane which has the micropores 31 that form the lipid membrane M.

The base body 40-1 includes at least the well 32 that configures a space present in the base member 34 which allows the liquid P including the lipids to flow in, the first fluidic channel 33 in which a negative pressure can be formed, and the micropores 31 that communicate the well 32 and the first fluidic channel 33.

The micropores 31 communicate to the outside of the base member 34 through the first fluidic channel 33.

The opening portions U through which the first end portions 31a of the micropores 31 are exposed are formed at the side surface 32a of the well 32, and at least some of the top surface or bottom surface 32b of the well 32 is opened or constituted by the transparent member 35 so that the lipid membrane M formed at the opening portions U can be optically observed.

At least portions that configure the micropores 31 in the base member 34 are formed of a single member.

In the base body 40-1 shown in FIG. 67, the single member configures not only the micropores 31 but also the entire base member 34.

Examples of the material of the single member include silicon, glass, silica, sapphire, and the like.

The above materials are excellent in terms of the workability when forming the micropores 31, which is preferable.

Among the above, the material is preferably an amorphous material that is not easily influenced by the working anisotropy determined by crystal orientations.

Furthermore, in a case in which glass, silica, or sapphire is employed as the material of the single member, and the lipid membrane M are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the material of the single member transmits the above laser light, it is possible to form the modified region by irradiating, with the laser, the member as described below.

In addition, the single member more preferably transmits light in the visible light range (approximately 0.36 μm to approximately 0.83 μm).

In a case in which the material of the single member transmits light in the visible light range, it is possible to easily observe the formed lipid membrane M visually through the single member.

Meanwhile, in the invention, the "transmission (being transparent)" refers to everything about a state in which transmitted light is obtained from the member by entering light into the member.

In FIG. 67, the single member that configures the base member 34 is a transparent glass substrate.

As shown in FIG. 68, the micropores 31 communicate the well 32 and the first fluidic channel 33.

The first end portions 31a of the micropores 31 are exposed (opened) at the side surface 32a of the well 32, and form the opening portions U.

The second end portions 31b of the micropores 31 are exposed at a side surface of the first fluidic channel 33.

The micropores 31 are formed in the single glass substrate 34, and are through holes having no seam or adhered surface.

Naturally, there is no seam or adhered surface in the opening portions U at the end portion of the micropores.

Here, the "opening portion U" refers to an area at which the first end portion 31a of the micropore 31 is opened, and the lipid membrane M is formed in the side surface 32a of the well 32.

The shape of the hole of the first end portion 31a of the micropore 31 which configures the opening portion U at the side surface 32a of the well 32 may be any of a rectangle, a triangle, an oval, and a circle.

When the diameter or major axis of the hole is in a range of 0.02 μm to 5 μm, it is possible to easily form the lipid membrane M.

In addition, in the formed lipid membrane M, the diameter is preferably in a range of 0.02 μm to 5 μm even in a case in which an electric physiological measurement is conducted using the patch-clamp method.

It is possible to carry out a more accurate electrophysiological measurement by forming the lipid membrane M having a smaller area.

Therefore, the diameter or major axis is more preferably in a range of 0.02 μm to 3 μm.

When the diameter or major axis is less than the lower limit value of the above range, there is a concern that the area of the opening portion U may be too small such that the lipid membrane M is not appropriately formed.

When the diameter or major axis exceeds the upper limit value of the range, there is a concern that the sealing properties between the micropores 31 and the lipid membrane M may decrease such that it is not possible to form lipid membrane that is stabilized for a long period of time.

In FIG. 68, the micropore 31 is formed so as to be substantially perpendicular to the side surface 32a of the well 32.

However, the micropores do not necessarily need to be substantially perpendicular to the side surface, and can be freely disposed in the single glass substrate 34 in accordance with the design of the base body 40-1.

A plurality of micropores 31 may be disposed in the base body 40-1.

Figure 69:
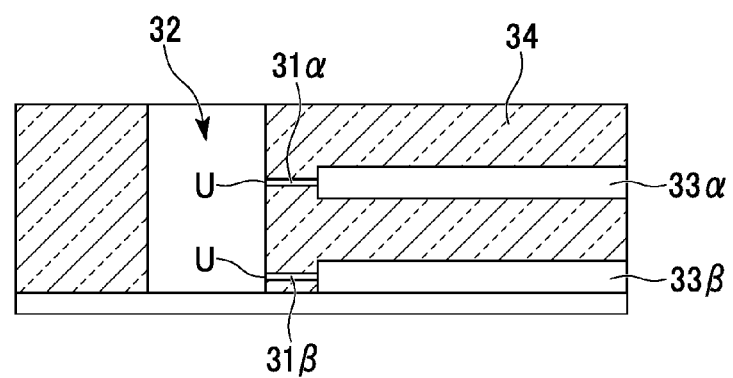
FIG. 69 is a cross-sectional view showing an example of the base body for forming a lipid membrane according to the invention.

For example, a plurality of micropores 31 may be disposed in parallel in the height (thickness) direction of the base body 40-1 as shown in FIG. 69.

In the above example, since each of the micropores 31 has the opening portion U and the first fluidic channel 33a and 33b, it is possible to independently control the operation of each of the opening portions U and to form a plurality of lipid membranes M at the respective opening portions U.

The bottom surface 32b of the well 32 is constituted by the member 35.

The top surface of the well 32 which is opposite to the bottom surface 32b is opened, and has no lid.

It is possible to observe the lipid membrane M formed at the opening portions U from the top surface or bottom surface 32b using the optical observation portion such as a microscope or the like.

Meanwhile, it is not a definite requirement that the top surface have no lid, and the top surface may be covered with a lid including a member such as a plastic, resin, or glass member (not shown).

The bottom surface 33b of the first fluidic channel 33 is constituted by the member 35 such as plastic or glass, and the top surface 33c of the first fluidic channel 33 is constituted by the glass substrate 34.

Thereby, the first fluidic channel 33 forms a space in a half-sealed state.

The second end portions 31b of the micropores 31 are exposed and opened on the upstream of the first fluidic channel 33.

A negative pressure portion such as a syringe or a pump which can form a negative pressure in the first fluidic channel 33 is provided on the downstream of the first fluidic channel 33 (not shown).

Therefore, the liquid P which has flowed in from the top surface of the well 32 is pulled into the first fluidic channel 33 through the micropores 31 by forming a negative pressure in the first fluidic channel 33.

Therefore, it is possible to form the lipid membrane M at the opening portions U in the first end portions 31a of the micropores 31 using, for example, the above method of forming the lipid membrane M.

Figure 70:
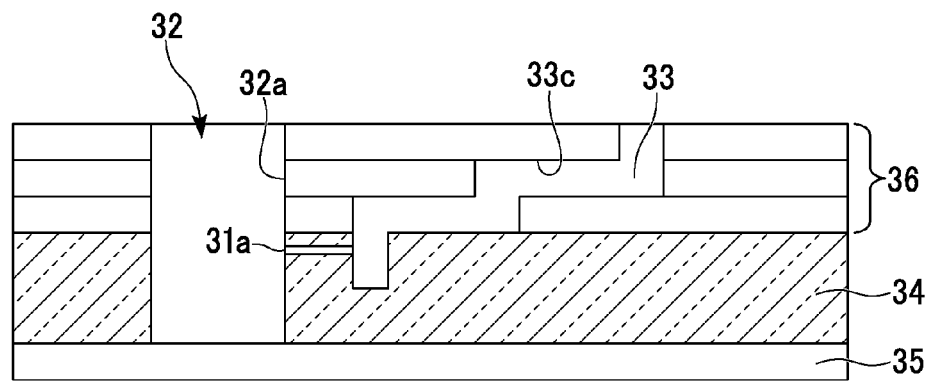
FIG. 70 is a cross-sectional view showing an example of the base body for forming a lipid membrane according to the invention.

As shown in FIG. 70, some of the side surface 32a of the well 32 may be constituted by the member 36.

Thereby, it is possible to appropriately adjust the depth of the well 32 using the thickness of the member 36.

For example, it is possible to deepen the well 32 by laminating a plurality of members 36.

Furthermore, it is also possible to dispose the downstream of the first fluidic channel 33 on the top surface of the base body 40-1 using the height (thickness) of the laminated members 36.

The material of the members 35 and 36 is not particularly limited, and it is possible to use a resin substrate such as PDMS or PMMA, or a glass substrate.

Meanwhile, the member that configures the side surface 32a of the well 32 and the top surface 33c of the first fluidic channel 33 may be constituted by a material that does not transmit light (for example, visible light) used for observation.

In a case in which the formation of the lipid membrane M is the only object, it is not necessarily required for the material of the members 35 and 36 to transmit light that is used for observation.

When a member that transmits light used for observation is used as the material of the members 35 and 36, optical observation from the top surface becomes possible, which is preferable.

In a case in which an electrophysiological measurement of the formed lipid membrane M is conducted, it is possible to carry out the electrophysiological measurement in the same manner as described for the base body 20-1 of the second embodiment by disposing electrodes respectively in the well 32, the first fluidic channel 33, and the like.

Fifth Embodiment of a Base Body for Forming a Lipid Membrane

Figure 71:
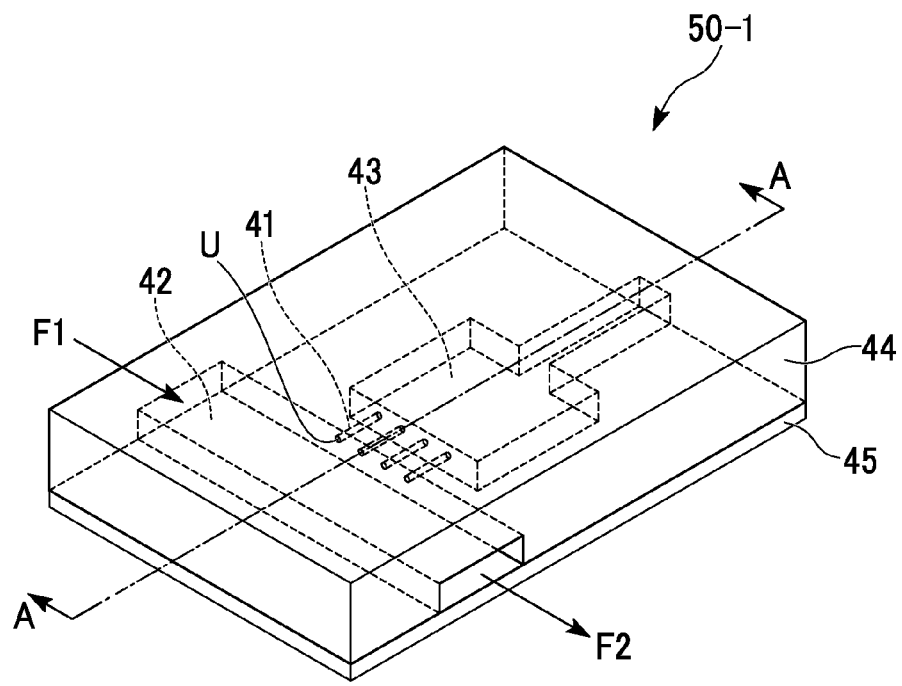
FIG. 71 is a schematic perspective view showing an example of a base body for forming a lipid membrane according to the invention.

FIG. 71 is a perspective view of a base body 50-1 which is a fifth embodiment of a base body for forming a lipid membrane according to the invention.

Figure 72:
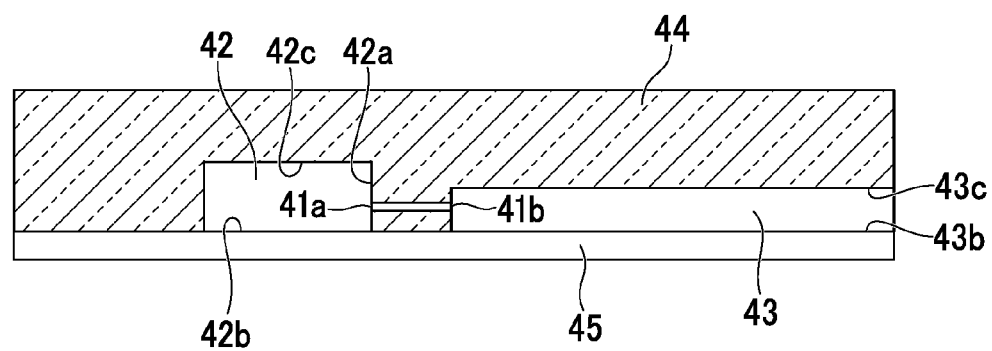
FIG. 72 is a cross-sectional view taken along the line A-A in FIG. 59.

FIG. 72 is a schematic view showing a cross-section taken along the line A-A in FIG. 71.

The base body 50-1 is a base body for forming a lipid membrane which has the micropores 41 that form the lipid membrane M.

The base body 50-1 includes at least the second fluidic channel 42 that configures a space present in the base member 44 which allows the liquid P including the lipids to flow in, the third fluidic channel 43 in which a negative pressure can be formed, and the micropores 41 that communicate the second fluidic channel 42 and the third fluidic channel 43.

The micropores 41 communicate to the outside of the base member 44 through the third fluidic channel 43.

The opening portions U through which the first end portions 41a of the micropores 41 are exposed are formed at the side surface 42a of the second fluidic channel 42, and at least some of the top surface 42c or bottom surface 42b of the second fluidic channel 42 is constituted by the transparent member 45 so that the lipid membrane M formed at the opening portions U can be optically observed.

At least portions that configure the micropores 41 in the base member 44 are formed of a single member.

In the base body 50 shown in FIG. 71, the single member configures not only the micropores 41 but also the entire base member 44.

Examples of the material of the single member include silicon, glass, silica, sapphire, and the like.

The above materials are excellent in terms of the workability when forming the micropores 41, which is preferable.

Among the above, the material is preferably an amorphous material that is not easily influenced by the working anisotropy determined by crystal orientations.

Furthermore, in a case in which glass, silica, or sapphire is employed as the material of the single member, and the lipid membrane M are optically observed using a microscope, the above material is more suitable for the observation since the material transmits visible light (wavelength 0.36 μm to 0.83 μm).

In addition, the material of the single member preferably transmits at least some wavelengths of light from light having a wavelength of 0.1 μm to 10 μm.

Specifically, the material of the single member preferably transmits light in at least a partial range of a general wavelength range (0.1 μm to 10 μm) which are used as a working laser light beam.

In a case in which the material of the single member transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the formed lipid membrane M visually through the single member.

Meanwhile, in the invention, the "transmission (being transparent)" refers to everything about a state in which transmitted light is obtained from the member by entering light into the member.

In FIG. 71, the single member that configures the base member 44 is a transparent glass substrate.

As shown in FIG. 72, the micropores 41 communicate the second fluidic channel 42 and the third fluidic channel 43.

The first end portions 41a of the micropores 41 are exposed (opened) at the side surface 42a of the second fluidic channel 42, and form the opening portions U.

The second end portions 41b of the micropores 41 are exposed at a side surface of the third fluidic channel 43.

The micropores 41 are formed in the single glass substrate 44, and are through holes having no seam or adhered surface.

Naturally, there is no seam or adhered surface in the opening portions U at the end portion of the micropores.

Here, the "opening portion U" refers to an area at which the first end portion 41a of the micropore 41 is opened, and the lipid membrane M is formed in the side surface 42a of the second fluidic channel 42.

The shape of the hole of the first end portion 41a of the micropore 41 which configures the opening portion U at the side surface 42a of the second fluidic channel 42 may be any shape of rectangular, triangular, oval and circular.

When the diameter or major axis of the hole is in a range of 0.02 μm to 5 μm, it is possible to easily form the lipid membrane M.

In addition, in the formed lipid membrane M, the diameter is preferably in a range of 0.02 μm to 5 μm in a case in which an electric physiological measurement is conducted using the patch-clamp method.

It is possible to carry out a more accurate measurement by forming the lipid membrane M having a smaller area.

Therefore, the diameter or major axis is more preferably in a range of 0.02 μm to 3 μm.

When the diameter or major axis is less than the lower limit value of the above range, there is a concern that the area of the opening portion U may be too small such that the lipid membrane M is not appropriately formed.

When the diameter or major axis exceeds the upper limit value of the range, there is a concern that the sealing properties between the micropores 41 and the lipid membrane M may decrease such that it is not possible to form lipid membrane that is stabilized for a long period of time.

In FIG. 72, the micropore 41 is formed so as to be substantially perpendicular to the side surface 42a of the second fluidic channel 42.

However, the micropores do not necessarily need to be substantially perpendicular to the side surface, and can be freely disposed in the single glass substrate 44 in accordance with the design of the base body 50-1.

A plurality of micropores 41 may be disposed in the base body 50-1.

Since each of the micropores 41 has the opening portion U, it is possible to form a plurality of lipid membranes M.

The bottom surface 42b of the second fluidic channel 42 is constituted by the member 45 such as plastic, a resin, or glass.

The top surface 42c of the second fluidic channel 42 which is opposite to the bottom surface 42b is constituted by the base member 44 formed of the glass substrate.

It is possible to observe the formed lipid membrane M from at least one of the top surface 42c and bottom surface 42b using the optical observation portion such as a microscope or the like.

The bottom surface 43b of the third fluidic channel 43 is constituted by the member 45, and the top surface 43c of the third fluidic channel 43 is constituted by the glass substrate 44.

Thereby, the third fluidic channel 43 forms a space in a half-sealed state.

The second end portions 41b of the micropores 41 are exposed and opened on the upstream side of the third fluidic channel 43.

A negative pressure portion such as a syringe or a pump which can form a negative pressure in the third fluidic channel 43 is provided on the downstream side of the third fluidic channel 43 (not shown).

Therefore, some of the liquid P which has flowed in from the upstream side F1 of the second fluidic channel 42 to the downstream side F2 of the second fluidic channel 42 is pulled into the third fluidic channel 43 side through the micropores 41 by forming a negative pressure in the third fluidic channel 43.

Therefore, it is possible to form the lipid membrane M at the opening portions U in the first end portions 41a of the micropores 41 using, for example, the above method of forming the lipid membrane M.

The material of the member 45 is not particularly limited, and it is possible to use a resin substrate such as PDMS or PMMA, or a glass substrate.

The member that configures the bottom surface 43b of the third fluidic channel 43 may be constituted by a material that does not transmit light (for example, visible light) used for observation.

In a case in which the formation of the lipid membrane M is the only object, it is not necessarily required for the material of the member 45 to transmit light that is used for observation.

When a member that transmits light used for observation is used, optical observation from the top surface becomes possible, which is preferable.

In a case in which an electrophysiological measurement of the formed lipid membrane M is conducted, it is possible to carry out the electrophysiological measurement in the same manner as described for the base body 20-1 of the second embodiment by disposing electrodes respectively in the second fluidic channel 42, the third fluidic channel 43, and the like.

Alternatively, it is possible to carry out an electrophysiological measurement using external electrodes through the buffer solution or the like.

Figure 73:
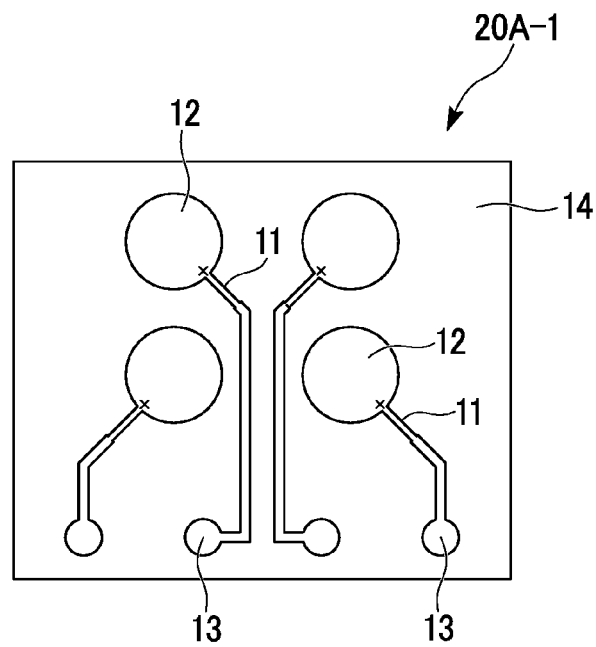
FIG. 73 is an outline top view showing an example of the base body for forming a lipid membrane according to the invention.

FIG. 73 is a schematic top view (transparent view seen from the top surface) of a base body 20A-1 which is an example of the base body for forming a lipid membrane according to the invention.

The disposition configuration of the wells 12, the micropores 11, and the first fluidic channels 13 on the top view can be applied to the base body 20-1 of the second embodiment, the base body 40-1 of the fourth embodiment, and the like.

Four sets of the well 12 and the first fluidic channel 13 are disposed respectively on the glass substrate 14.

The fact that the well 12 and the first fluidic channel 13 are communicated through the micropore 11 is as described above.

The location of the opening portion U is shown using an "X" mark.

It is also possible to dispose a plurality of first fluidic channels 13 in a well 12, and, at this time, at least one micropore 11 is provided to one first fluidic channel 13.

In a case in which a plurality of first fluidic channels 13 are disposed in one well 12 as described above, it becomes possible to independently control the suction at the first fluidic channel 13 by independently connecting the sucking portion (not shown) such as a syringe or a pump to each of the first fluidic channels 13.

Therefore, it is possible to independently control the formation of the lipid membrane M at the micropores 11.

Figure 74:
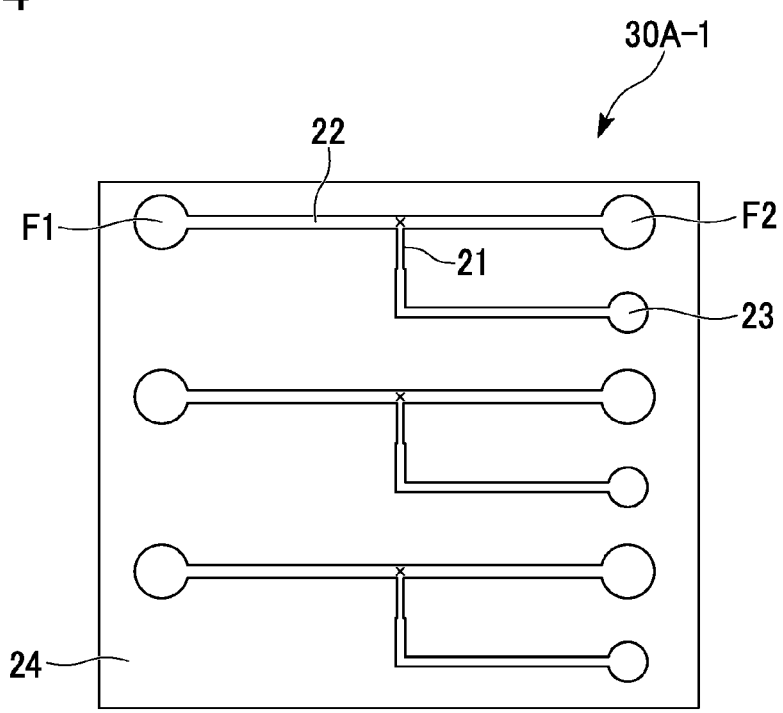
FIG. 74 is an outline top view showing an example of the base body for forming a lipid membrane according to the invention.

FIG. 74 is a schematic top view (transparent view seen from the top surface) of the base body 30A-1 which is an example of the base body for forming a lipid membrane according to the invention.

The disposition configuration of the second fluidic channels 22, the micropores 21, and the third fluidic channels 23 on the top view can be applied to the base body 30-1 of the third embodiment, the base body 50-1 of the fifth embodiment, and the like.

Three sets of the second fluidic channel 22 and the third fluidic channel 23 are disposed respectively on the glass substrate 24.

The fact that the second fluidic channel 22 and the third fluidic channel 23 are communicated through the micropore 21 is as described above.

The location of the opening portion U is shown using an "X" mark.

The liquid P is made to flow in from the upstream side F1 of the second fluidic channel 22 and circulates to the downstream F2 of the second fluidic channel 22.

It is also possible to dispose a plurality of third fluidic channels 23 in one second fluidic channel 22, and, at this time, at least one micropore 21 is provided to one third fluidic channel 23.

In a case in which a plurality of third fluidic channels 23 are disposed in one second fluidic channel 22 as described above, it becomes possible to independently control the suction at the third fluidic channel 23 by independently connecting a sucking portion (not shown) such as a syringe or a pump to each of the third fluidic channels 23.

Therefore, it is possible to independently control the formation of the lipid membrane M at the micropores 21.

Figure 75:
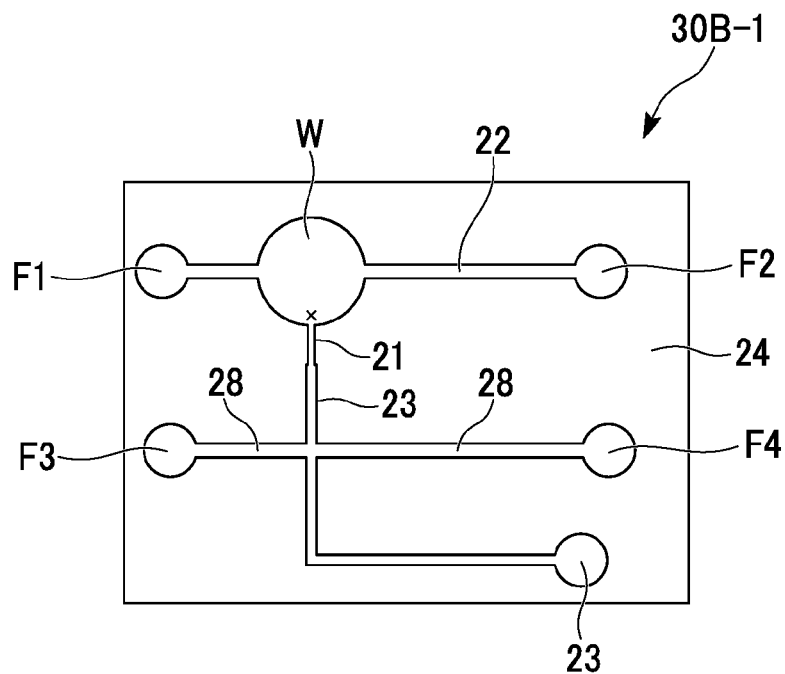
FIG. 75 is an outline top view showing an example of the base body for forming a lipid membrane according to the invention.

FIG. 75 is a schematic top view (transparent view seen from the top surface) of a base body 30B-1 which is an example of the base body for forming a lipid membrane according to the invention.

The disposition configuration of the second fluidic channels 22, the micropores 21, the third fluidic channels 23, and the fifth fluidic channels 28 on the top view can be applied to the base body 30-1 of the third embodiment, the base body 50-1 of the fifth embodiment, and the like.

The fact that the second fluidic channel 22 and the third fluidic channel 23 which are disposed in the glass substrate 24 are communicated through the micropore 21 is as described above.

The location of the opening portion U is shown using an "X" mark.

At an area W in which the opening portion U is provided, the fluidic channel width of the second fluidic channel 22 is expanded.

Therefore, when the liquid P is made to flow in from the upstream side F1 of the second fluidic channel 22 and circulates to the downstream F2 of the second fluidic channel 22, it is possible to make the liquid P remain in the area W.

The above remaining facilitates the formation of the lipid membrane M by attaching lipid molecules included in the liquid P to the opening portions U in the method of forming a lipid membrane M.

In addition, it is possible to make the area W function as a well by opening the lid of the area.

A fifth fluidic channel 28 is disposed in the glass substrate 24.

The fifth fluidic channel 28 intersects the third fluidic channel 23 so as to communicate with the third fluidic channel.

It is possible to make a desired chemical or gas diffuse and flow into the third fluidic channel 23 by circulating the chemical or gas from the upstream F3 to the downstream F4 of the fifth fluidic channel 28.

In addition, it is also possible to substitute a chemical diffused in the third fluidic channel 23 with gas.

The location at which the fifth fluidic channel 28 is communicated with the third fluidic channel 23 or the shape of the fifth fluidic channel 28 is not particularly limited.

Therefore, it is also possible to dispose the fifth fluidic channel 28 at, for example, a location near the micropore 21, and to make the fifth fluidic channel 28 and the third fluidic channel 23 replace their functions respectively.

In addition, the fifth fluidic channel 28 can have a configuration in which only the F3 side or the F4 side is provided, it is also possible to make the third fluidic channel 23 perform the function of any of the F3 and F4, and a plurality of fifth fluidic channels 28 or the fifth fluidic channel 28 branched into a plurality of parts may be disposed.

Figure 76:
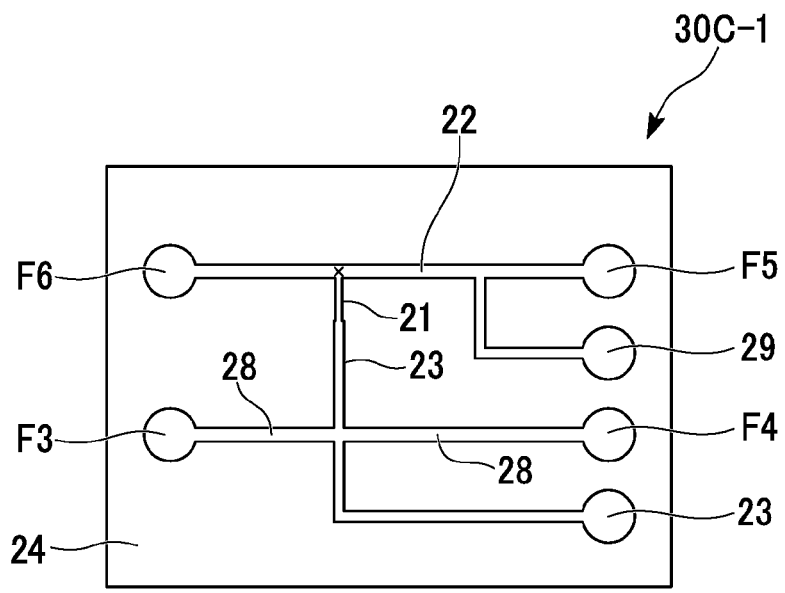
FIG. 76 is an outline top view showing an example of the base body for forming a lipid membrane according to the invention.

FIG. 76 is a schematic top view (transparent view seen from the top surface) of a base body 30C-1 which is an example of the base body for forming a lipid membrane according to the invention.

The disposition configuration of the second fluidic channels 22, the micropores 21, the third fluidic channels 23, the fifth fluidic channel 28, and the fourth fluidic channel 29 on the top view can be applied to the base body 30-1 of the third embodiment, the base body 50-1 of the fifth embodiment, and the like.

The fact that the second fluidic channel 22 and the third fluidic channel 23 which are disposed in the glass substrate 24 are communicated through the micropore 21 is as described above.

The location of the opening portion U is shown using an "X" mark.

The fifth fluidic channel 28 disposed in the glass substrate 24 intersects the third fluidic channel 23 so as to communicate with the third fluidic channel.

It is possible to make a desired chemical or gas diffuse and flow into the third fluidic channel 23 by circulating the chemical or gas from the upstream side F3 to the downstream side F4 of the fifth fluidic channel 28.

In addition, it is also possible to substitute a chemical diffused in the third fluidic channel 23 with gas.

The location at which the fifth fluidic channel 28 is communicated with the third fluidic channel 23 or the shape of the fifth fluidic channel 28 is not particularly limited.

Therefore, it is also possible to dispose the fifth fluidic channel 28 at, for example, a location near the micropore 21, and to make the fifth fluidic channel 28 and the third fluidic channel 23 replace their functions respectively.

In addition, the fifth fluidic channel 28 can have a configuration in which only the F3 side or the F4 side is provided, it is also possible to make the third fluidic channel 23 perform the function of any of the F3 and F4, and a plurality of fifth fluidic channels 28 or the fifth fluidic channel 28 branched into a plurality of parts may be disposed.

In addition, the fourth fluidic channel 29 disposed in the glass substrate 24 is communicated with the second fluidic channel 22.

It is possible to make a desired chemical or gas diffuse and flow into the second fluidic channel 22 by circulating the chemical or gas from the fourth fluidic channel 29 to the second fluidic channel 22.

That is, it is possible to bring the chemical or gas into contact with the lipid membrane M formed at the opening portions U.

In FIG. 76, the upstream of the second fluidic channel 22 is represented by F5, and the downstream is represented by F6.

The location at which the fourth fluidic channel 29 is communicated with the second fluidic channel 22 or the shape of the fourth fluidic channel 29 is not particularly limited.

Therefore, it is also possible to dispose the fourth fluidic channel 29 at a location near the micropore 21, and to make the fourth fluidic channel 29 and the upstream (F5 side) of the second fluidic channel 22 replace their functions respectively.

In addition, a plurality of fourth fluidic channels 29 or the fourth fluidic channel 29 branched into a plurality of parts may be communicated with the second fluidic channel 22, and may be disposed.

It is also possible to provide the fourth fluidic channel 29 so as to be communicated with a well instead of the second fluidic channel 22.

That is, in FIG. 76, it is also possible to form a configuration in which the second fluidic channel 22 is substituted with a well.

Next, the method of manufacturing the base body for forming a lipid membrane according to the invention will be described.

Method of Manufacturing a Base Body for Forming a Lipid Membrane (First Embodiment)

A first embodiment of the manufacturing method of the invention will be described using the above base body 20-1 as an example.

In this case, in the manufacturing method, a laser L having a pulse duration on the order of picoseconds or less is irradiated to areas that form micropores 55 in a single member 59 as shown in FIGS. 77A to 77D.

In addition, the manufacturing method includes at least the process A1 (FIG. 77A) in which modified regions 51 are formed in the areas, the process A2 (FIG. 77B) in which recess portions 53 and 54 or through holes that configure a well 57 and a first fluidic channel 58 that form the space (or a second fluidic channel 57 and a third fluidic channel 58 that form the space) are formed in the single member 59, and the process A3 (FIG. 77C) in which the modified regions 51 are removed from the single member 59 through etching.

[Process A1]

As the laser L (laser light L), laser light which has a pulse duration on the order of picoseconds or less is preferably used.

For example, it is possible to use a titanium sapphire laser, a fiber laser having the above pulse width, or the like.

However, it is necessary to use a wavelength at which the laser light transmits the member 59.

More specifically, laser light having a transmittance with respect to the member 59 of 60% or more is preferably used.

As the laser L (laser light L), it is possible to apply light in a general wavelength area (0.1 μm to 10 μm) which is used as a working laser.

Among the above, the laser needs to transmit the member 59 which is a member to be worked.

It is possible to form the modified regions 51 with respect to the member 59 by applying laser light having a wavelength at which the laser light transmits the member 59.

Examples of the material of the member 59 include silicon, glass, silica, sapphire, and the like.

The above materials are excellent in terms of the workability when forming the micropores 55, which is preferable.

Among the above, the material is preferably an amorphous material that is not easily influenced by the working anisotropy determined by crystal orientations.

Furthermore, in a case in which glass, silica, or sapphire is employed as the material of the member 59, and the lipid membrane M is optically observed using a microscope or the like, the above material is more suitable for the observation since the material transmits visible light (wavelength 0.36 μm to 0.83 μm).

In addition, the material of the member 59 preferably transmits at least some wavelengths of light from light having a wavelength of 0.1 μm to 10 μm.

Specifically, the material of the member 59 preferably transmits light in at least a partial range of a general wavelength range (0.1 μm to 10 μm) which are used as a working laser light beam.

In a case in which the material of the member 59 transmits the above laser light, it is possible to form the modified region by irradiating, with the laser, the member as described below.

In addition, the single member more preferably transmits light in the visible light range (approximately 0.36 μm to approximately 0.83 μm).

In a case in which the single member transmits light in the visible light range, it is possible to easily observe the formed lipid membrane M visually through the single member.

Meanwhile, in the invention, the "transmission (being transparent)" refers to everything about a state in which transmitted light is obtained from the member by entering light into the member.

In FIGS. 77A to 77D, the single member 59 is a transparent glass substrate (hereinafter referred to as the glass substrate 59).

Hereinafter, a case in which the member 59 is a glass substrate will be described, but it is possible to manufacture the base body in the same manner even in a case in which the material of the member 59 is other member, for example, silicon, silica, or sapphire.

In the process A2 described below, silicon, silica, or glass which has favorable workability is more preferable.

As the glass substrate 59, it is possible to use, for example, a glass substrate including silica, a glass substrate including glass mainly including silicate or borosilicate glass, or the like.

A glass substrate including synthetic silica is preferable due to the favorable workability.

In addition, the thickness of the glass substrate 59 is not particularly limited.

Figure 77A:
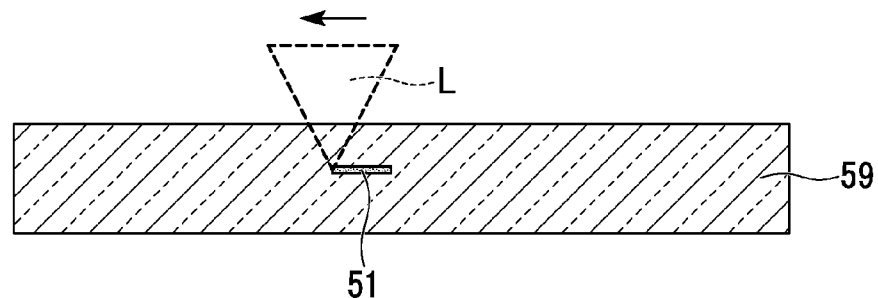
FIG. 77A is an outline cross-sectional view showing an example of a method of manufacturing the base body for forming a lipid membrane according to the invention.

As the method of irradiating with the laser light L, a method shown in FIG. 77A can be used.

That is, the modified regions 51 modified from glass are formed by irradiating with the laser light L so as to be condensed and focused in the glass substrate 59, and scanning the focus in the arrow direction.

It is possible to form the modified region 51 with a desired shape by scanning the focus over areas that form the micropores 55 in the glass substrate 59.

Here, the "modified region" refers to a portion which has a decreasing etching resistance, and is selectively or preferentially removed through etching.

When the laser light L is irradiated, it is preferable that the irradiation intensity is a value near the working threshold value or is lower than the working threshold value of the glass substrate 59, and the polarization direction (electric field direction) of the laser light L is so as to become perpendicular to the scanning direction.

This laser irradiating method will be hereinafter referred to as the laser irradiating method S.

The laser irradiating method S will be described in FIG. 78.

The propagation direction of the laser light L is indicated with the arrow Z, and the polarization direction (electric field direction) of the laser light L is indicated by the arrow Y.

In the laser irradiating method S, the irradiation area of the laser light L is so as to be in a planar surface 50a including the propagation direction of the laser light and the direction perpendicular to the polarization direction of the laser light.

Together with the above, the laser irradiation intensity is a value near the working threshold value or is lower than the working threshold value of the glass substrate 59.

It is possible to form the modified regions 51 having a diameter of the opening on the order of nanometers in the glass substrate 59 using the laser irradiating method S.

For example, the modified region 51 having a substantially oval cross-section with a minor axis of approximately 20 nm and a major axis of approximately 0.2 μm to 5 μm is obtained.

The substantially oval shape has the long axis in a direction along the propagation direction of the laser and the short axis in a direction along the electric field direction of the laser.

Depending on the conditions of the laser irradiation, there are cases in which the cross-section forms a shape similar to rectangular.

In a case in which the laser irradiation intensity is greater than or equal to the working threshold value of the glass substrate 59, there is a possibility that the obtained modified regions 51 are formed in accordance with the periodic structure.

That is, when a pulse laser on lower than or equal to the order of picoseconds is irradiated in a collective manner at greater than or equal to a working threshold value, interruption between an electronic plasma wave and the incident light occurs at the light-condensing portion, and a periodic structure that is perpendicular to the polarization of the laser and has a periodicity in the polarization direction is formed in a self-assembled manner.

The formed periodic structure forms a layer with a low etching resistance.

For example, in the case of silica, low oxygen concentration layers and high oxygen concentration layer are periodically arrayed (FIGS. 79C and 79D), the etching resistance decreases at the low oxygen concentration portions, and periodic recess portions and protrusions are formed when etching is conducted.

The above periodic recess portions and protrusions are not necessary when forming the micropores 55 described below.

Figure 79A:
FIG. 79A is a view schematically showing the relationship between laser irradiation energy and a formed modified region (low oxygen concentration portion).
Figure 79B:
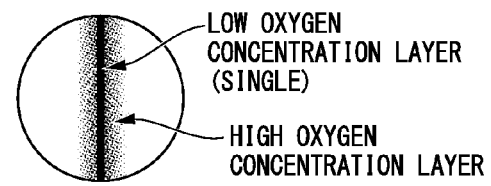
FIG. 79B is a view schematically showing the relationship between laser irradiation energy and the formed modified region (low oxygen concentration portion).
Figure 79C:
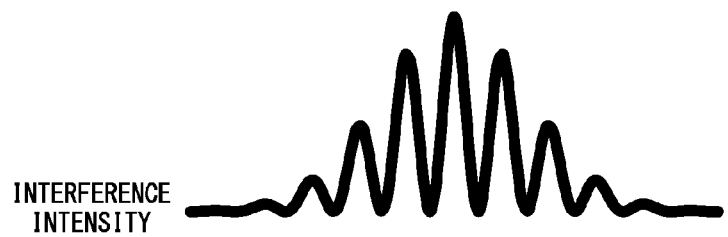
FIG. 79C is a view schematically showing the relationship between laser irradiation energy and the formed modified region (low oxygen concentration portion).
Figure 79D:
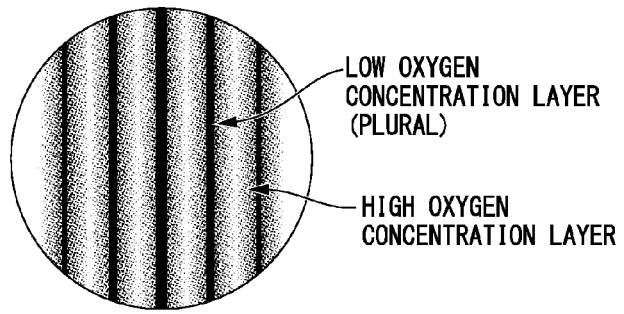
FIG. 79D is a view schematically showing the relationship between laser irradiation energy and the formed modified region (low oxygen concentration portion).

On the other hand, when the laser irradiation intensity is lower than the working threshold value of the glass substrate 59 and is greater than or equal to the lower limit value (processing lower limit threshold value) of the laser irradiation intensity at which the etching resistance can be decreased by modifying the glass substrate 59 as in the above laser irradiation method S, one low oxygen concentration portion (a layer having a low etching resistance) is formed through laser irradiation without forming the periodic structure (FIGS. 79A and 79B).

When the above etching is conducted, it is possible to form one micropore 55.

The above laser irradiating method S can make the shape of the micropore 55 be oval or substantially oval.

In addition, it becomes possible to control the minor axis at a size on the order of nanometers through etching.

When the minor axis of the oval or substantially oval shape is formed at a size of the order of nanometers, there are cases in which it becomes easy to more easily form the lipid membrane.

At this time, since it is possible to make the major axis larger than a size on the order of nanometers, it is possible to decrease the pressure loss of a fluid which flows into the micropores 55.

In addition, as a preliminary preparation for forming a lipid membrane, it is necessary to fill a liquid such as a buffer solution in the micropores 55 in advance.

In this case, since the capillary force increases as the holes become finer, there are cases in which an adverse effect of the fluid failing to flow outside the space or the like from the fine vacuum holes 55 is caused.

However, when the micropores 55 are made to be oval or substantially oval, the capillary force is suppressed even in a minor axis that is small enough to form the lipid membrane so that it is possible to suppress the adverse effect of the fluid failing to flow outside the space or the like.

Even when only one layer having a low etching resistance (the low oxygen concentration layer for silica or glass) is formed through laser irradiation (in the present specification, referred to as the modified region 51), the low oxygen concentration portions become layers which are extremely easily etched.

The above fact was found through thorough studies by the present inventors.

Therefore, the working threshold value is defined as the lower limit value (the upper limit value of the range of laser irradiation intensities at which the periodic structure is not formed) of laser irradiation intensities at which the periodic structure can be formed.

In addition, the "lower limit value of laser irradiation intensities at which the etching resistance can be decreased by modifying the glass substrate 59 (working lower limit threshold value)" refers to a limit value at which it is possible to open the micropores 55 in the glass substrate 59 through an etching treatment.

When the laser irradiation intensity is lower than the lower limit value, it is not possible to form a layer with a low etching resistance through laser irradiation, and therefore the micropores 55 are not opened.

That is, the "working upper limit threshold value" refers to the lower limit value of laser irradiation intensities at which interruption between an electronic plasma wave generated by the interaction between the base member and the laser light and the entering laser light occurs in the focus (light-condensing area) of light irradiated into the base member, and a banded modified region can be formed in a self-assembled manner in the base member due to the interruption.

In addition, the "working lower limit threshold value" refers to the lower limit value of laser irradiation intensities at which the modified region modified from the base member is formed in the focus (light-condensing area) of laser light irradiated into the base member, and the etching resistance of the modified region can be decreased so that the modified region can be selectively or preferentially etched through an etching treatment which is a post process.

An area to which a laser is irradiated with a laser irradiation intensity lower than the working lower limit threshold value is not easily etched selectively or preferentially in the etching treatment which is a post process.

Therefore, in order to form the modified region that forms a micro hole after etching, it is preferable to set a laser irradiation intensity of the lower limit threshold value to the upper limit threshold value.

The working upper limit threshold value and the working lower limit threshold value are roughly determined depending on the wavelength of the laser light, the material (material quality) of the base member which is a subject of laser irradiation, and the laser irradiation conditions.

However, when the relative orientation of the polarization direction and scanning direction of the laser light differs, there are cases in which the working upper limit threshold value and the working lower limit threshold value also somewhat differ.

For example, in a case in which the scanning direction is perpendicular to the polarization direction and a case in which the scanning direction is parallel to the polarization direction, there are cases in which the processing upper limit threshold value and the process lower limit threshold value differ.

Therefore, for the wavelength of the laser light to be used and the base member to be used, it is preferable to investigate in advance the working upper limit threshold values and the working lower limit threshold values of cases in which the relative relationship between the polarization direction and the scanning direction of the laser light is changed.

Although a linear polarization has been described in detail as the polararization, it can be easily assumed that the same structure (modified region) is formed even when a laser pulse having a somewhat oval palarization component is used.

The method of scanning the focus of the laser light L is not particularly limited, and the modified region 51 that can be formed through a single process of continuous scanning is limited in the planar surface 50a corresponding to the propagation direction (the arrow Z direction) of the laser light and the direction perpendicular to the polarization direction (the arrow Y direction) of the laser light.

It is possible to form the modified region in an arbitrary shape as long as the modified region is formed in the planar surface.

Figure 78:
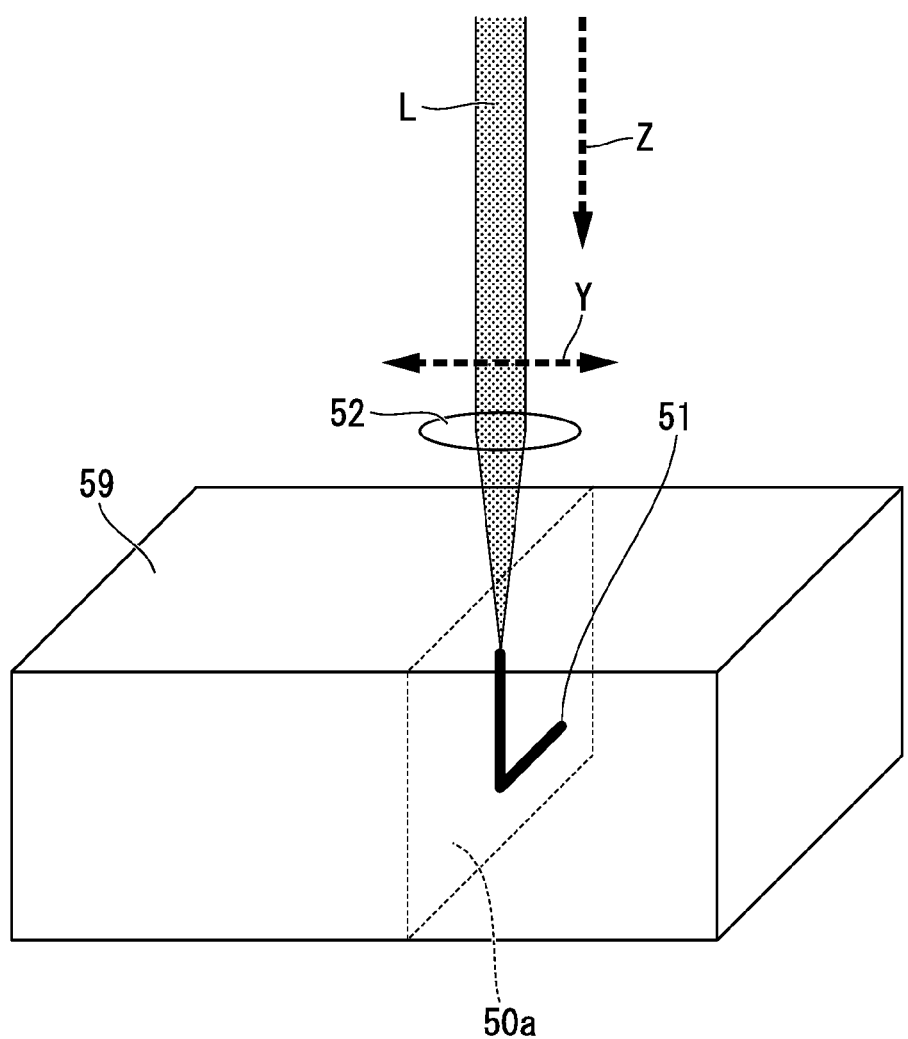
FIG. 78 is a schematic perspective view showing the laser irradiation method S.

Here, a case in which the propagation direction of the laser light L is perpendicular to the top surface of the glass substrate 59 has been shown in FIG. 78, but the propagation direction is not necessarily perpendicular.

The laser L may be irradiated at a desired incident angle with respect to the top surface.

Generally, the transmittance of the laser at the modified region differs from the transmittance of the laser at an unmodified region.

Therefore, it is generally difficult to control the focus location of the laser light that has transmitted at the modified region.

Therefore, the modified region is desirably formed at an area located inside when seen from a surface on the laser irradiation side.

In addition, it is also possible to form the modified region having an arbitrary shape in the three-dimensional direction in the glass substrate 59 by appropriately changing the polarization direction (the arrow Y direction) of the laser.

In addition, as shown in FIG. 78, the modified region 51 may be formed by condensing the laser light L using a lens 52 and irradiating with the laser light as described above.

As the lens, it is possible to use, for example, a refractive object lens or a reflective lens, and, alternatively, it is also possible to irradiate with the laser light, for example, in a Fresnel, reflective, oil immersion, or water immersion manner.

In addition, for example, when a cylindrical lens is used, it is possible to irradiate with the laser in a wide range on the glass substrate 59 at a single process.

In addition, for example, when a conical lens is used, it is possible to irradiate with the laser light L in a wide range in the perpendicular direction of the glass substrate 59 at a single process.

However, in a case in which a cylindrical lens is used, the polarization of the laser light L needs to be horizontal to a direction in which the lens has a curvature.

Specific examples of the laser irradiation conditions S include a variety of the following conditions.

For example, a titanium sapphire laser (a laser using a crystal obtained by doping titanium in sapphire as a laser medium) is used.

The laser light to irradiate has, for example, a wavelength of 800 nm and a repetition frequency of 200 kHz, and the laser light L is irradiated in a collective manner at a laser scanning rate of 1 mm/second.

The values of the above wavelength, repetition frequency, and scanning rate are an example, are not limited thereto for the invention, and can be arbitrarily changed.

As the lens 52 used for condensing light, for example, an object lens having N.A.<less than 0.7 is preferably used.

In order to form finer vacuum holes 55, when the glass substrate 59 is irradiated, the pulse intensity is preferably a value near the working upper limit threshold value, for example, a power of approximately 80 nJ/pulse or less.

When the power is the above value or more, since the periodic structure is formed, and is connected through etching, it becomes difficult to form the micropores 55 having a diameter of the opening on the order of nanometers.

In addition, even when N.A.≥0.7, working is possible; however, since the size of the spot becomes smaller, and the laser fluence becomes larger, there is a demand for irradiation of the laser at a smaller pulse intensity.

[Process A2]

Subsequently, the recess portions 53 and 54 or through holes which configure the well 57 and the first fluidic channel 58 which forms the space (or the second fluidic channel 57 and the third fluidic channel 58 which form the space) are formed in the single glass substrate 59.

Examples of the method of forming the recess portions 53 and 54 include the following method.

Firstly, a resist 52 is patterned on the top surface of the glass substrate 59 through, for example, photolithography or the like.

Figure 77B:
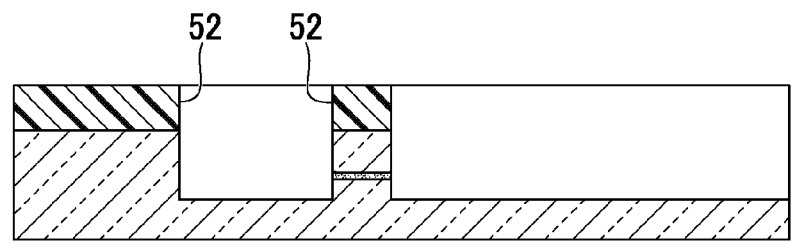
FIG. 77B is an outline cross-sectional view showing an example of the method of manufacturing the base body for forming a lipid membrane according to the invention.

Subsequently, areas in which the resist 52 is not patterned on the top surface of the glass substrate 59 are etched and removed to a desired depth using a method such as dry etching, wet etching, or sand blasting (FIG. 77B).

At the end, when the resist 52 which has become unnecessary is peeled off, the glass substrate 59 on which the first recess portion 53 and the second recess portion 54 are formed is obtained.

In the above example, a case in which the first recess portion 53 becomes the well 57, and the second recess portion 54 becomes the first fluidic channel 58 has been described.

In the process A2, the cross-section of the modified region 51 formed in the process A1 is preferably exposed at the side surfaces of the first recess portion 53 and the second recess portion 54 to be formed.

It becomes easier to form the micropores 55 through an etching treatment in the process A3 at the later phase.

In addition, in the process A2, through holes may be formed instead of forming the recess portions 53 and 54.

In this case, the first fluidic channel (the second fluidic channel and the third fluidic channel) may be formed by excavating areas that form the first fluidic channel and the second fluidic channel in the glass substrate 59 from the surface of the glass substrate 59 using a fine drill (laser drill) or the like so as to form through holes.

In addition, combinations of the excavating method using the drill and a variety of etching methods may be used.

[Process A3]

Figure 77C:
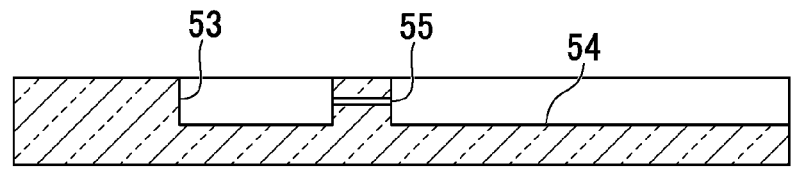
FIG. 77C is an outline cross-sectional view showing an example of the method of manufacturing the base body for forming a lipid membrane according to the invention.

Subsequently, the modified regions 51 formed in the process A1 are removed from a single glass substrate 59 through etching (FIG. 77C).

Wet etching is preferable as the etching method.

Since the modified regions 51 having the cross-section exposed at the side surfaces of the recess portions 53 and 54 (or the through holes) have a decreased etching resistance, selective or preferential etching is possible.

The above etching is a method in which a phenomenon in which the modified regions 51 are etched extremely faster than the unmodified regions in the glass substrate 59 is used, and, consequently, it is possible to form the micropores 55 in accordance with the shape of the modified regions 51.

The etching fluid is not particularly limited, and, for example, a solution mainly including hydrofluoric acid (HF), a hydrofluoric-nitric acid-based mixed acid obtained by adding an appropriate amount of nitric acid or the like to hydrofluoric acid, or the like can be used.

In addition, it is also possible to use other chemicals in accordance with the material of the member 59.

As a result of the etching, it is possible to form the micropores 55 having a diameter of the opening on the order of nanometers at predetermined locations in the glass substrate 59 so as to communicate the first recess portion 53 and the second recess portion 54.

As the size of the micropores 55, for example, it is possible to make through holes having a substantially oval cross-section having a minor axis of approximately 20 nm to 200 nm and a major axis of approximately 0.2 μm to 5 μm.

There are cases in which the cross-section becomes substantially rectangular depending on the conditions of the etching treatment.

It is possible to control the size of the micropores 55 by adjusting the treatment duration of the wet etching.

Theoretically, it is possible to make the minor axis several nm to several tens of nm by shortening the treatment duration.

In contrast to the above, it is also possible to make the minor axis approximately 1 μm to 2 μm and the major axis approximately 5 μm to 10 μm.

Figure 77D:
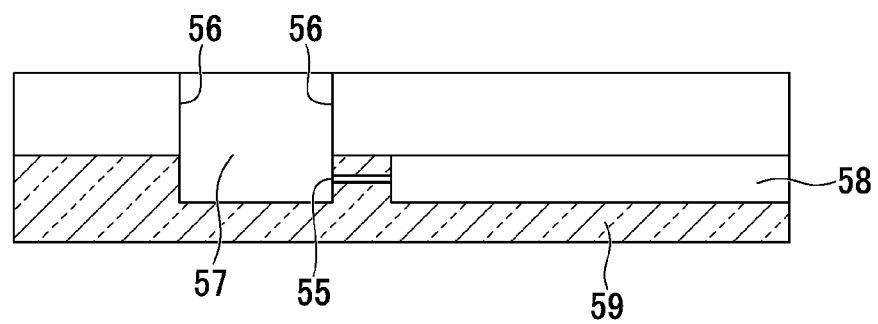
FIG. 77D is an outline cross-sectional view showing an example of the method of manufacturing the base body for forming a lipid membrane according to the invention.

Next, it is possible to form the first fluidic channel 58 by adhering a member 56 to the top surface of the glass substrate 59 so as to cover the formed second recess portion 54 (FIG. 77D).

The formed first recess portion 53 can be used as the well 57 as it is, and it is possible to appropriately adjust the depth of the well 57 by adhering the member 56 to the glass substrate 59 while the top surface of the well 57 is made to remain open as shown in FIG. 77D.

On the other hand, It is also possible to form the second fluidic channel 57 instead of the well 57 by adhering the member 56 to the top surface of the glass substrate 59 so as to cover the first recess portion 53 (not shown).

In this case, the first fluidic channel 68 can be differently referred to as the third fluidic channel 68.

As the method of adhering the member 56 and the top surface of the glass substrate 59, a well-known method may be conducted depending on the material of the member 56.

In addition, it is also possible to appropriate install electrodes, wires, and the like for an electrophysiological measurement in the first fluidic channel 58 during the adhering.

The material of the member 56 is not particularly limited, and it is possible to use a resin substrate such as PDMS or PMMA, or a glass substrate.

In addition, the material of the member 56 may be constituted by a material that does not transmit light (for example, visible light) used for observation.

In a case in which the formation of a lipid membrane is the only object, the material of the member 56 does not necessarily need to transmit light used for observation.

When a member that transmits light used for observation is used, optical observation from the top surface becomes possible, which is preferable.

The member that is used to form the first fluidic channel 58 and covers the second recess portion 54 does not necessarily need to be a member that transmits light that is used for observation, and may be a member that does not transmits light that is used for observation.

As the etching in the process A2 and the process A3, wet etching or dry etching can be applied.

In the wet etching, for example, use of 1% or less of hydrofluoric acid is most preferable, but a material having other acidic or basic properties may be used.

Among the dry etching methods, examples of an isotropic etching method include a variety of dry etching methods such as barrel-type plasma etching, parallel plate-type plasma etching, and down flow-type chemical dry etching.

Among anisotropic dry etching methods, as a method in which reactive ion etching (hereinafter RIE) is used, it is possible to use, for example, parallel plate-type RIE, magnetron-type RIE, ICP-type RIE, NLD-type RIE, and the like.

In addition to RIE, it is possible to use etching in which, for example, a neutral particle beam is used.

In addition, in a case in which an anisotropic dry etching method is used, it is also possible to carry out a process similar to isotropic etching by shortening the mean free path of ions using a method of increasing the process pressure or the like.

As a gas being used, it is possible to use a gas mixture obtained by mixing a main component of a gas that can chemically etch the material such as fluorocarbon-based gas, SF-based gas, $CHF_3$, fluorine gas, or chlorine gas, and other appropriate gases, for example, oxygen, argon, helium, or the like.

In addition, it is also possible to carry out the process using other dry etching methods.

Anisotropic etching is more preferable in the process A2, and isotropic etching is more preferable in the process A3.

Method of Manufacturing the Base Body for Forming a Lipid Membrane (Second Embodiment)

A second embodiment of the manufacturing method of the invention will be described using the base body 20-1 as an example.

In this case, as shown in FIGS. 80A to 80E, the manufacturing method includes at least a process B1 (FIG. 80B) in which recess portions 63 and 64 or through holes that configure a well 67 and a first fluidic channel 68 that form the space (or a second fluidic channel 67 and a third fluidic channel 68 that form the space) are formed in a single member 69, a process B2 (FIG. 80C) in which modified regions 61 are formed in areas which form fine vacuum holes 65 in the single member 69 by irradiating, with the laser L having a pulse duration on the order of picoseconds or less, the areas, and a process B3 (FIG. 80D) in which the modified regions 61 are removed from the single member 69 through etching.

Examples of the material of the member 69 include silicon, glass, silica, sapphire, and the like.

The above materials are excellent in terms of the workability when forming the fine vacuum holes 65, which is preferable.

Among the above, the material is preferably an amorphous material that is not easily influenced by the working anisotropy determined by crystal orientations.

Furthermore, in a case in which glass, silica, or sapphire is employed as the material of the member 69, and the formed lipid membrane are optically observed using a microscope or the like, the above material is more suitable for the observation since the material transmits visible light (wavelength 0.36 μm to 0.83 μm).

In addition, the material of the member 69 preferably transmits at least some wavelengths of light from light having a wavelength of 0.1 μm to 10 μm.

Specifically, the material of the member 69 preferably transmits light in at least a partial range of a general wavelength range (0.1 μm to 10 μm) which are used as a working laser light.

In a case in which the material of the member 69 transmits the above laser light, it is possible to form the modified region by irradiating with the laser, the member as described below.

In addition, the single member more preferably transmits light in the visible light range (approximately 0.36 μm to approximately 0.83 μm).

In a case in which the single member transmits light in the visible light range, it is possible to easily observe the formed lipid membrane visually through the single member.

Meanwhile, in the invention, the "transmission (being transparent)" refers to everything about a state in which transmitted light is obtained from the member by entering light into the member.

In FIGS. 80A to 80E, the single member 69 is a transparent glass substrate (hereinafter referred to as the glass substrate 69).

[Process B1]

The process B1 can be conducted in the same manner as for Process A2 in the first embodiment of the manufacturing method of the invention.

Figure 80A:
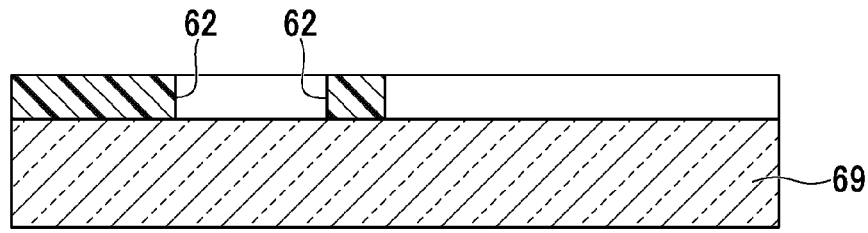
FIG. 80A is an outline cross-sectional view showing an example of the method of manufacturing the base body for forming a lipid membrane according to the invention.

That is, a resist 62 is patterned on the top surface of the glass substrate 69 through photolithography (FIG. 80A).

Figure 80B:
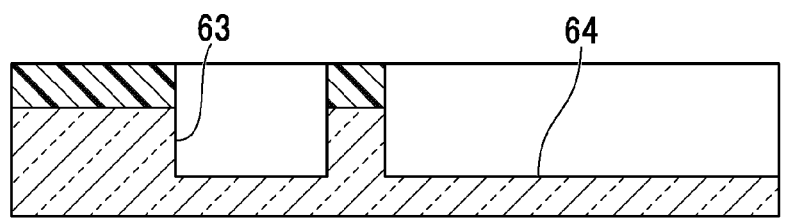
FIG. 80B is an outline cross-sectional view showing an example of the method of manufacturing the base body for forming a lipid membrane according to the invention.

Subsequently, areas in which the resist 62 is not patterned on the top surface of the glass substrate 69 are etched and removed to a desired depth using a method such as dry etching, wet etching, or sand blasting (FIG. 80B).

At the end, when the resist 62 which has become unnecessary is peeled off, the glass substrate 69 on which the first recess portion 63 and the second recess portion 64 are formed is obtained.

In the above example, a case in which the first recess portion 63 becomes the well 67, and the second recess portion 64 becomes the first fluidic channel 68 has been described.

In addition, in the process B1, fluidic channels may be formed in the substrate instead of forming the recess portions 63 and 64.

In this case, the first fluidic channel (the second fluidic channel and the third fluidic channel) may be formed by excavating areas that form the first fluidic channel and the second fluidic channel in the glass substrate 69 from the surface of the glass substrate 69 through drilling (laser drilling), combination of laser modification having a duration on the order of picoseconds or less, and selective etching, or the like so as to form through holes.

In addition, combinations of the excavating method using the drill and a variety of etching methods may be used.

[Process B2]

Next, the modified regions 61 are formed in areas that form the fine vacuum holes 65 in the single glass substrate 69 by irradiating, with the laser L having a pulse duration on the order of picoseconds or less, the areas.

Specifically, the modified regions can be formed in the same manner as in Process A1 in the first embodiment of the manufacturing method of the invention.

Figure 80C:
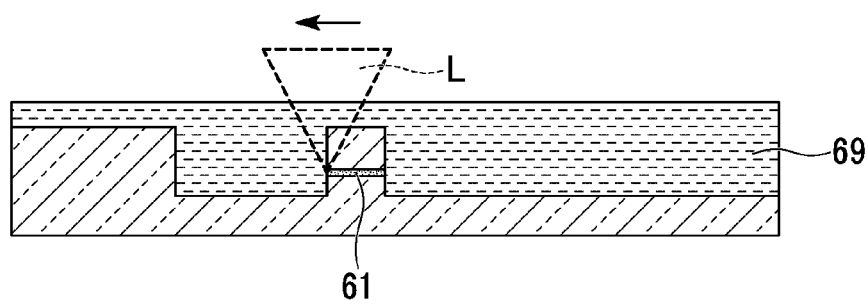
FIG. 80C is an outline cross-sectional view showing an example of the method of manufacturing the base body for forming a lipid membrane according to the invention.

At this time, in a case in which the modified regions 61 are formed at portions at which the modified regions are exposed to the side surface of the first recess portion 63 and the second recess portion 64 by irradiating with the laser L in a collective manner, the laser light L is more desirably irradiated through liquid immersion exposure (FIG. 80C).

It is possible to increase the accuracy of the shape of the modified regions 61 formed at the portions at which the modified regions are exposed to the side surfaces (the shape of the fine vacuum holes 65 at the end portions).

[Process B3]

Figure 80D:
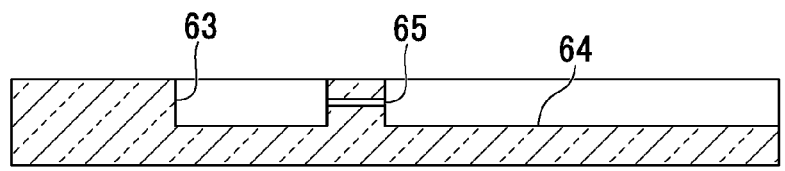
FIG. 80D is an outline cross-sectional view showing an example of the method of manufacturing the base body for forming a lipid membrane according to the invention.

Subsequently, the modified regions 61 formed in the process B2 are removed from the single glass substrate 69 through etching (FIG. 80D).

Wet etching is preferable as the etching method.

Since the modified regions 61 having the cross-section exposed at the side surfaces of the recess portions 63 and 64 (or the through holes) have a decreased etching resistance, selective or preferential etching is possible.

Specifically, the modified regions can be removed in the same manner as in Process A3 in the first embodiment of the manufacturing method of the invention.

As a result of the etching, it is possible to form the fine vacuum holes 65 having a diameter of the opening on the order of nanometers at predetermined locations in the glass substrate 69 so as to communicate the first recess portion 63 and the second recess portion 64.

Figure 80E:
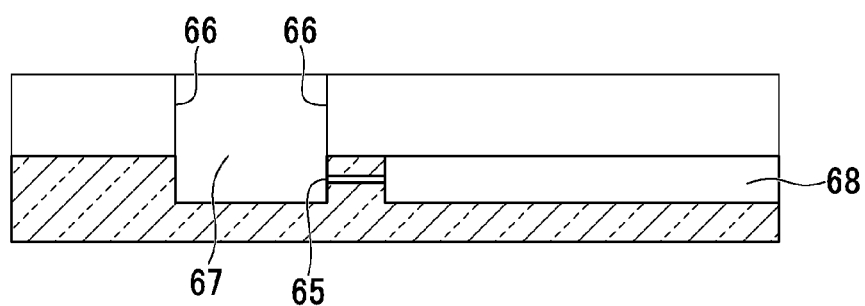
FIG. 80E is an outline cross-sectional view showing an example of the method of manufacturing the base body for forming a lipid membrane according to the invention.

Next, it is possible to form the first fluidic channel 68 by adhering a member 66 to the top surface of the glass substrate 69 so as to cover the formed second recess portion 64 (FIG. 80E).

The formed first recess portion 63 can be used as the well 67 as it is, and it is possible to appropriately adjust the depth of the well 67 by adhering the member 66 to the glass substrate 69 while the top surface of the well 67 is made to remain open as shown in FIG. 80E.

Meanwhile, it is also possible to form the second fluidic channel 67 instead of the well 67 by adhering the member 66 to the top surface of the glass substrate 69 so as to cover the first recess portion 63 (not shown).

In this case, the first fluidic channel 68 can be differently referred to as the third fluidic channel 68.

As the method of adhering the member 66 and the top surface of the glass substrate 69, a well-known method may be conducted depending on the material of the member 66.

In addition, it is also possible to appropriate install electrodes, wires, and the like for an electrophysiological measurement in the first fluidic channel 68 during the adhering.

The material of the member 66 is not particularly limited, and it is possible to use a resin substrate such as PDMS or PMMA, or a glass substrate.

In addition, the material of the member 66 may be constituted by a material that does not transmit light (for example, visible light) used for observation.

In a case in which the formation of a lipid membrane is the only object, is the material of the member 66 does not necessarily need to transmit light that is used for observation.

When a member that transmits light used for observation is used, optical observation from the top surface becomes possible, which is preferable.

The member that is used to form the first fluidic channel 68 and covers the second recess portion 64 does not necessarily need to be a member that transmits light that is used for observation, and may be a member that does not transmits light that is used for observation.

As described above, the base body of the invention includes the base member, the space which is provided in the base member and allows a fluid (liquid or gas) to flow in, and the micropores that communicate the space to the outside of the base member, and at least the portions that configure the micropores in the base member are formed of a single member.

In the base body of the invention, the single member preferably transmits at least some wavelengths of light from light having a wavelength of 0.1 µm to 10 µm.

In the base body of the invention, the material of the single member is preferably silicon, glass, silica, or sapphire.

In the base body of the invention, the micropores are preferably formed by irradiating the base body with a laser, and, furthermore, removing the modified regions irradiated with the laser through an etching treatment.

As described above, the manufacturing method of the invention preferably includes at least the process A1 in which a laser having a pulse duration on the order of picoseconds or less is irradiated to areas in the single member which become the micropores so as to form modified regions in the areas, the process A2 in which the space is formed in the single member, and the process A3 in which the modified regions are removed from the single member through etching.

In addition, as described above, the method of manufacturing the base body of the invention preferably includes at least the process B1 in which the space is formed in the single member, the process B2 in which a laser having a pulse duration on the order of picoseconds or less is irradiated to areas in the single member which become the micropores so as to form modified regions in the areas, and the process B3 in which the modified regions are removed from the single member through etching.

The base body of the invention described above can trap fine particles such as microorganisms or cells, and is available for a plurality of uses such as formation of a lipid membrane.

In addition, according to the method of manufacturing the base body of the invention, it is possible to provide a base body which can trap fine particles such as microorganisms or cells, is available for a plurality of uses such as formation of a lipid membrane, and has micropores.

The fine particles which are trapped by the base body of the invention and are included in the fluid are not particularly limited, and are preferably circulated in the fluidic channels.

Examples thereof include particles and the like formed of microorganisms, cells, organic substances, or inorganic substances.

Examples of the microorganisms include bacteria, fungus, mold, large viruses, and the like.

Examples of the cells include cells for which floating cultivation is available such as red blood cells and white blood cells.

Examples of the particles formed of the organic substances include particles, activated carbon particles, and the like which are formed of a macromolecule such as a resin or a polysaccharide.

Examples of the particles formed of the inorganic substances include metal particles such as silica particles and gold colloid particles.

The particles formed of the organic substances and the particles formed of the inorganic substances may be functional particles having antibody molecules and the like bound to the surface or inside.

The shape of the particles formed of the organic substance and the shape of the particles formed of the inorganic substance are not particularly limited.

Examples of the fine particles of the invention include particles having all steric shapes such as a sphere, cube, cuboid, polyhedron, doughnut-like solids, and ribbon-like solids.

The size of the particles formed of the organic substances and the particles formed of the inorganic substances is not particularly limited as long as the particles are larger than the diameter of the opening (minor axis) of the first end portion of the micropore which configures the adsorption portion.

That is, the particles need to be large enough to prevent passing through the micropores.

The fine particles trapped by the base body of the invention are preferably microorganisms or cells.

The surface shape of microorganisms or cells may change relatively flexibly.

Therefore, it is possible to sufficiently closely attach the microorganisms or cells to the adsorption portions S, and adsorb the microorganisms or cells more strongly.

Furthermore, in a case in which the fine particles are microorganisms or cells, it is possible to highly accurately carry out an electrophysiological measurement of the fine particles.

An embodiment of the base body of the invention for trapping the fine particles is as described above using a case in which the fine particles are microorganisms or cells as an example.

That is, even in a case in which the fine particles are fine particles other than microorganisms or cells, it is possible to trap the fine particles other than microorganisms or cells at the adsorption portions in the base body of the invention similarly to the case in which the fine particles are microorganisms or cells.

In addition, the method of manufacturing the base body of the invention can be conducted similarly to the method of manufacturing the base body for trapping microorganisms or cells of the invention.

The base body for trapping microorganisms or cells of the invention and the method of manufacturing the base body can be widely used for operation and manufacturing of micro fluid devices and the like for carrying out a variety of observations, analyses, and measurements by trapping microorganisms or cells included in water, air, or the like.

The base body for forming a lipid membrane of the invention and the method of manufacturing the base body can be widely used for operation and manufacturing of micro fluid devices and the like for carrying out a variety of observations, analyses, and measurements by forming a fine lipid membrane.

The base body of the invention and the method of manufacturing the base body can be widely used for operation and manufacturing of micro fluid devices and the like for carrying out a variety of observations, analyses, and measurements by trapping fine particles such as microorganisms or cells included in water, air, or the like or forming a lipid membrane.

What is claimed is:

1. A method of manufacturing the base body for trapping microorganisms or cells, comprising:
    preparing a substrate formed of a single member;
    irradiating, with a laser having a pulse duration on an order of picoseconds or less, areas in the substrate which become fine vacuum holes communicating with an outside of the substrate and forming modified regions in the areas;
    forming at least one of a well and a fluidic channel as a space which communicates with the fine vacuum holes and which allows fluid including microorganisms or cells to flow in the substrate such that the space opens to a first face of the substrate that has an inner side surface along a thickness direction of the substrate; and
    removing the modified regions from the substrate through etching thereby forming the fine vacuum holes such that a first end of each of the fine vacuum holes opens to the inner side surface and communicates with the space and such that a second end of each of the fine vacuum holes is exposed to a second face of the substrate and communicates with the outside of the substrate.

2. The method of manufacturing the base body according to claim 1,
    wherein an irradiation intensity of the laser is lower than or equal to a lower limit value of a laser irradiation intensity at which a periodic structure is capable of being formed in the modified regions and is greater than or equal to a lower limit value of a laser irradiation intensity at which an etching resistance of the modified regions is capable of being decreased when the modified regions are formed.

3. The method of manufacturing the base body according to claim 1,
    wherein the laser is condensed using a lens.

4. A method of manufacturing the base body for trapping microorganisms or cells, comprising:
    preparing a substrate formed of a single member;
    forming at least one of a well and a fluidic channel as a space which allows fluid including microorganisms or cells to flow in the substrate such that the space opens to a first face of the substrate that has an inner side surface along a thickness direction of the substrate;
    irradiating, with a laser having a pulse duration on an order of picoseconds or less, areas in the substrate which become fine vacuum holes communicating with the space and an outside of the substrate and forming modified regions in the areas; and
    removing the modified regions from the substrate through etching thereby forming the fine vacuum holes such that a first end of each of the fine vacuum holes opens to the inner side surface and communicates with the space and such that a second end of each of the fine vacuum holes is exposed to a second face of the substrate and communicates with the outside of the substrate.

5. A method of manufacturing the base body for forming a lipid membrane, comprising:
    preparing a substrate formed of a single member;
    irradiating, with a laser having a pulse duration on an order of picoseconds or less, areas in the substrate which become micropores communicating with an outside of the substrate and forming modified regions in the areas;
    forming at least one of a well and a fluidic channel as a space which communicates with the micropores and which allows liquid including lipids to flow in the substrate such that the space opens to a first face of the substrate that has an inner side surface along a thickness direction of the substrate; and
    removing the modified regions from the substrate through etching thereby forming the micropores such that a first end of each of the micropores opens to the inner side surface and communicates with the space and such that a second end of each of the micropores is exposed to a second face of the substrate and communicates with the outside of the substrate.

6. The method of manufacturing the base body according to claim 5,
    wherein an irradiation intensity of the laser light is lower than or equal to a lower limit value of a laser irradiation intensity at which a periodic structure is capable of being formed in the modified regions and is greater than or equal to a lower limit value of a laser irradiation intensity at which an etching resistance of the modified regions is capable of being decreased when the modified regions are formed.

7. The method of manufacturing the base body according to claim 5,
    wherein the laser is condensed using a lens.

8. A method of manufacturing the base body for forming a lipid membrane, comprising:
    preparing a substrate formed of a single member
    forming at least one of a well and a fluidic channel as a space which allows liquid including lipids to flow in the substrate such that the space opens to a first face of the substrate that has an inner side surface along a thickness direction of the substrate;
    irradiating, with a laser having a pulse duration on an order of picoseconds or less, areas in the substrate which become micropores communicating with the space and an outside of the substrate and forming modified regions in the areas; and
    removing the modified regions from the substrate through etching thereby forming the micropores such that a first end of each of the micropores opens to the inner side surface and communicates with the space and such that a second end of each of the micropores is exposed to a second face of the substrate and communicates with the outside of the substrate.

9. A method of manufacturing the base body, comprising:
    preparing a substrate formed of a single member;
    irradiating, with a laser having a pulse duration on an order of picoseconds or less, areas in the substrate which become micropores communicating with an outside of the substrate and forming modified regions in the areas;
    forming at least one of a well and a fluidic channel as a space which communicates with the micropores and which allows fluid to flow in the substrate such that the space opens to a first face of the substrate that has an inner side surface along a thickness direction of the substrate; and
    removing the modified regions from the substrate through etching thereby forming the micropores such that a first end of each of the micropores opens to the inner side surface and communicates with the space and such that a second end of each of the micropores is exposed to a second face of the substrate and communicates with the outside of the substrate.

10. The method of manufacturing the base body according to claim 9,
    wherein an irradiation intensity of the laser light is lower than or equal to a lower limit value of a laser irradiation intensity at which a periodic structure is capable of being formed in the modified regions and is greater than or equal to a lower limit value of a laser irradiation intensity at which an etching resistance of the modified regions is capable of being decreased when the modified regions are formed.

11. The method of manufacturing the base body according to claim 9,
wherein the laser is condensed using a lens.

12. A method of manufacturing the base body, comprising:
preparing a substrate formed of a single member;
forming at least one of a well and a fluidic channel as a space which allows fluid to flow in the substrate such that the space opens to a first face of the substrate that has an inner side surface along a thickness direction of the substrate;
irradiating, with a laser having a pulse duration on an order of picoseconds or less, areas in the substrate which become micropores communicating with the space and an outside of the substrate and forming modified regions in the areas; and
removing the modified regions from the substrate through etching thereby forming the micropores such that a first end of each of the micropores opens to the inner side surface and communicates with the space and such that a second end of each of the micropores is exposed to a second face of the substrate and communicates with the outside of the substrate.

* * * * *